United States Patent
Doty et al.

(10) Patent No.: US 9,487,451 B2
(45) Date of Patent: Nov. 8, 2016

(54) ENDOPHYTIC YEAST STRAINS, METHODS FOR ETHANOL AND XYLITOL PRODUCTION, METHODS FOR BIOLOGICAL NITROGEN FIXATION, AND A GENETIC SOURCE FOR IMPROVEMENT OF INDUSTRIAL STRAINS

(71) Applicant: University of Washington Through Its Center for Commercialization, Seattle, WA (US)

(72) Inventors: Sharon L. Doty, Seattle, WA (US); James Trotter Staley, Shoreline, WA (US); Michael Su, Seattle, WA (US); Azra Vajzovic, Kirkland, WA (US); Renata Bura, Seattle, WA (US); Regina Redman, Seattle, WA (US); Zareen Khan, Redmond, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 0 days.

(21) Appl. No.: 14/209,709

(22) Filed: Mar. 13, 2014

(65) Prior Publication Data
US 2014/0283569 A1 Sep. 25, 2014

Related U.S. Application Data

(63) Continuation-in-part of application No. 13/256,426, filed as application No. PCT/US2010/027234 on Mar. 12, 2010, now Pat. No. 8,728,781.

(60) Provisional application No. 61/160,077, filed on Mar. 13, 2009.

(51) Int. Cl.
| | |
|---|---|
| *C12P 7/18* | (2006.01) |
| *C05F 11/08* | (2006.01) |
| *C12N 9/04* | (2006.01) |
| *C12P 7/06* | (2006.01) |
| *C12P 7/10* | (2006.01) |
| *C12R 1/645* | (2006.01) |
| *C12N 15/81* | (2006.01) |

(52) U.S. Cl.
CPC ............. *C05F 11/08* (2013.01); *C12N 9/0006* (2013.01); *C12N 15/815* (2013.01); *C12P 7/06* (2013.01); *C12P 7/10* (2013.01); *C12P 7/18* (2013.01); *C12R 1/645* (2013.01); *Y02E 50/16* (2013.01); *Y02E 50/17* (2013.01); *Y02P 20/52* (2015.11)

(58) Field of Classification Search
CPC ................................ C12N 9/0006; C12P 7/06
USPC ................................................ 435/158, 254.2
See application file for complete search history.

(56) References Cited

U.S. PATENT DOCUMENTS 5,981,239 A  11/1999 Liu
8,728,781 B2 *  5/2014 Doty ................... C12N 9/0006
                                                    435/158

OTHER PUBLICATIONS

Aksu, Z., et al., Carotenoids prodiction by the yeast Rhondotorula mucilaginosa: Use of agricultural wastes as a carbon source, Process Biochemistry, (2005), vol. 40, pp. 2985-2991.
Chica et al., Semi-rational approaches to engineering enzyme activity: combining the benefits of directed evolution and rational design. Current Opin. Biotechnol. 16 (4):378-84, 2005.
Devos et al., Proteins: Structure, Function and Genetics, 2000, vol. 41: 98-107.
Kisselev L., Structure, 2002, vol. 10:8-9.
Sen et al., Developments in Directed Evolution for Improving Enzyme Functions. Appl Biochem Biotechnol. 143 (3):212-23, 2007.
Sheys, G. H., et al., Aldose Reductase from Rhondotorula, J. Biol. Chem., (1971), vol. 246, pp. 3824-3827.
Verduyn, C., et al., Properties of the NAD(P)H-dependent xylose reductase from the xylose-fermenting yeast Pichia stipitis, Biochem. J., (1985), vol. 226, pp. 669-677.
Whisstock et al., Quarterly Reviews of Biophysics 2003, vol. 36 (3): 307-340.

* cited by examiner

*Primary Examiner* — Tekchand Saidha
(74) *Attorney, Agent, or Firm* — Kilpatrick Townsend and Stockton LLP

(57) ABSTRACT

The present invention provides novel endophytic yeast strains capable of metabolizing both pentose and hexose sugars. Methods of producing ethanol and xylitol using the novel endophytic yeast are provided herein. Also provided are methods of fixing nitrogen and fertilizing a crop using the novel endophytic yeast strains provided herein.

14 Claims, 47 Drawing Sheets

| Media types | Glucose removal (%) | Ethanol yield (%) | Xylitol yield (%) |
|---|---|---|---|
| MS | 12.0 (0.1)) | 0.9 (0) | 1.9 (0) |
| MS + P | 66.5 (0.2) | 0.3 (0) | 3.0 (0) |
| MS+P+E | 67.3 (0.1) | 1.3 (0) | 5.2 (0) |
| MS+E | 100.0 (0.4) | 81.8 (0.7) | 2.7 (0) |

*FIG. 20*

| Media types | Xyl % removal | Ethanol yield (%) | Xylitol yield (%) |
|---|---|---|---|
| MS | 8.0 (0) | 0.0 (0) | 6.0 (0) |
| MS + P | 88.0 (0.6) | 0.0 (0) | 58.5 (0.3) |
| MS+P+E | 89.0 (0.8) | 0.5 (0) | 75.9 (0.2) |
| MS+E | 96.1 (1.0) | 1.2 (0) | 71.7 (0.2) |

FIG. 21

| Yeast concentration (g/L) | Glucose removal (%) | Ethanol yield (%) | Xylitol yield (%) |
|---|---|---|---|
| 1 | 88.0 (0.4) | 72.0 (0.1) | 3.6 (0.4) |
| 5 | 100.0 (0.4) | 81.8 (0.6) | 4.7 (0.3) |
| 10 | 100.0 (0.5) | 82.9 (0.4) | 3.9 (0.8) |
| 15 | 100.0 (0.6) | 84.1 (0.3) | 2.4 (0.5) |

FIG. 22

| Yeast concentration (g/L) | Xylose removal (%) | Ethanol yield (%) | Xylitol yield (%) |
|---|---|---|---|
| 1 | 84.4 (0.4) | 0.3 (0.0) | 27.6 (0.3) |
| 5 | 89.3 (0.2) | 0.68 (0.2) | 39.7 (0.4) |
| 10 | 91.9 (0.5) | 0.06 (0.3) | 42.6 (0.3) |
| 15 | 77.2 (0.3) | 0.07 (0.6) | 43.3 (0.4) |

*FIG. 23*

Contig1 - Ad1 18S SEQUENCE
```
NGCGATNCAGCTCCGGCCGCCATGGCGGCCGCGGGAAATTCGATTCCGTCAGGTTCACCTACGGAAACCTTGATTACGAC
TTTTACTTCCTCTAAATGACCAAGTTCGTACAACTTCTCGGCAGTCGGGTGCTCTCGCGAGCTCCCAATAGCCAATCCGG
AGGCCTCACTAAGCCATTCAATCGGTAGTAGCGACGGGCGGTGTGTACAAAGGGCAGGGACGTAATCAACGCGATCTGAT
GAATCACGCTTACTAGGTATTCCTCGTTGAAGAACAATAATTGCAATGTTCTATCCCCATCACGACAGAGTTTCACAAGA
TTACCCATGCCTTCCGGCAAAGGTGGTAGACTCGCTGGCTCTGTCAGTGTAGCGCGCGTGCGGCCCAGAACATCTAAGGG
CATCACAGACCTGTTATTGCCTCAAACTTCCATCAGCTAAACGCTGATAGTCCCTCTAAGAAGACAGCAGCTAGCCAAAG
CCGGCTGGTCTATTTAGCAGGTTAAGGTCTCGTTCGTTATCGGAATTAACCAGACAAATCACTCCACCAACTAAGAACGG
CCATGCACCACCAACCACAAGATCAAGAAAGAGCTATCAATCTGTCAATCCTTATTGTGTCTGGACCTGGTGAGTTTCCC
CGTGTTGAGTCAAATTAAGCCGCAGGCTCCACACCTGGTGGTGCCCTTCCGTCAATTCCTTTAAGTTTCAGCCTTGCGAC
CATACTCCCCCCCGAACCTCATTTAAAGATTTCTCTTCGGGTGCCGATACAGTCATTAAAAATCCTGTACCGATCCCCAA
TTGGCATAGTTTACAGAAGAGACTACAACGGTATCTAATCGTTTTCGATCCCCCTTCCTTCGTTCTTGATCAAKGAAAAC
ATCCTTGGCAAAKGCtTTTCGCAGTAGTTTGTYTTCCGGCAATCCAAGAATTTCACYTCTGACGACGGAATACnAAATGc
CCCCCAACTATCCCTATTAATCATTACGGSnGATYTCAGAAACCAACAAAAWnGGGAACGCGCGTCCTATTTTATTATTC
CATGCTAATGTATTCGGGGCAAAGGCCTGCTTGAACACTCTAATTTTTTCAAAGTAAAAGTCCTGGTTTGCGACGACACC
CAGTAAAGGACATCGCCGTTCACCAGGAGGTAAGGCTCCGTCAAACAAGTACACACCAAGAAGGCGGACCGGCTGACAGA
GCCCGAAGTTCGACTACGAGCTTTTTAACGGCAACAATTTTAATATACGCTATTGGAGCTGGAATTACCGCGGCTGCTGG
CACCAGACTTGCCCTCCAATTGATCCTCGTTAAGGGATTTAAATTGTACTCATTCCAATTGCAAGACCCGTAAGAGCCCT
GCATTGTTATTTATTGTCACTATCTCGGCAAAGTGTTGCCAGGGGATAATTTGCGCGCCTGCTGCGTGTCCTTAGACCTG
AGGGCCGTTTCTCAGGCCCTCTCTCCGGAATCGAACCCTTATTCCCCGTTACCCGTCATCACCATGGTAGGCCTCTATCC
TACCATCGAAAGTTGATAGGGCAGATATTTGAATGAAGCATCGCCGGCGCAAGGCCATGCGATTCGAGCAGTTATCATGA
TTCACCATAGGGACCCGAAGGCCATTGGTTTTGGATCTAATAAATACATCCCTTCCAGAAGTCGGGATTTTTCAGCATGT
ATTAGCTCTAGAATTACCACAGTTATCCATGTAGTAAGGTACCATCAAATAAACTATGACTGATTTAATGAGCCATTCGC
AGTTTCACTGTTTATTGCTTAAACTTAGACATGCATGGCTTAATCTTTGAGACAAGCATATGACTACAATCACTAGTGAA
TTCGCGGCCGCCTGCAGGTCGACCATATGGGAGAGCTCCACGCGTGAGA
```

FIG. 32

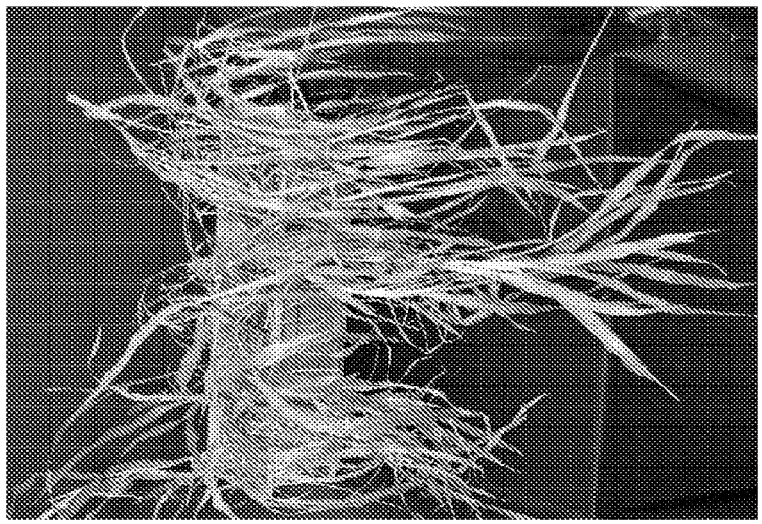
FIG. 42B WP1
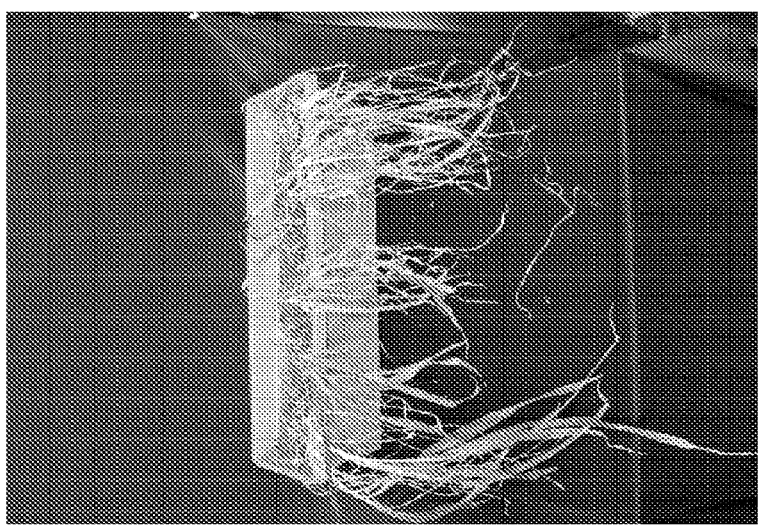
FIG. 42A Nonsymbiotic

>PTD3 XDH gene
ATGGCTCCGACCAACACCCCACTTTCGCCTCCGCTCGCCGAAGACACGGCCGCAACCT
CGCGCAACGTCAGCTTCGTTCTGCACGGAATCGACGACGTCCGCTTTGAAGAGAGGC
CGGTTCCTGTCGACTGCGATGATGATGCCGCCATTGTCGCTCCCAAGGCTACGGGAATC
TGCGGCAGCGACGTACACTACCTCAAGCACGGCCGAATCGGCGACTTTATCGTTAAGG
ACCCTATGGTTCTCGGACACGAGAGTGCCGCCGTCGTCGTCAAGGTCGGCAAGAATGT
CAAGAACGTCAAGCCGGGCGACCGGCGTTGCCCTTGAGCCGGGCAAGTCGTGCCGATC
CTGCTACGACTGCAAAGGTGGTCATTACGAACGCTGCCCGGACATGATCTTTGCGGCG
ACTCCTCCTTACGATGGTACCCTTGCCGGACGCTACGTTCTTCCGGCCGACCTCTGCTA
CAAGCTGCCCGGACAACCTGTCCATGGAGGAGGGAGCTCTCCTTGAGCCCATGTCGGTG
GGCGTCCACGCAGTTGCCAAGGTTGCCGAGCTCAAGCCGGGCTCGAACGTGGTGGTG
TTTGGTGCCGGACCGGTCGGACTCCTCACCGCAGCCGCGGCAAAAGGCCTCGGTGCT
GCCCGCGTCATTGCCGTCGACATTCAGGAGAGTCGCTTGCAATTCGCCAAGGAGAACG
GCCTGATCCACGACTACTGTGTCCCGTCAAAGCCGCAAGAAGGCGAGGACAAGGTTG
ACTTCCAGCGACGAAACGCCAAGGAGATTCAGACTCGGTTCGGCTTCACGGAGCGAG
GGGCGACCGGCGTCGACTACGTCTTTGAGTGCTCTGGCGCCGAGGTCTGCATCGGAAC
TTCGGTTTTCCTGCTCAAGCACGGTGGCACGATGGTTCAGATCGGTATGGGCCGGCCC
GACATCAGCCTCGACATGCACACCGTCCTTACCCACGAACTCACCATCAAGGGCAGCT
TCCGGTACGGCCCGGACGTGTACCGGCTCTCGCTCGACCTGGTCGCTCGCGGCGCCGT
CAACCTCAAATCGCTCATCACTCACCGCTACACTTTCAAGGAGGCGAAGGAGGCGTTC
GAAGCCAACACGAAGGGCGTCGGCAAAGATGGCCACGCCGTCATCAAGATCATCATT
GCCGGCCCGCTCGAGTCTGACACGGCATGA

*FIG. 44*

>PTD3 XR gene
ATGTCGCAGCAGATCCCCTCCGTCAAGCTCTCGAACGGCGCCGAGTTCCCCCTCCTTG
GCTTCGGCACCTGGCAGTCCGCCCCGGGCGAGGTCGGCAAAGCCGTTGAGGTCGCTC
TCAAGGCCGGCTACCGGTCACCTCGACCTTGCCAAGGTCTACGGCAACCAGAAGGAGA
TTGCTCCGGCGATCGCCAACTCGGGCGTTGACCGCAAGGACATCTTCATCACCTCGAA
GCTCTGGAACCCGCAGCACAAGCCGGAACTCGTCGAGGCTGCTCTCGACGACACCCT
CAAGGAGCTCGGCCTCGAGTACCTCGACCTCTACCTCATCCACTGGCCGGTTGCTTTCC
CGGTTGAGGGCGACCCCCACTCGAACCTCTTCCCGAAGGAGAACGGCGAGTGCAAGA
TCGACACCTCGATCTCGATCGTCGACACCTGGAAGGCGATGATCAAGCTCCTCGACAC
TGGCAAGACCAAGGCTGTCGGTGTTTCCAACTTCTCGCCGGCCATGGTCGACGCCATC
ACCGAGGCCACTGGTGTCAAGCCGGTCGTCAACCAGATCGAGCGTCACCCGCCGCCTG
CTCCAGAAGGACCTCCTCAAGCACCACAAGGAGAAGAACATTGTCGTCACCGCCTAC
TCCCGGCTTCGGAAACAACAGCGTCGGCGAGCCGCTCCTCCTCGAGCACCCGACCGTC
AAGAAGATCGCCGAGGCCAAGGGCGCCAACCCGGGTCAGGTCCTCATTGCCTGGGGC
ATGCACGGCGGCCACGCCATCATTCCCGAGTCGGTTACCCCGTCGCGCATCGAATCGA
ACTTCAAGGTCATCTCGCTCACCGACGACGAGGTTGCTGAGATCAACAAGATCGGCGA
GGAGAAGCCCGCACGTTTTAACCTGCCGATCGATTATACACCAAAGTCGAACATCAAC
GTCTTTGACACGCCGCAGGAGAAGGACGCCAAGTACCAGGTCAAGATCCAGTAA

FIG. 45

>WP1 xylose reductase gene cDNA ORF verified by RT-PCR
ATGCCCTCACGTCACCCAGCCACCCGCGTCCTTCCAGCTCAACACGGGCGGTCGATCCCGT
CTGTCGGCCTCGGCCACGTGGCAGGCCAAGCCGGGCGAGGTCGGCGAGCCGTCGAGCAAG
CCCTCAAGTCGGCTACGTCACCTGACTGGCGGCTCATCTACGAGATCTTTATCACGTGAAGT
CGGCGCTGGCATCAAGGCGTGAGCGTGCCGAGGTCCGAGATCGTCGAGTCGGCATCGAAGCTG
TGGAAACACGTACCACGAGTCGAGCAAGTCCTGACGAGTCGAGCAATGCGGCATCGCTCGGCG
TCGACTACCTCGACCTGTACCTCATCCACTGGCCCGTGCCGTCGGCGAACGAGTCGTCG
GCGCTCCTCCCGTCAACCCGGACGGCTCTGCGCCGTCAAGAGTCGTGGGACATGAGCA
AGACGTGGGGGAGCATGGAGGCGTCGGCGTACCTGAGGAAGTCAAGGCACGTGGTGACGTGGGGCT
CGAACTGGAGGCGTCGCGTTCAACCCGAGCACAAGCTCAAGGCCTGGTGCGACAA
CAACCAGGTCGAGCTCCACCCGTTCAACCCGAGCACAAGCTCAAGGCCTGGTGCGACAA
GCGGGGAGCATCCTCCTCGAGGCGCTACTGCCCCTCTCGACCAACTGCGCCCTCCTGTCCG
ACCCGAGCTGAAGCCATCGGCGACAAGCCGACAGGGGTCTGCCGCGGACCGTCCTCATCTC
GTACCAGCCTCAAGCGGCTGGTGCTCCCCAAGTCGGTGAGCCAGCACGCAGCATCGAG
GCCAACCTTCACCTCATCACGGCCTGATCGACATGAGCACGCTCTCTTTGGTGGACTCGCCG
CAAGGGCAAGCAGCAGGGCCAACACGCGTCTCTTTGGCCAATGGCGGGTACCTTTAG
ATTGGTATCCTGCGCAGGCGGATGCTGGCCAATGGCGGGTACCTTTAG

*FIG. 46*

>WP1 xylitol dehydrogenase gene cDNA ORF verified by RT-PCR
ATGAGCGGCTCCAGTCTCGTCGTCCCGTCCAGCTCTCGCTGCTGCTCCCGTCCAGCAACGAGGACACGGGCCTCCCACCGGCGGCCACAACATCTC
CTGCGTCTTGCACGGCATCGACGACGTCCCGTTCGAGGACCGGCTGTGCCGACCGAGTGCGGGAGGACGACG
CGATCGTTTCGCCAGCCAAAATCTCGGTTTGCGGCTCCGACACGACTATATCAAGCATGCCGATCGGCGAC
TTTATCGTCGAGAGCCCATGGTCCCTCGGCACGAGACGGGCGTCGTCCTGCAGGTCGTGCTCCAGGTTGGCAGCCGCGTCAC
CAACATCAAGGCCGGACCGGGACCGGTCGACGCCGTCGAACCAGGTCGTCCTGCAGGGTCTGCTCCGACTGCAAGGCCG
GCTTCTACAACCGCTGCGCCGACCTGTGCCTACCCCGGCCTTTGCAGCTACCCGGCCAACATGTCTCTCGGAGGAGGCCTTATGATGGCACCCTCGCCGCTACTAC
ACGCTCCCTCGGTGTCCACGCCGTTCACAGGTGGCCACAGGTCGCCCAACGCGCCAAATGAAAAGCGCCGGCGCAAGGTCATCTCGCCCATGGTTGTCTTTGGGCAG
GTCGGTCGGTCGGCCTCTCACGTGCCGCTGTCGAGGAGCAGCCGCAAGGTCATCTTCCGCCAAGCCCAGGACGG
GAGGCTCGTCTCGCCACGCCGACTACCCGGCCAAGCCGACTACCTTCGGAACGCTTTGGGTTCGAGGAGCGGGGC
CGAGGCCAAGCCGACTACCCGTCGACCTCGTCCTCGCAGGTCGACATGGGCGAGGTGTGCATCGAGACCCGGGCGTCTTCGTCCTCAAG
CTCGGGGGTCGGACCCTCGTCGTTCCGCTCATCGGGGACTCGGCGAGGTGCATCGGCGTTACGAGCTCGACGGCGGCGACG
CACGGGCGGCCACGCTGGAAGGCTCAAGGGTCGTCATCTCGGCACAGGTACGCGTTCCGACGACGACTCAAGGGCGTTCGAGGCGAAC
CGAGTTGACGGTCAACCTCAAGTGCTGCGTTCATCTCGGAAGGGCTACAGGCCGTTGATCAAGGCCGGTCATCGACGAGGCT
CGAGTGA

FIG. 47

ENDOPHYTIC YEAST STRAINS, METHODS FOR ETHANOL AND XYLITOL PRODUCTION, METHODS FOR BIOLOGICAL NITROGEN FIXATION, AND A GENETIC SOURCE FOR IMPROVEMENT OF INDUSTRIAL STRAINS

CROSS-REFERENCES TO RELATED APPLICATIONS

This application is a continuation in part of U.S. application Ser. No. 13/256,426, filed Dec. 5, 2011, now U.S. Pat. No. 8,728,781, which is a U.S. National Phase Application under 35 U.S.C. §371 of International Application No. PCT/US2010/027234, filed on Mar. 12, 2010, which claims the benefit of U.S. Provisional Application No. 61/160,077, filed Mar. 13, 2009, the contents of each of which are expressly incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under Grant No. MCB-0646932 awarded by the National Science Foundation, Grant No. GO12026-278 awarded by the Consortium of Plant Biotechnology Research (CPBR), Grant No. EF-0838091 awarded by the National Science Foundation Small Grant for Exploratory Research, and Grant No. CBET 0930909 awarded by the National Science Foundation. The government has certain rights in this invention.

REFERENCE TO A "SEQUENCE LISTING," A TABLE, OR A COMPUTER PROGRAM LISTING APPENDIX SUBMITTED AS AN ASCII TEXT FILE

This application includes a Sequence Listing as an ASCII text file named "-86-2.txt" created May 16, 2013, machine format IBM-PC, MS-Windows operating system, and containing 45,056 bytes. The material contained in this text file is incorporated by reference in its entirety for all purposes.

BACKGROUND OF THE INVENTION

Endophytic microorganisms occur within living plant tissues without causing apparent damage to the host (Petrini, 1991). To date, endophytic yeasts have been isolated from a variety of plants, including roots of *Zea mays* L. (maize) (Nassar et al., 2005) and roots of *Musa acuminate* L. (banana) (Cao et al., 2002), and leaves of *Oryza sativa* L. (rice) (Tian et al., 2004), *Solanum lycopersicum* L. (tomato) (Larran et al., 2001), and *Triticum aestivum* L. (wheat) (Larran et al., 2002). In a series of studies on endophytic microorganisms in wild and hybrid *Populus* species, (Doty et al., 2005; Doty et al., 2009) three yeast strains were isolated.

Identification of yeast species from morphological and physiological characteristics has been complemented with and improved by molecular methods in the last 20 years. Analyses of small subunit (18S) ribosomal RNA (rRNA) gene sequences, extremely important in phylogenetic analyses of species in bacteria, generally are not adequate to differentiate yeast species (James et al., 1996; Kurtzman and Robnett, 2003). Sequencing domains 1 and 2 (D1/D2) of large subunit (26S)rRNA gene have been used by many researchers to determine yeast species because this approach is rapid and effective, and a large number of sequences are available for comparison in online databases (Kurtzman and Robnett, 1998; Fell et al., 2000; Kurtzman, 2006). The internal transcribed spacer (ITS) regions ITS1 and ITS2, flanking the 5.8S gene of rRNA, are also highly substituted and are used for yeast identification. Scorzetti et al. (2002) found that analyzing ITS sequences allowed them to detect species among basidiomycetous species more effectively than using D1/D2. For example, *Sporobolomyces holsaticus* Windisch ex Yarrow & Fell and *Sporidiobolus johnsonii* Nyland are identical in D1/D2 sequences, register 93% DNA hybridization (Boekhout, 1991), and differ in five base positions in the ITS sequences. In contrast, *Rhodotorula glutinis* (Fresen.) F. C. Harrison and *Rhodotorula graminis* Di Menna are identical in the ITS region but differ in one base position in D1/D2; they are considered to be separate species based on 35-40% DNA hybridization (Gadanho and Sampaio, 2002). Consequently, it appears useful to sequence both D1/D2 and ITS regions when distinguishing closely related species, while defining species taxonomically requires classical phenotypic information (Scorzetti et al., 2002).

Recently, the role of endophytic microorganisms in the promotion of plant growth has received increased attention. Endophytes can promote plant growth through different mechanisms, including delivery of fixed nitrogen to host plants, production of plant growth regulators, and biological control of plant pathogens (Ryan et al., 2008). Endophytic yeast strains have been shown to be able to promote the growth of maize (Nassar et al., 2005) and *Beta vulgaris* L. (sugar beet) (El-Tarabily, 2004) by producing plant auxins, such as indole-3-acetic acid (IAA) and indole-3-pyruvic acid (IPYA) (Nassar et al., 2005).

Efficient industrial production of biofuels, such as bioethanol, holds promise for serving the growing energy needs of the world in the near future. Ethanolic fermentation of cellulosic and lignocellulosic biomass by microorganisms such as yeast is currently employed in the industrial production of bioethanol. However, the lack of non-pathogenic microorganisms that efficiently metabolize both five carbon (pentose) and six carbon (hexose) sugars in the presence of high levels of ethanol, limits the efficiency and therefore the economic feasibility of large-scale fermentations of certain lignocellulosic carbon sources that contain high levels of hemicellulosic biomass. As an example of this, in the absence of corn, the maize plant is comprised of about 24% Xylose and 2% arabinose, both of which are pentose sugars that are poorly utilized by the industrial yeast strains currently employed (Antoni et al., *Appl Microbiol Biotechnol* 77:23-35 (2007)).

Several groups have attempted to traverse this problem by genetically engineering strains of *Saccharomyces cerevisiae* to contain enzymes necessary for efficient metabolism of xylose. In initial attempts, various bacterial xylose isomerases were expressed in *S. cerevisiae* (Amore et al., *Appl Microbiol Biotechnol* 30:351-357 (1989); Ho et al., *Biotechnol Bioeng Symp* 13:245-250 (1983); Moes et al., *Biotechnol Lett* 18:269-274 (1996); Sarthy et al., *Appl Environ Microbiol* 53:1996-2000 (1987); Walfridsson, et al., *Appl Environ Microbiol* 62:4648-51 (1996)). However, only minimal xylose metabolism was found in these recombinant yeast at temperatures suitable for industrial application.

Other groups have tried to enhance the ethanolic fermentation of *S. cerevisiae* by exogenously expressing *P. stipitis* xylose reductase (XR) and xylose dehydrogenase (XDH) (Kötter and Ciriacy, *Appl Microbiol Biotechnol* 38:776-783

(1993); Tantirungkij et al., *J Ferm Bioeng* 75:83-88 (1993); Walfridsson et al., *Appl Microbiol Biotechnol* 48:218-224 (1997)). These studies also failed to yield recombinant *S. cerevisiae* strains that utilized xylose for high yield ethanolic fermentation.

U.S. Pat. No. 7,091,014 to Aristidou et al. describes the genetic engineering of fermenting microorganisms, including *S. cerevisiae* and *Schizosaccharomyces pombe*, to express an NAD-dependent glutamate dehydrogenase (GDH) or malic enzyme (ME). These modified yeast display modest increases in ethanol and xylitol production, but do not appear to metabolize xylose any faster than control strains lacking the GDH or ME enzymes.

U.S. Pat. No. 7,253,001 to Wahlbom et al. provides genetically engineered yeast for the ethanolic fermentation of xylose. The engineered yeast of U.S. Pat. No. 7,253,001 recombinantly express exogenous genes for xylose reductase, xylitol dehydrogenase, xylulokinase, phosphoacetyltransferase, aldehyde dehydrogenase, and optionally phosphoketolase.

Similarly, U.S. Pat. No. 7,226,735 to Jeffries and Jin provides genetically engineered yeast strains comprising heterologous gene sequences encoding xylose reductase, xylitol dehydrogenase, and D-xylulokinase enzymes, which are capable of performing fermentation of xylose. U.S. Pat. No. 7,285,403 to Jeffries et al. provides similar engineered yeast strains that additionally display reduced PHO13 expression.

One drawback to using these genetically engineered yeast strains for food and beverage production is that the products, such as ethanol and xylitol, may be regulated as novel GMO (genetically modified organism) produced food. Such regulations may result in additional safety and labeling requirements that are not needed for foods produced by using unmodified organisms. As such, there remains a need in the art for methods of efficiently fermenting pentose and hexose sugars without the use of genetically modified organisms.

Xylitol, a five carbon sugar alcohol, is an increasingly utilized sugar substitute with several desirable properties. First several studies have shown that xylitol provides anti-cariogenic effects that promote oral health (Tanzer J M., *Int Dent J.* 1995 February; 45(1 Suppl 1):65-76). Secondly, xylitol metabolism is not regulated by the insulin pathway, which makes this sweetener an attractive sugar substitute for diabetics. Similarly, xylitol is an appropriate sugar substitute for individuals who suffer from glucose-6-phosphate dehydrogenase deficiencies. Finally, xylitol has fewer calories and net effective carbohydrates than does table sugar, making it a viable dietary substitute for sucrose.

Although xylitol is present in many fruits and vegetables, extraction is inefficient and uneconomical. As such, xylitol is industrially produced through the chemical reduction of xylose. Typically, xylan-containing biomass is hydrolyzed to produce a mixture of pentose and hexose sugars, including D-xylose. After enrichment, D-xylose is then converted to xylitol in a chemical process using e.g. a nickel catalyst such as Raney-nickel. Many procedures for this process have been developed, for example see U.S. Pat. Nos. 3,784,408, 4,066,711, 4,075,406, 4,008,285, and 3,586,537. However, the use of xylitol is still limited due to the high costs of production and purification. Accordingly, improved biotechnological processes for the production of xylitol, especially from readily available carbon sources such as corn, sugar cane, and various wood sources high in hemicellulosic biomass, are highly desirable.

Several xylose-metabolizing yeast species have been suggested for use in the production of xylitol, including species of *Candida* (WO 90/08193, WO 91/10740, WO 88/05467, U.S. Pat. No. 5,998,181), mutant and genetically modified *Kluyveromyces* (U.S. Pat. No. 6,271,007), *Debaryomyces* (Rivas et al., *Biotechnol Bioeng.* 2008 Oct. 3) and genetically modified *Saccharomyces* (U.S. Pat. No. 7,226,761). However, use of the above yeasts have failed to translate into economically viable industrial procedures for the biotechnological production of xylitol. As such, there remains a need in the art for processes that utilize xylose-metabolizing microorganisms in the industrial production of xylitol.

Nitrogen fixation refers to the biological process by which atmospheric nitrogen ($N_2$) is converted into ammonia. This process is essential for life because fixed nitrogen is required for the biosynthesis of both amino acids and nucleotides and as such is required for all plant growth. Unfortunately, most plants, including industrially and commercially important crops, are unable to fix nitrogen. These plants rely on nitrogen fixation from various prokaryotes, termed diazotrophs, including species of bacteria and actinobacteria.

Due to the high fixed nitrogen requirements, fixed nitrogen is commonly a limiting resource for plant growth. To combat this, farmers typically rely on fertilizers to supplement the fixed nitrogen content of the soil used for crop growth.

Despite the need for fixed nitrogen supplementation, there are several disadvantages to the use of fertilizers and in particular chemically synthesized inorganic fertilizers. For example, synthesized nitrogen requires high levels of fossil fuels such as natural gas and coal, which are limited resources. In fact, according to the International Fertilizer Industry Association (IFA), production of synthetic ammonia currently consumes nearly 2% of the world energy production with more than 100 million metric tons of ammonia being produced in 2008.

In addition, the run-off of nitrogen-rich compounds found in fertilizers is suspected to be a major contributor to the depletion of oxygen in many parts of the ocean, especially in coastal zones, such as off the coast of the pacific northwestern region of North America. Similarly, methane and nitrous oxide emissions resulting form the use of ammonium based fertilizers may contribute to global climate change, as greenhouse gasses.

Practically speaking, the high cost of growing food crops and biomass for the production of bioenergy (i.e., bioethanol) is in part due to the high cost of fertilizers. As such, methods of nitrogen fixation and crop fertilization that reduce or eliminate the reliance on chemically synthesized fertilizers are needed to reduce the environmental, agricultural, and financial impact that accompany the use of traditional fertilizers.

The present invention provides three novel yeast isolates that are capable of metabolizing a wide range of pentose and hexose sugars, as well as novel methods for the production of bioethanol and xylitol, the fixation of nitrogen, and crop fertilization, which satisfy these and other needs in the art.

BRIEF SUMMARY OF THE INVENTION

In one aspect, the present invention provides novel endophytic yeast strains capable of metabolizing both pentose and hexose sugars. In a certain embodiment, the yeast strains are selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In specific embodiments, the stains are identified by an rRNA gene sequence selected from any one of SEQ ID NOS:7 to 18.

In a second aspect, the present invention provides biologically pure cultures of the novel endophytic yeast strains of the invention. Cultures of the invention may comprise either a single strain of endophytic yeast or a mixture of microorganisms comprising at least one of the novel yeast strains provided herein.

In another aspect of the invention, methods of producing ethanol are provided. In one embodiment, a method of producing ethanol is provided comprising fermenting a carbon source with an endophytic strain of yeast that is capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In yet another aspect of the invention, methods of producing xylitol are provided. In one embodiment, the method comprises fermenting a carbon source with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In one aspect of the invention, methods of producing mixtures of xylitol and ethanol are provided. In one embodiment, the method comprises fermenting a carbon source with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In another aspect, the present invention provides methods of producing substantially pure ethanol and/or xylitol. In certain embodiments, the methods comprise the steps of producing a mixture of xylitol and ethanol and purifying said xylitol and ethanol from the residual material. In one embodiment, the method comprises fermenting a carbon source with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In yet another aspect, the invention provides a method of producing xylitol, the method comprising the steps of hydrolytically treating a source of biomass, separating a first stream comprising xylose from a second stream comprising glucose, and fermenting said first stream with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In certain embodiments, the method further comprises fermenting said second stream with a yeast capable of producing ethanol. In a particular embodiment, the yeast is an endophytic strain capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In one aspect, the invention provides methods of producing animal feedstock. In certain embodiments, the methods comprise fermenting a carbon source. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18.

In another aspect, the invention provides a recombinant yeast capable fermenting both hexose and pentose sugars. In certain embodiments, the yeast harbors a heterologous gene sequence from an endophytic yeast strain. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In certain embodiments, the recombinant yeast is a *Saccharomyces* or a *Schizosaccharomyces* yeast strain.

In yet another aspect, the invention provides a method of producing ethanol. In one embodiment, the method comprises fermenting a carbon source with a recombinant yeast capable of fermenting both pentose and hexose sugars. In certain embodiments, the yeast comprises a heterologous gene sequence from an endophytic yeast strain capable of fermenting both pentose and hexose sugars. In certain embodiments, the yeast comprises a heterologous gene sequence from an endophytic yeast strain capable of fermenting both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In certain embodiments, the recombinant yeast is a *Saccharomyces* or a *Schizosaccharomyces* yeast strain.

In one aspect, the invention provides novel Xylose Dehydrogenase (XDH) and Xylose Reductase (XR) genes and coding sequences cloned from the endophytic yeast provided herein, as well as the polypeptides encoded therein.

In another aspect, the invention provides a method of fixing nitrogen comprising the use of an endophytic yeast of the invention or a recombinant organism harboring a heterologous gene from an endophytic yeast provided herein. In certain embodiments, the method comprises fertilization of a crop.

BRIEF DESCRIPTION OF THE DRAWINGS

FIG. 20. Effect of medium conditions on the consumption of glucose and the production of ethanol and xylitol by PTD3 yeast.

FIG. 21. Effect of medium conditions on the consumption of xylose and the production of ethanol and xylitol by PTD3 yeast.

FIG. 22. Effect of yeast concentration on the consumption of glucose and the production of ethanol and xylitol by PTD3 yeast.

FIG. 23. Effect of yeast concentration on the consumption of xylose and the production of ethanol and xylitol by PTD3 yeast.

FIG. 32. 18S Ribosomal sequence (SEQ ID NO:18) for the Ad1 yeast isolated from *Arundo donax* (giant reed).

FIG. 42. Corn growth after 11 weeks in nitrogen-limited conditions with (B) or without (A) WP1 inoculation. Three different corn varieties (lines 1, 2, and 3) were planted in each container. Biomass of the uninoculated plants was 9.3 g, 3.9 g, and 15.0 g whereas the biomass of the WP1 inoculated plants was 63 g, 87.1 g, and 45.1 g. In addition, the % viability in WP1 colonized plants (58-92%) was higher than uninoculated plants (8.3-29.2%) plants. Statistical analysis indicated significant differences (P≤0.1) for both viability and biomass with WP1 symbiotic plants having higher viability and biomass compared to uninoculated plants.

FIG. 44. PTD3 XDH-encoding gene open reading frame (SEQ ID NO:47).

FIG. 45. PTD3 XR-encoding gene open reading frame (SEQ ID NO:45).

FIG. 46. WP1 XR-encoding gene open reading frame (SEQ ID NO:41).

FIG. 47. WP1 XDH-encoding gene open reading frame (SEQ ID NO:43).

DETAILED DESCRIPTION OF THE INVENTION

I. Overview

Figure 1:
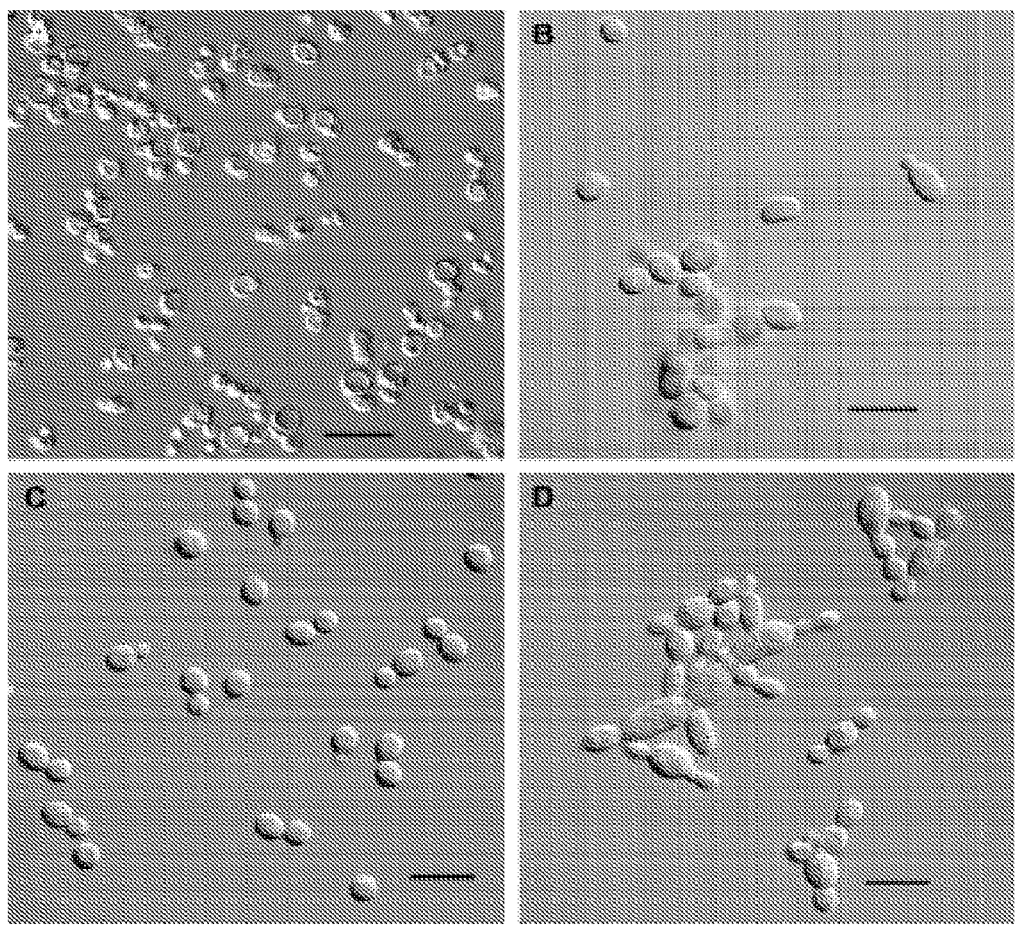
FIG. 1. Photomicrographs of the yeast strains (scale bar equal to 25 mm for A and 10 mm for B, C, D). (A) WP1; (B) PTD2; (C) PTD3; (D) *Rhodotorula glutinis*.
Figure 2:
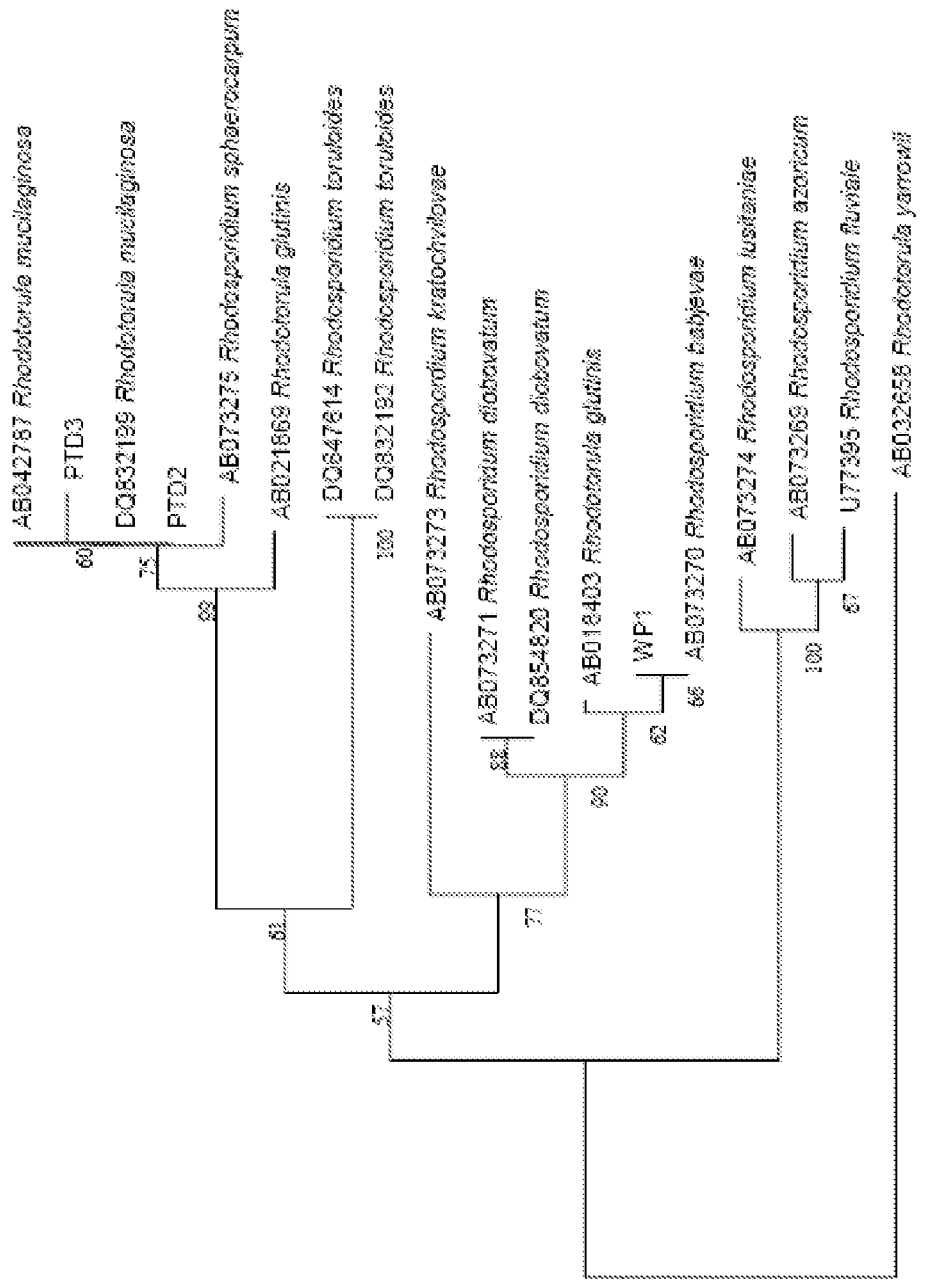
FIG. 2. Phylogenetic tree showing relatedness among 18S gene sequences of yeast strains. The tree was constructed with a total of 952 positions using a neighbor joining distance matrix. Evolutionary distances were computed using the Jukes-Cantor method. Bootstrap values (1000 tree interactions) are indicated at the nodes.
Figure 3:
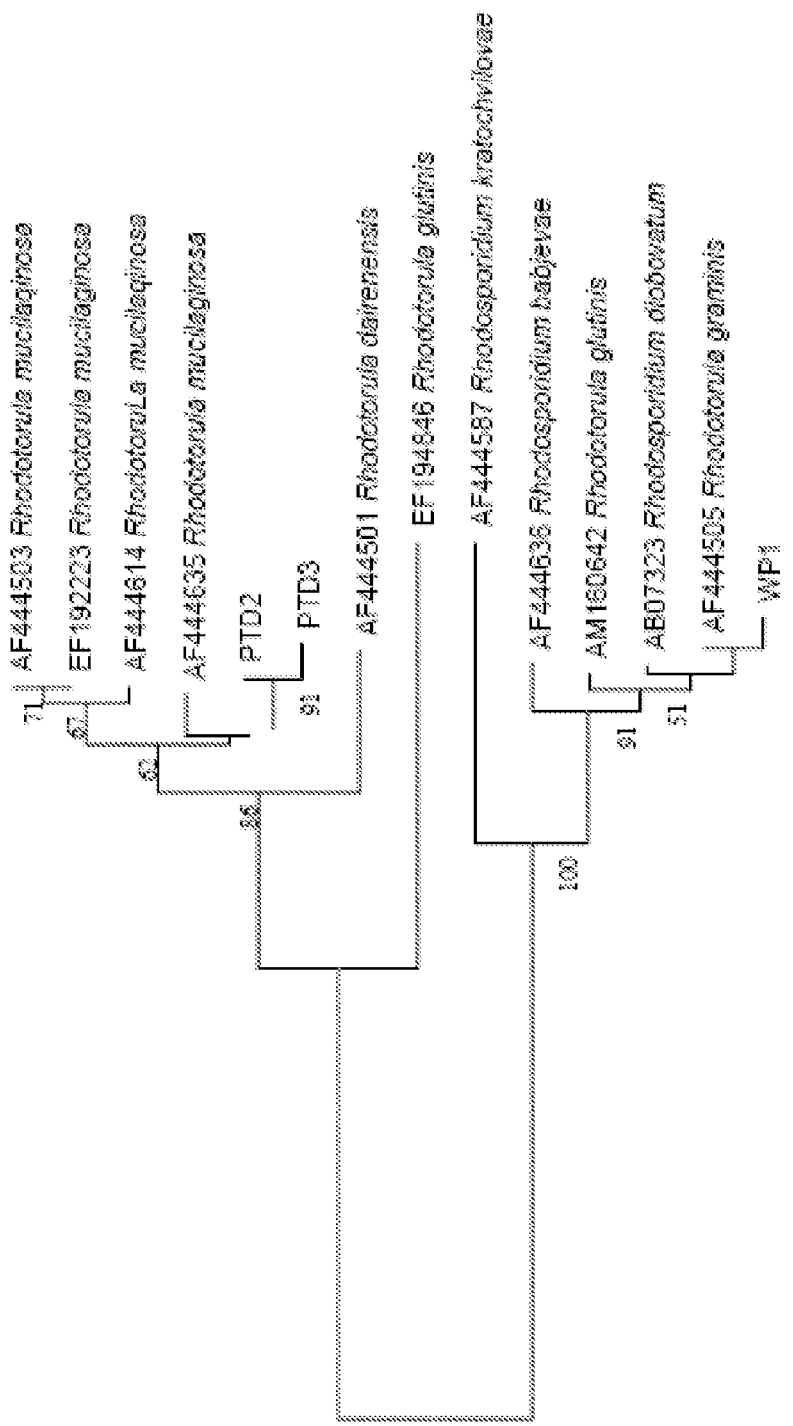
FIG. 3. Phylogenetic reconstruction based on ITS1-5.8S-ITS2 sequences of yeast strains. The tree was constructed with a total of 583 positions using a neighbor-joining distance matrix. Evolutionary distances were computed using the Jukes-Cantor method. Bootstrap values (1000 tree interactions) are indicated at the nodes.
Figure 4:
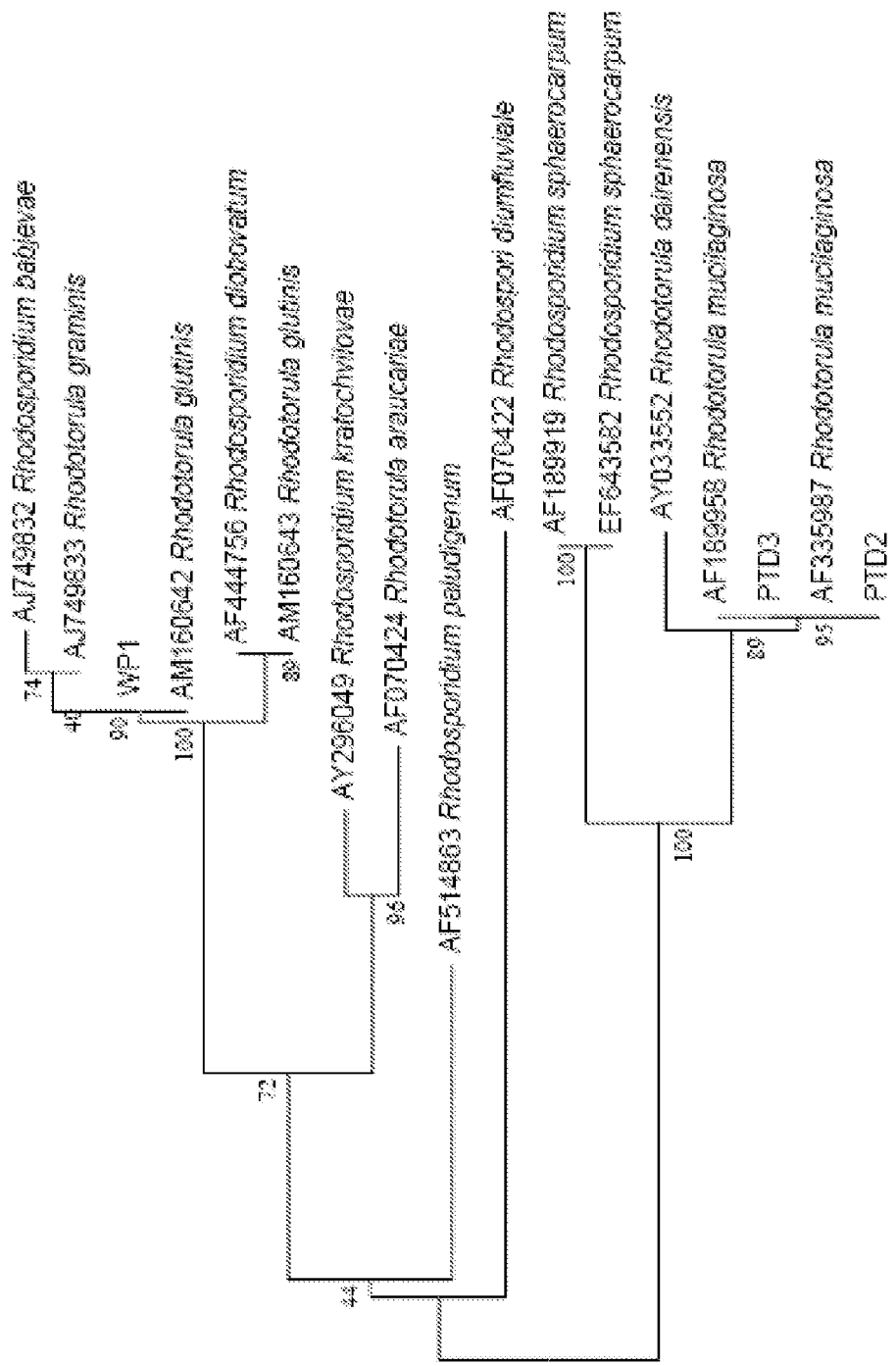
FIG. 4. Phylogenetic tree showing relatedness among large subunit gene D1/D2 region sequences of yeast strains. The tree was constructed with a total of 586 positions using a neighbor joining distance matrix. Evolutionary distances were computed using the Jukes-Cantor method. Bootstrap values (1000 tree interactions) are indicated at the nodes.
Figure 5:
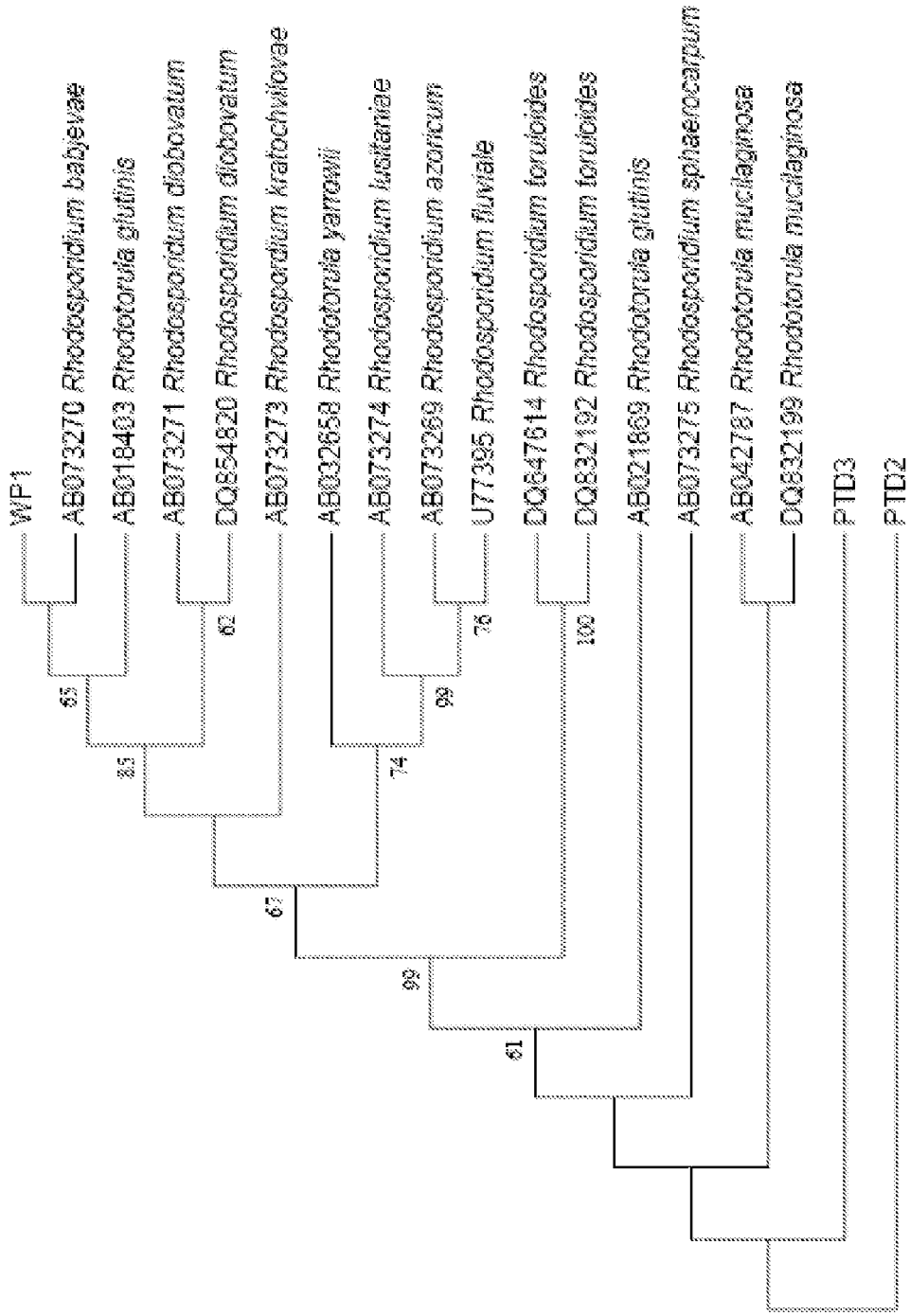
FIG. 5. Phylogenetic tree showing relatedness among 18S gene sequences of yeast strains. The tree was constructed with a total of 952 positions using a Maximum Parsimony method. Bootstrap values (1000 tree interactions) are indicated at the nodes.
Figure 6:
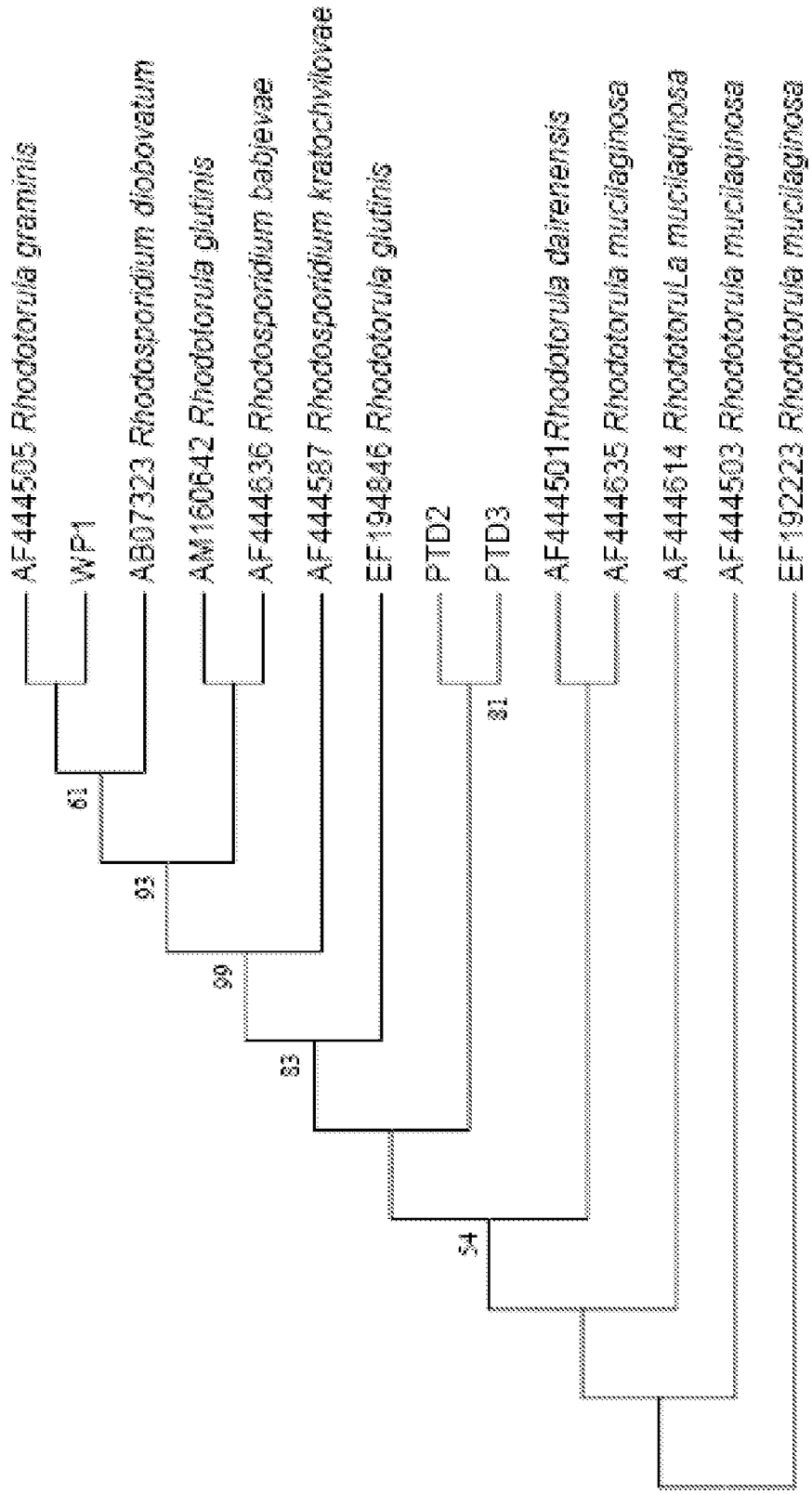
FIG. 6. Phylogenetic reconstruction based on ITS1-5.8S-ITS2 sequences of yeast strains. The tree was constructed with a total of 583 positions using a Maximum Parsimony. Bootstrap values (1000 tree interactions) are indicated at the nodes.
Figure 7:
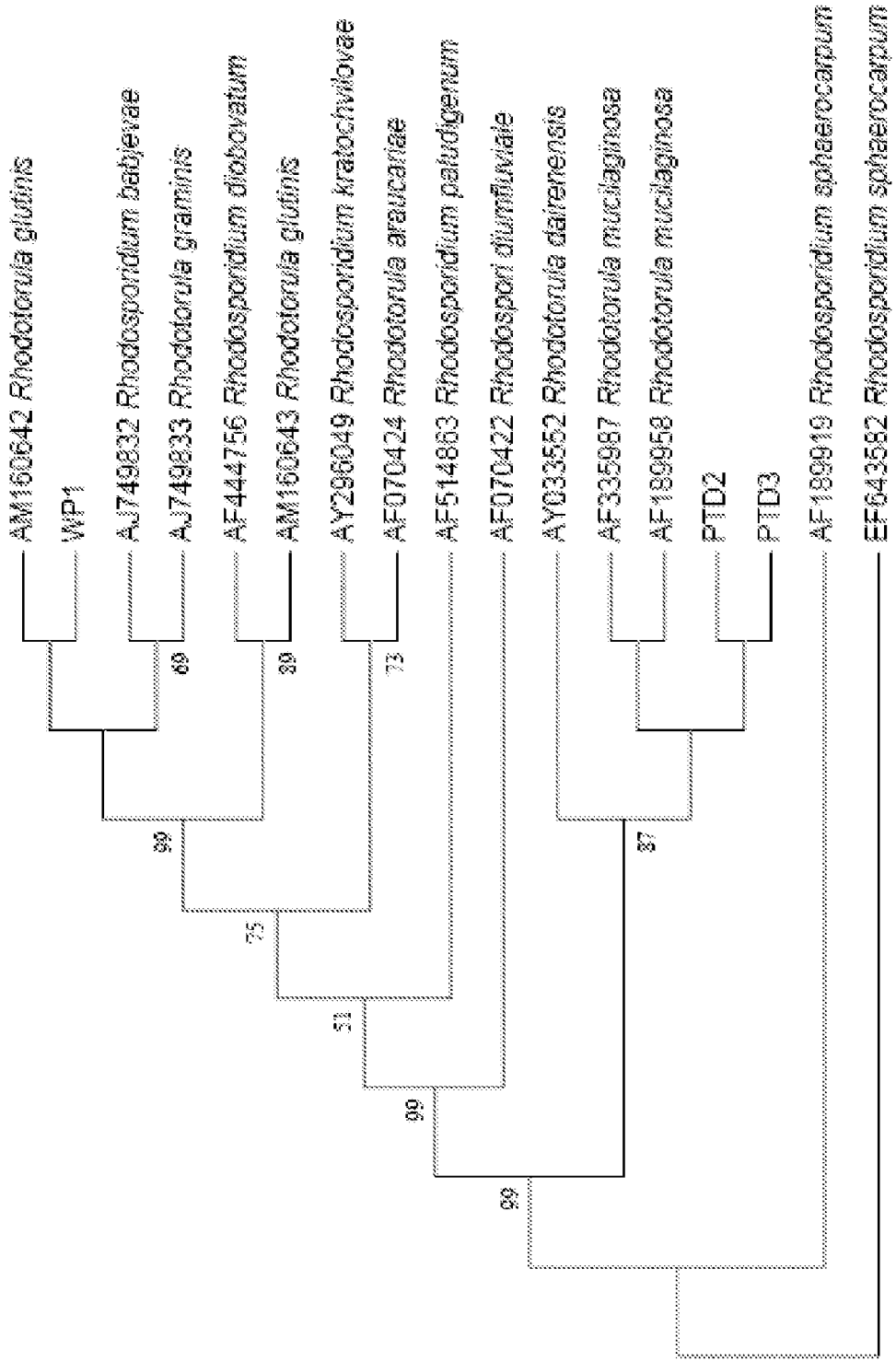
FIG. 7. Phylogenetic tree showing relatedness among large subunit gene D1/D2 region sequences of yeast strains. The tree was constructed with a total of 586 positions using a Maximum Parsimony method. Bootstrap values (1000 tree interactions) are indicated at the nodes.

In one aspect, the present invention provides novel endophytic yeast strains, including WP1 and PTD3, isolated from within the stems of poplar (*Populus*) trees, which were genetically characterized with respect to their xylose metabolism genes. These strains, belonging to species *Rhodotorula graminis* and *R. mucilaginosa*, respectively, utilize both hexose and pentose sugars, including the common plant pentose sugar, D-xylose. In another aspect, the present invention provides the xylose reductase gene (XYL1) and xylitol dehydrogenase gene (XYL2) from these yeast strains, which were cloned and characterized. The derived amino acid sequences of xylose reductase (XR) and xylose dehydrogenase (XDH) are 32%~41% homologous to those of *Pichia stipitis* and *Candida*. Spp., species known to utilize xylose. The derived XR and XDH sequences of WP1 and PTD3 have higher homology (73% and 69% identity) with each other. WP1 and PTD3 were grown in single sugar and mixed sugar medium to analyze the XYL1 and XYL2 gene regulation mechanisms. These results revealed that for both strains, the gene expression is induced by D-xylose, and that the expression was not repressed by glucose in the presence of xylose in PTD3.

Notably, the gene expression of the WP1 and PTD3 is unique in these endophytic yeast strains. They are expressed in response to xylose even when glucose is present. In contrast, in other species, these xylose metabolism genes are shut off when glucose is present, preventing simultaneous use of both 5-carbon and 6-carbon sugars.

Lignocellulosic material containing cellulose, hemicellulose, and lignin is an abundant renewable organic resource that can be used for the production of energy and biochemicals. The conversion of both the cellulose and hemicellulose fractions for production of biochemicals is being studied intensively. Between 23% to 40% of the lignocellulosic biomass consists of hemicellulose, the main component being xylose in most hardwoods and annual plants (Lee et al. 1979). Whereas the fermentation of glucose can be carried out efficiently by the common brewer's yeast (*Saccharomyces cerevisiae*), the bioconversion of the pentose fraction (xylose and arabinose) presents a challenge since it is not metabolized by this species. In the past decades, numerous studies have been carried out on various aspects of D-xylose bioconversion (Du Preez 1994; Winkelhausen and Kuzmanova 1998).

D-xylose can be utilized by bacteria, yeasts and fungi (Jeffries 1983) using different pathways. In one pathway, D-xylose can be directly converted to D-xylulose by xylose isomerase (Aristidou and Penttila 2000) without the participation of cofactors. In some yeasts and fungi, conversion of D-xylose to D-xylulose is carried out more often by two enzymatic steps. First, D-xylose is reduced by a NADPH/ NADH-linked xylose reductase (XR) to xylitol, followed by oxidation of xylitol to xylulose by an NAD-linked xylitol dehydrogenase (XDH) (Bruinenberg and van Dijken 1983). D-xylulose is subsequently phosphorylated to D-xylulose-5-phosphate by D-xylulokinase before it enters the pentose phosphate, Embden-Meyerhof, and phosphoketolase pathways (Skoog and Hahn-Hagerdal 1988).

The two major chemicals of interest that can be produced from D-xylose by yeasts are ethanol and xylitol. It is known that under normal growth conditions, some pentose-fermenting yeasts (e.g. *Pichia stipitis*) produce mostly ethanol (Du Preez 1994; Schneider 1989); while others (e.g. *Candida guilliermondii, Candida tropicalis*) produce mainly xylitol as the end products (Barbosa et al. 1988; Gong et al. 1981). As an intermediate metabolite, xylitol is widely applied in food and pharmaceutical industries because of its equivalent sweetness to sucrose and high negative heat of solution (Borges 1991; Passon 1993), its anticariogenic and anti-infection effects (Pizzo et al. 2000; Sakai et al. 1996; Brown et al. 2004), and independent metabolism of insulin, therefore making it useful for diabetic patients (Salminen et al. 1989). Among the xylose-fermenting yeast, the genus *Candida* is one of the most efficient xylitol producers (Meyrial et al. 1991). Ojama demonstrated that *C. guilliermondii* VTT-C-71006 is an efficient xylitol producer. A xylitol yield of 0.74 g/g xylose was obtained within 50 hours at an initial D-xylose concentration of 100 g/l (Ojama 1994).

The pink yeast strains WP1 (*Rhodotorula graminis*) and PTD3 (*Rhodotorula mucilaginosa*) provided in one aspect of the present invention are remarkable for their good performance in xylitol production (approximately 67% conversion) and sugar metabolism in the presence of several common fermentation inhibitors (Vajzovic, A., unpublished). So far, investigation of xylitol production by yeasts has been limited to *Candida* and *Pichia* species and studies of D-xylose metabolism in *Rhodotorula* spp. were barely reported. Although XR and XDH activities were detected in *Rhodosporidium toruloides* (the teleomorph of *Rhodotorula glutinis*) (Freer et al. 1997), none of the genes encoding XR and XDH were cloned from the *Rhodotorula* genus. The present invention provides, among other aspects, the first report that describes the cloning and characterization of the XR-encoding gene (XYL1) and XDH-encoding gene (XYL2) from both *Rhodotorula graminis* and *Rhodotorula mucilaginosa* yeast strains.

In one aspect, the present invention provides XR and XDH encoding genes, which were cloned from *Rhodotorula graminis* strain WP1. The expression of the two genes was verified by RT-PCR. This study shows that D-xylose is a good inducer of XR and XDH in both strains. This is similar to the trend found with *Candida guilliermondii* (Sugai and Delgenes 1995) and *Pichia stipitis* (Bichio et al. 1988). Furthermore, a novel characteristic of lack of inhibition by glucose for these genes is also demonstrated.

Notably, the XI (xylose isomerase)-encoding gene was not found in the WP1 genome sequence provided by the JGI. Thus WP1 likely utilizes the two-step redox pathway in D-xylose metabolism as in other yeasts. However, the alignments showed that the XR and XDH sequences have low homology (32%~41% identities) with other XRs and XDHs from *Candida* spp. and *Pichia stipitis* yeasts. In addition, the WP1 XR and XDH-encoding genes have multiple introns and the exon/intron structures are more complicated and advanced than the homologous genes in *Pichia stipitis* and *Candida* spp. These differences might introduce greater variability of protein sequences translated from a single gene and might have an impact on enhancing the expression of the XR and XDH genes (Smith and Lee 2008; Lin et al. 2010). From the macro perspective, the gene differences suggest that there could be long evolution distances between WP1 and *Pichia stipitis* and *Candida* spp. and this might lead to some other differences in the xylose metabolism pathway between these yeasts.

The present study of gene expression levels in xylose and glucose media shows that the expression of WP1 XR and XDH-encoding genes were induced by xylose. The two genes in WP1 were expressed to low levels while grown in glucose medium. Additionally, the expression level of the XDH-encoding gene (XYL1) in WP1 was higher than that of the XR-encoding gene (XYL2).

In a related aspect, the present invention also provides full-length XR and XDH encoding genes, which were cloned from *Rhodotorula mucilaginosa* strain PTD3. The expression of these two genes was also verified by RT-PCR. Sequence alignment results show that the XR and XDH sequences also have low homology (37%~41% identities) with other XRs and XDHs from *Candida* spp. and *Pichia stipitis* yeasts. Since the genome sequence of PTD3 is not available, the exon/intron structures of the two genes was not determined. However, based on the high homology (73% and 69% identity for XR, XDH) with WP1, it is likely that the gene structures of PTD3 may be more like that of WP1 and that these two endophytic yeasts of poplar trees may metabolize D-xylose using the same pathway.

Like in WP1, the expression of PTD3 XR and XDH-encoding genes was also induced by xylose. The two genes in PTD3 were expressed to low levels while grown in glucose medium. As in WP1, the expression level of the XDH-encoding gene (XYL1) in PTD3 was higher than that of the XR-encoding gene (XYL2).

Since PTD3 grew better in D-xylose medium compared to WP1, one hypothesis to explain this difference is that PTD3 may produce the enzymes involved in xylose metabolism at higher levels than does WP1. This gene expression study verified that both the XR and XDH-encoding gene expression levels were much higher in PTD3 than in WP1, thus supporting this hypothesis. Further study into the resulting protein levels and also the xylose uptake mechanisms for these yeast strains is yet to be explored.

In another aspect of the invention, single sugars and mixed sugars were investigated to analyze their potential to induce XR and XDH-encoding gene expressions in both WP1 and PTD3. For many yeasts like *Saccharomyces cerevisiae*, *Pichia stipitis* and *Candida* spp., D-glucose is the preferred substrate for growth and fermentation when both D-glucose and D-xylose are present in the medium. The genes for xylose assimilation (XYL1, XYL2) were not expressed in *Pichia stipitis* in the presence of glucose in the medium (Jeffries et al. 2007). The present study shows that in both WP1 and PTD3 yeast strains, the two genes were still expressed in response to xylose in the presence of glucose in the medium. Furthermore, the band quantities of RT-PCR in single sugar (xylose) and mixed sugar (glucose+xylose) revealed that the two genes were not repressed by glucose in PTD3 while they were slightly suppressed in WP1. These are significant results because xylose reductase and xylitol dehydrogenase are pivotal for growth and xylitol formation during xylose metabolism. And the high-level expression of both genes in the mixed sugars of xylose and glucose will largely increase the xylitol yield in mixed sugars from real hydrolytes and will contribute to optimizing fermentation conditions of lignocellulosic biomass. In addition, better understanding of the regulation mechanism of these genes, together with identification of the XR and XDH-encoding genes as well as the xylose uptake genes will help determine the strategies for genetic engineering of industry strains such as *S. cerevisiae* for further improvement of productivity. Accordingly, the present invention provides, in one aspect, recombinant yeast cells and strains harboring a heterologous XR and/or XDH-encoding gene from the WP1 or PTD3 strain, or a highly similar sequence.

In one aspect, the present invention provides a biotechnological process for the production of a sugar alcohol or polyol, using the endophytic yeast provided herein. One novel yeast strain, provided herein, was isolated from poplar trees and has several unique properties. In one embodiment, the invention provides a PTD3 yeast strain isolated from a hybrid poplar tree or a giant reed.

Pretreatment of lignocellulosic biomass can produce fermentation inhibitors such as furfural, 5-HMF, and acetic acid. These compounds can decrease the ethanol yields from sugars. Provided herein are isolated yeast strains that have a high tolerance for such inhibitors. A systematic study of the effect of furfural, 5-HMF, and acetic acid concentration on the fermentation of glucose and xylose to ethanol and xylitol respectively by PTD3, a novel, genetically unmodified yeast is provided herein.

The influence of furfural in different concentrations (from 1 to 5 g/L) on the growth of PTD3 yeast under cultivation in synthetic nutrient media has been studied. The yeast provided herein grow well in presence of furfural and showed resemblance in growth and fermentative pattern with controls. Ethanol yield achieved from glucose and xylitol, using the yeast strains of the invention, were of 90% of theoretical yield for ethanol and 70% of the theoretical yield for xylitol. Ethanol yields from glucose were not influenced by presence of furfural. However, xylitol biosynthesis was affected by the presence of furfural in the fermentation media. The effects of higher concentrations of furfural (10 and 20 g/L) on the ethanol and xylitol yields are presented herein, as well as the effects of 5-HMF and acetic acid.

Up to date, there is no reported microorganism that is capable of utilizing both, hexose and pentose sugars at the same time, without being genetically modified or co-cultured. A genetically unmodified yeast which is capable of rapid assimilation and catabolism of five and six carbon sugars (arabinose, xylose, galactose, glucose and mannose) is provided herein. This yeast (PTD3) was shown not to be subject to hexose-mediated repression during mixed sugars fermentation. PTD3 produced ethanol of 82% of theoretical during fermentation of glucose, mannose and galactose. It produced considerable amount of xylitol of 96.1% of theoretical when xylose was present in the fermentation media. The high ethanol and xylitol were obtained without media, aeration, temperature and pH optimization.

The novel yeast provided herein also have a high tolerance of inhibitors, including without limitation, furfurals, 5-HMF, and acetic acid, during biological production of ethanol and xylitol. PTD3 can effectively ferment five and six carbon sugars present in hydrolysates from different cellulosic biomass, for example, steam pretreated switchgrass, hybrid poplar, and sugar cane bagasse, to ethanol and xylitol.

II. Endophytic Yeast Strains and Cultures Thereof

In one embodiment of the invention, novel endophytic yeast strains capable of metabolizing both pentose and hexose sugars are provided. In certain embodiments, these yeast strains are most closely related to *Rhodotorula graminis* or *Rhodotorula mucilaginosa* species. In a particular embodiment, the novel strains of the invention are selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. The strain *Rhodotorula graminis* strain WP1 has the A.T.C.C. designation number PTA-120764, having been deposited on Dec. 11, 2013. The strain *Rhodotorula mucilaginosa* strain PTD2 has the A.T.C.C. designation number PTA-120763, having been deposited on Dec. 11, 2013. The strain *Rhodotorula mucilaginosa* strain PTD3 has the A.T.C.C. designation number PTA-120762, having been deposited on Dec. 11, 2013. The strain *Rhodotorula mucilaginosa* strain Ad1 has the A.T.C.C. designation number PTA-120761, having been deposited on Dec. 11, 2013. In one embodiment of the invention, the novel endophytic yeast strains contain an rRNA gene sequence that is selected from any one of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15.

Statement of Deposit

Biologically pure cultures of the endophytic yeast strains Ad1, PTD2, PTD3, and WP1 described herein were deposited Dec. 11, 2013, under terms of the Budapest Treaty with the American Type Culture Collection (ATCC®) (10801 University Boulevard, Manassas, Va. 20110 USA), and given the patent deposit designation numbers PTA-120761, PTA-120763, PTA-120762, and PTA-120764, respectively. The microorganism deposit was made under the provisions of the "Budapest Treaty on the International Recognition of the Deposit of Microorganisms for the Purposes of Patent Procedure." All restrictions on the availability to the public of these deposited microorganisms will be irrevocably removed upon issuance of a United States patent based on this application. For the purposes of this disclosure, any isolate having the identifying characteristics of strains PTA-120761, PTA-120763, PTA-120762, and PTA-120764, including subcultures and variants thereof having the identifying characteristics and activity as described herein, are included.

In another embodiment, the present invention provides cultures of novel endophytic yeast strains capable of metabolizing both pentose and hexose sugars. In some embodiments, the cultures of the invention comprise a biologically pure culture of an endophytic yeast strain, while in other embodiments, the cultures of the invention may comprise more than one strain of yeast. In specific embodiments, the cultures of the invention may comprise a yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the cultures of the invention comprise one or more yeast strain that is identified by an rRNA gene sequence selected from the group consisting of SEQ ID NOS:7 to 18.

The novel endophytic yeast strains and cultures of the present invention may be useful in the fermentative production of bioethanol, xylitol, and other biotechnological manufacturing products. In a particular embodiment, the novel strains of the invention are useful for the fermentation of mixtures of pentose and hexose sugars. In certain embodiments, the strains and cultures of the invention are useful for the fermentation of biomass that has been pretreated to yield a mixture of pentose and hexose sugars. For example, lignocellulosic biomass such as wood or wood residuals (e.g., saw mill or paper mill discards), municipal paper waste (e.g., newspapers), agricultural residuals (e.g., corn stover, sugarcane bagasse), tall woody grasses, and the like. Methods of pretreating lignocellulosic biomass for yeast fermentation are well known in the art and include both acid hydrolysis and enzymatic hydrolysis. For review, see Lange J. P., *Biofuels, Bioproducts, and Biorefining* 1(1):39-48 (2007); Jorgensen H. et al., *Biofuels, Bioproducts, and Biorefining* 1(2):119-134 (2007); Wyman C. E. et al., Bioresour Technol. 2005 December; 96(18):2026-32; and Wyman C. E. et al., Bioresour Technol. 2005 December; 96(18):1959-66.

In another embodiment, the endophytic yeast strains and cultures of the present invention may be useful for fixing atmospheric nitrogen. In a particular embodiment, the novel strains of the invention are useful for fertilizing a crop in the presence or absence of a traditional chemical fertilizer. In one embodiment, the novel strains are useful for inoculating a crop or colonizing the soil a crop is planted in with the yeast. The soil may be colonized with the yeast prior to planting the crop, for example before, during, or after tilling the soil in preparation for planning the crop. In other embodiments, the soil may be colonized with the yeast after the crop has been planted.

In some embodiments, the cultures of the invention useful for nitrogen fixation and/or fertilization of a crop comprise a biologically pure culture of an endophytic yeast strain, while in other embodiments, the cultures of the invention may comprise more than one strain of yeast. In specific embodiments, the cultures of the invention may comprise a yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the cultures of the invention comprise one or more yeast strain that is identified by an rRNA gene sequence selected from the group consisting of SEQ ID NOS:7 to 18.

III. Methods for Producing Ethanol, Sugar Alcohols, and Polyols

In one embodiment, the present invention provides novel methods for producing ethanol comprising fermenting a carbon source with an endophytic strain of yeast. In certain embodiments, the endophytic yeast is capable of metabolizing both pentose and hexose sugars. In a specific embodiment, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15.

In another embodiment of the invention, methods of producing xylitol are provided. In one embodiment, the method comprises fermenting a carbon source with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15.

The carbon sources used in the methods of the invention, may comprise a pentose sugar or sugar alcohol, a hexose sugar or sugar alcohol, or a combination thereof. In particular embodiments, the carbon source is selected from the group consisting of glucose, glycerol, calcium 2-keto-gluconate, arabinose, xylose, adonitol, xylitol, galactose, inositol, sorbitol, methyl-α-glucopyranoside, N-acetyl-glucosamine, cellobiose, lactose, maltose, sucrose, trehalose, melezitose, raffinose, and combinations thereof. In a particular embodiment, the carbon source is xylitol, glucose, or a combination of sugars containing xylitol, glucose, or both. In other embodiments, the carbon source may comprises biomass that has been hydrolytically pre-treated. For example, lignocellulosic biomass such as wood or wood residuals (saw mill or paper mill discards), municipal paper waste, agricultural residuals (corn stover, sugarcane bagasse), tall woody grasses, and the like. The carbon sources used in the methods of the invention are not limited to those listed above.

In related embodiments, the present invention provides methods of producing mixtures of xylitol and ethanol. In one embodiment, the method comprises fermenting a carbon source with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15. In one particular embodiment, the present invention provides methods of producing mixtures of xylitol and ethanol.

In certain embodiments, the methods of the invention further comprise purifying one or more of xylitol, ethanol, or both after production. Methods of purifying xylitol from reaction mixtures are well known in the art and include, without limitation, distillation, crystallization, chromatography, combinations thereof, and the like. For example, U.S. Pat. No. 6,538,133 describes chromatographic procedures of purifying xylitol from cultures of xylitol-producing microorganisms. Rivas et al., *J. Agric. Food Chem.* 2006, 54(12): 4430-4435, describe a process of purifying xylitol obtained by fermentation of corncob hydrolysates by crystallization. Methods of distilling ethanol are also well known in the art. For example, U.S. Pat. No. 7,297,236 describe process arrangements for distilling fuel grade ethanol. Methods of simultaneously producing xylitol and ethanol are well known in the art, for example see U.S. Pat. No. 7,109,055.

In certain embodiments, the methods of the present invention comprise the steps of producing a mixture of xylitol and ethanol and purifying said ethanol and xylitol from the residual material. In one particular embodiment, the mixture of xylitol and ethanol is first distilled to yield substantially pure ethanol and then xylitol is purified from the distillation residuals. In one embodiment, the method comprises fermenting a carbon source with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15.

In yet other embodiments of the invention, methods are provided for the production of xylitol comprising the steps of hydrolytically treating a source of biomass to produce a mixture of pentose and hexose sugars, separating a first stream comprising xylose from a second stream comprising glucose, and fermenting said first stream with an endophytic strain of yeast capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In a particular embodiment, an endophytic yeast strain of the invention may have an 18S rRNA gene sequence selected from SEQ ID NOS:7 to 9 or 15 to 16, an ITS rRNA gene sequence selected from SEQ ID NOS:10 to 12, or a 26S D1/D2 rRNA gene sequence selected from SEQ ID NOS:13 to 15.

In some embodiments, the above method further comprises fermenting said second stream with a yeast capable of producing ethanol. In a particular embodiment, the yeast is an endophytic strain capable of metabolizing both pentose and hexose sugars. In certain embodiments, the endophytic strain is selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In other embodiments, the endophytic strain is identified by an rRNA gene sequence selected from the group consisting of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15. In some embodiments, the yeast strain used to ferment said first stream is the same as the yeast strain used to ferment said second stream. In yet other embodiments, the yeast strains are different.

IV. Recombinant Yeast Strains and Methods of Use Thereof

In another aspect, the invention provides recombinant yeast strains capable of fermenting both pentose and hexose sugars. In certain embodiments, these strains harbor a heterologous gene sequence from an endophytic yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1, wherein said strain is identified by an rRNA gene sequence selected from any one of SEQ ID NOS:7 to 18.

In one embodiment, the heterologous gene sequence encodes for a xylose reductase (XR) protein or a xylose dehydrogenase (XDH) protein. In certain embodiments, the heterologous gene sequence has at least 85% sequence identity with an XYL1 or XYL2 gene sequence or coding sequence from an endophytic yeast provided herein. In certain embodiments, the heterologous gene sequence has at least 85% sequence identity to a nucleotide sequence selected from the group consisting of SEQ ID NO:41, SEQ ID NO:43, SEQ ID NO:45, and SEQ ID NO:47. In other embodiments, the heterologous gene sequence may have at least about 85% identity, or at least about 86%, 87%, 88%, 89%, 90%, 91%, 92%, 93%, 94%, 95%, 96%, 97%, 98%, 99% or higher sequence identity to an XYL1 or XYL2 gene sequence or coding sequence provided herein. In certain embodiments, the heterologous gene sequence may further comprise one or more introns.

In one embodiment, the heterologous gene sequence encodes for a xylose reductase (XR) protein or a xylose dehydrogenase (XDH) protein. In certain embodiments, the xylose reductase protein is from the WP1 or the PTD3 stain. In a particular embodiment, the heterologous gene sequence encodes for a polypeptide having at least about 85%, or at least about 86%, 87%, 88%, 89%, 90%, 91%, 92%, 93%, 94%, 95%, 96%, 97%, 98%, 99% or higher sequence identity to an amino acid sequence selected form SEQ ID NO:42, SEQ ID NO:44, SEQ ID NO:46, and SEQ ID NO:48.

In certain embodiments, the heterologous gene sequence may be cloned into a microbial genome, for example a bacterial or yeast chromosome, or may comprise an expression vector, a recombinant or artificial microbial chromosome, for example a bacterial (BAC) or yeast (YAC) chromosome, a bacterial plasmid, a yeast plasmid, a recombinant bacteria phage, a recombinant viral vector, a mammalian expression vector, a baculovirus vector. In yet other embodiments, the heterologous gene sequence may encode for a fusion protein. In another embodiment, the heterologous gene sequence may encode for a tagged protein, such as a tagged XR or XDH protein.

In certain embodiments, the recombinant yeast strains may be a *Saccharomyces*, a *Schizosaccharomyces*, a *Candida*, a *Zygosaccharomyces*, a *Brettanomyces*, a *Torulaspora*, an *Ascobotryozyma*, a *Citeromyces*, a *Debaryomyces*, an *Eremothecium*, a *Issatchenkia*, a *Kazachstania*, a *Kluyveromyces*, a *Kodamaea*, a *Kregervanrija*, a *Kuraishia*, a *Lachancea*, a *Lodderomyces*, a *Nakaseomyces*, a *Pachysolen*, a *Pichia*, a *Saturnispora*, a *Tetrapisispora*, a *Torulaspora*, a *Vanderwaltozyma*, a *Williopsis*, and the like. In a particular embodiment, the recombinant yeast is a *Saccharomyces*, a *Schizosaccharomyces*, a *Candida*, a *Zygosaccharomyces*, or a *Brettanomyces*. In one embodiment, the strain is *Saccharomyces cerevisiae*. In a related aspect, biologically pure cultures of the recombinant yeast strains are provided.

In another aspect, the invention provides methods of fermenting a carbon source with a recombinant yeast strain provided herein. In certain embodiments, the methods comprise culturing a recombinant yeast of the invention in the absence of a supplemental nitrogen source, for example ammonium or nitrate.

In a related aspect, methods of producing ethanol are provided. In certain embodiments, the methods comprise fermenting a carbon source with a recombinant yeast strain provided herein. In certain embodiments, the methods comprise fermenting a carbon source in the absence of a supplemental nitrogen source, for example ammonium or nitrate.

In another related embodiment, methods of producing an animal feedstock are provided. In certain embodiments, the method comprises culturing a recombinant yeast of the invention in the absence of a supplemental nitrogen source, for example ammonium or nitrate. Advantageously, these methods provide an inexpensive source of animal feedstock, as the recombinant yeast provided herein are capable of performing nitrogen fixation and thus can be grown in culture medium that is not supplemented with a nitrogen source The yeast of the invention may be genetically modified to further enhance the metabolism of particular pentose and or hexose sugars. Exogenous genes encoding for any one of a number of enzymes may be introduced and expressed in an endophytic yeast used in any one of the methods of the invention. Non-limiting examples of exogenous enzymes that may be expressed in the yeast of the invention include, xylose isomerases, xylose reductases, xylose dehydrogenases, NAD-dependent glutamate dehydrogenases, malic enzymes, xylulokinases, phosphoacetyltransferase, aldehyde dehydrogenase, phosphoketolase, and the like. Examples of the metabolic engineering of yeasts can be found, for example, in Nevoigt, *Microbiology and Molecular Biology Reviews* 2008 72(3):379-412.

In certain embodiments, the methods of the invention comprise optimizing the culture medium in order to maximize the production of a particular product, such as ethanol or xylitol.

In another embodiment, the recombinant yeast strains and cultures provided herein may be useful for fixing atmospheric nitrogen. In a particular embodiment, the novel strains are useful for fertilizing a crop in the presence or absence of a traditional chemical fertilizer. In one embodiment, the novel strains are useful for inoculating a crop or colonizing the soil a crop is planted in with the yeast. The soil may be colonized with the yeast prior to planting the crop, for example before, during, or after tilling the soil in preparation for planning the crop. In other embodiments, the soil may be colonized with the yeast after the crop has been planted.

V. Xylose Reductase and Xylose Dehydrogenase Polynucleotides and Polypeptides

In one aspect, the present invention provides xylose reductase (XR) polypeptides and xylose dehydrogenase (XDH) polypeptides. In certain embodiments, XR and XDH polypeptides are from a yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In some embodiments, the strain is identified by an rRNA gene sequence selected from any one of SEQ ID NOS:7 to 18. In one embodiment, the polypeptide has an amino acid sequence that is at least about 85% identical to a an amino acid sequence selected form SEQ ID NO:42, SEQ ID NO:44, SEQ ID NO:46, and SEQ ID NO:48. In other embodiments, the amino acid sequence of the protein has at least about 85%, or at least about 86%, 87%, 88%, 89%, 90%, 91%, 92%, 93%, 94%, 95%, 96%, 97%, 98%, 99% or higher sequence identity to an amino acid sequence selected form SEQ ID NO:42, SEQ ID NO:44, SEQ ID NO:46, and SEQ ID NO:48. In one embodiment, the invention provides a polypeptide encoded by the nucleotide sequence found in FIG. 44, FIG. 45, FIG. 46, or FIG. 47. In other embodiments, the amino acid sequence of the protein has at least about 85%, or at least about 86%, 87%, 88%, 89%, 90%, 91%, 92%, 93%, 94%, 95%, 96%, 97%, 98%, 99% or higher sequence identity to an amino acid sequence encoded by the nucleotide sequence found in FIG. 44, FIG. 45, FIG. 46, or FIG. 47.

In a related aspect, the present invention provides isolated and/or recombinant polynucleotides encoding for a xylose reductase (XR) polypeptide and/or a xylose dehydrogenase (XDH) polypeptide. In certain embodiments, XR and XDH polypeptides are from a yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In some embodiments, the strain is identified by an rRNA gene sequence selected from any one of SEQ ID NOS:7 to 18. In one embodiment, the polypeptide encoded by a polynucleotide of the invention has an amino acid sequence that is at least about 85% identical to a an amino acid sequence selected form SEQ ID NO:42, SEQ ID NO:44, SEQ ID NO:46, and SEQ ID NO:48. In other embodiments, the amino acid sequence of a polypeptide encoded by a polynucleotide of the invention has at least about 85%, or at least about 86%, 87%, 88%, 89%, 90%, 91%, 92%, 93%, 94%, 95%, 96%, 97%, 98%, 99% or higher sequence identity to an amino acid sequence selected form SEQ ID NO:42, SEQ ID NO:44, SEQ ID NO:46, and SEQ ID NO:48. In one embodiment, the invention provides a polynucleotide that encodes for a polypeptide encoded by the nucleotide sequence found in FIG. 44, FIG. 45, FIG. 46, or FIG. 47. In other embodiments, the invention provides a polynucleotide that encodes for a polypeptide with an amino acid sequence that has at least about 85%, or at least about 86%, 87%, 88%, 89%, 90%, 91%, 92%, 93%, 94%, 95%, 96%, 97%, 98%, 99% or higher sequence identity to an amino acid sequence encoded by the nucleotide sequence found in FIG. 44, FIG. 45, FIG. 46, or FIG. 47.

In a related embodiment, the present invention provides isolated and/or recombinant polynucleotides comprising an XYL1 and/or XYL2 gene or coding sequence from an endophytic yeast provided herein. In certain embodiments, the polynucleotide comprises a nucleotide sequence that has at least 85% sequence identity to a nucleotide sequence selected from the group consisting of SEQ ID NO:41, SEQ ID NO:43, SEQ ID NO:45, and SEQ ID NO:47. In other embodiments, the polynucleotide comprises a nucleotide sequence that has at least about 85% identity, or at least about 86%, 87%, 88%, 89%, 90%, 91%, 92%, 93%, 94%, 95%, 96%, 97%, 98%, 99% or higher sequence identity to an XYL1 or XYL2 gene sequence or coding sequence provided herein, for example, SEQ ID NO:41, SEQ ID NO:43, SEQ ID NO:45, and SEQ ID NO:47. In certain embodiments, the polynucleotide may further comprise an intron or intronic sequence. In one embodiment, the polynucleotide comprising an XYL1 and/or XYL2 gene or coding sequence comprises a nucleotide sequence found in FIG. 44, FIG. 45, FIG. 46, or FIG. 47. In certain embodiments, the polynucleotides of the present invention may further comprise one or more introns.

In one embodiment, the polynucleotide sequence encodes for a xylose reductase (XR) protein or a xylose dehydrogenase (XDH) protein. In certain embodiments, the xylose reductase protein is from the WP1 or the PTD3 stain. In a particular embodiment, the heterologous gene sequence encodes for a polypeptide having at least about 85%, or at least about 86%, 87%, 88%, 89%, 90%, 91%, 92%, 93%, 94%, 95%, 96%, 97%, 98%, 99% or higher sequence identity to an amino acid sequence selected form SEQ ID NO:42, SEQ ID NO:44, SEQ ID NO:46, and SEQ ID NO:48.

In certain embodiments, the polynucleotide may comprise a microbial genome, for example a bacterial or yeast chromosome, or may comprise an expression vector, a recombinant or artificial microbial chromosome, for example a bacterial (BAC) or yeast (YAC) chromosome, a bacterial plasmid, a yeast plasmid, a recombinant bacteria phage, a recombinant viral vector, a mammalian expression vector, a baculovirus vector. In yet other embodiments, the heterologous gene sequence may encode for a fusion protein. In another embodiment, the heterologous gene sequence may encode for a tagged protein, such as a tagged XR or XDH protein. In yet other embodiments, the polynucleotide may comprise a dual or high order expression vector that encodes for an XR and an XDH polypeptide provided herein.

VI. Methods for Biological Nitrogen Fixation and Fertilization of a Plant

In one aspect, the present invention provides methods for the biological fixation of nitrogen. In certain embodiments, the methods comprise the use of an endophytic yeast capable of fixing atmospheric nitrogen. Endophytic yeast useful for nitrogen fixation include, for example, yeast isolated from within the stems of poplar (*Populus*) trees. In certain embodiments, these yeast strains are most closely related to *Rhodotorula graminis* or *Rhodotorula mucilaginosa* species. In a particular embodiment, the novel strains of the invention are selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1. In one embodiment of the invention, the novel endophytic yeast strains contain an rRNA gene sequence that is selected from any one of SEQ ID NOS:7 to 18. In a particular embodiment, an endophytic yeast strain of the invention may have an 18S rRNA gene sequence selected from SEQ ID NOS:7 to 9 or 16 to 18, an ITS rRNA gene sequence selected from SEQ ID NOS:10 to 12, or a 26S D1/D2 rRNA gene sequence selected from SEQ ID NOS:13 to 15.

In other embodiments, strain of yeast is a recombinant yeast harboring a heterologous gene sequence from an endophytic yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1, wherein said strain is identified by an rRNA gene sequence selected from any one of SEQ ID NOS:7 to 18.

In certain embodiments, the heterologous gene sequence may be cloned into a microbial genome, for example a bacterial or yeast chromosome, or may comprise an expression vector, a recombinant or artificial microbial chromosome, for example a bacterial (BAC) or yeast (YAC) chromosome, a bacterial plasmid, a yeast plasmid, a recombinant bacteria phage, a recombinant viral vector, a mammalian expression vector, a baculovirus vector. In yet other embodiments, the heterologous gene sequence may encode for a fusion protein. In another embodiment, the heterologous gene sequence may encode for a tagged protein, such as a tagged XR or XDH protein.

In certain embodiments, the recombinant yeast strains may be a *Saccharomyces*, a *Schizosaccharomyces*, a *Candida*, a *Zygosaccharomyces*, a *Brettanomyces*, a *Torulaspora*, an *Ascobotryozyma*, a *Citeromyces*, a *Debaryomyces*, an *Eremothecium*, a *Issatchenkia*, a *Kazachstania*, a *Kluyveromyces*, a *Kodamaea*, a *Kregervanrija*, a *Kuraishia*, a *Lachancea*, a *Lodderomyces*, a *Nakaseomyces*, a *Pachysolen*, a *Pichia*, a *Saturnispora*, a *Tetrapisispora*, a *Torulaspora*, a *Vanderwaltozyma*, a *Williopsis*, and the like. In a particular embodiment, the recombinant yeast is a *Saccharomyces*, a *Schizosaccharomyces*, a *Candida*, a *Zygosaccharomyces*, or a *Brettanomyces*. In one embodiment, the strain is *Saccharomyces cerevisiae*. In a related aspect, biologically pure cultures of the recombinant yeast strains are provided.

In one embodiment, the invention provides a method for fertilizing a crop, the method comprising inoculating the crop with a strain of yeast capable of fixing nitrogen. In certain embodiments, the step of inoculating a crop comprises colonizing the soil the crop is planted in with the yeast. The soil may be colonized with the yeast prior to planting the crop, for example before, during, or after tilling the soil in preparation for planning the crop. In other embodiments, the soil may be colonized with the yeast after the crop has been planted.

The methods for fertilizing a crop with a nitrogen fixing yeast provided herein may, in certain instances, be used in conjunction or to supplement chemical fertilization or alternatively may replace chemical fertilization. For example, in certain embodiments the present invention provides a method for fertilizing a crop comprising inoculating the crop with a nitrogen fixing yeast in the absence of traditional fertilizer. In other embodiments, a method for fertilizing a crop is provided that comprises both inoculating the crop with a nitrogen fixing yeast and the use of a traditional chemical fertilizer. In certain embodiments, the amount of chemical fertilizer used may be less than would otherwise be used in the absence of a nitrogen fixing yeast, for example, at least about 5% less chemical fertilizer, or at least about 10%, 15%, 20%, 25%, 30%, 35%, 40%, 45%, 50%, 55%, 60%, 65%, 70%, 75%, 80%, 85%, 90%, 95%, or about 99% less chemical fertilizer than would otherwise be used in the absence of a nitrogen fixing yeast.

In some embodiments, the crop may be a food crop, including without limitation, sugar cane, maize, wheat, rice, potatoes, sugar beets, soybean, oil palm fruit, barley, tomato, coffee, cocoa, and the like. In certain embodiments, the crop may be a cereal grain, such as maize, rice, wheat barley, sorghum, millet, oats, rye, triticale, buckwheat, fonio, Quinoa, and the like; a vegetable, a melon, a root, a tuber, a fruit, a pulse, and the like.

In other embodiments, the crop may be a non-food crop, including without limitation, a crop grown for the production of a biofuel, such as a grass, a woody plant, a tree or shrub, such as a poplar, willow, or cottonwood, and the like; a crop used for building and or construction, such as hemp, wheat, linseed, flax, bamboo, and the like; a crop used for the production of a fiber, such as coir cotton, flax, hemp, manila hemp, papyrus, sisal, and the like; a crop used for the production of a pharmaceutical or recombinant protein, such as borage, *Echinacea, Artemisia*, tobacco, and the like; a crop used for the production of a biopolymer, such as wheat, maize, potatoes, and the like; a crop used for the production of a specialty chemical, such as lavender, oilseed rape, linseed, hemp, and the like.

DEFINITIONS

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

As used herein, the term "endophytic yeasts" refers to fungi that reproduce asexually by budding from single cells, with absent or reduced hyphal states.

As used herein, "fermentation" refers to a process of breaking down and/or reassembling an organic substance. Fermentation may be either aerobic, anaerobic, or partially anaerobic (i.e. in the presence of low oxygen content). In the case of the present invention, fermentation generally refers to the production or conversion of an alcohol or a sugar alcohol, such as ethanol or xylitol, from a sugar or mixture of sugars, including pentose and hexose sugars.

As used herein, a "biologically pure culture" refers to a culture inoculated with a single microorganism or a single strain of microorganism. Generally, the microorganism inoculated in a biologically pure culture may comprise at least about 50% of the total living mass of said culture. In certain embodiments, the microorganism may comprise at least about 50%, 55%, 60%, 65%, 70%, 75%, 80%, 85%, 90%, 95%, 96%, 97%, 98%, 99%, or all of the living mass of a biologically pure culture.

As used herein, a "lignocellulosic biomass" refers to biomass comprising cellulose, hemicellulose, and lignin. Many sources of lignocellulosic biomass are used for industrial fermentation, for example, wood residues (e.g., sawmill and paper mill discards), municipal wastes (e.g., newspaper and paper wastes), agricultural residues (e.g., corn stover, sugarcane bagasse, animal manures, cereal or flax straw, fruit, vegetable, and nut crop), dedicated energy crops (e.g., woody grasses, wood such as willow or poplar, corn, millets, clover), and the like.

The term "nucleic acid molecule" or "polynucleotide" refers to a deoxyribonucleotide or ribonucleotide polymer in either single-stranded or double-stranded form. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule may include a protein of interest, such as a protein identified as useful in the production of xylitol or ethanol. The term "recombinant host cell" refers to a cell that contains a recombinant nucleic acid molecule. As such, a recombinant host cell can express a polypeptide from a "gene" that is not found within the native (non-recombinant) form of the cell.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

Reference to a polynucleotide "encoding" a polypeptide, protein, or enzyme means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see also, Hancock et al., *EMBO J.*, 10:4033-4039 (1991); Buss et al., *Mol. Cell. Biol.*, 8:3960-3963 (1988); U.S. Pat. No. 5,776,689, each of which is incorporated herein by reference).

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, -carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following six groups each contain amino acids that are conservative substitutions for one another: 1) Alanine (Ala, A), Serine (Ser, S), Threonine (Thr, T); 2) Aspartic acid (Asp, D), Glutamic acid (Glu, E); 3) Asparagine (Asn, N), Glutamine (Gln, Q); 4) Arginine (Arg, R), Lysine (Lys, K); 5) Isoleucine (Ile, I), Leucine (Leu, L), Methionine (Met, M), Valine (Val, V); and 6) Phenylalanine (Phe, F), Tyrosine (Tyr, Y), Tryptophan (Trp, V).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/, or the like). Such sequences are then said to be "substantially identical" or "substantially similar." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is about 50, 100, 200, 300, 400, 500, or more amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. In certain embodiments, a comparison window may be at least about 25, 50, 75, 100, 150, 200, 250, 300, 400, 500, 600, or more positions. Methods of alignment of sequences for comparison are well-known in the art. Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J Mol. Biol.*, 48:443 (1970), by the search for similarity method of Pearson & Lipman, *Proc. Nat'l. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds., Wiley Interscience (1987-2005)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA*, 89:10915 (1989)) alignments (B) of 50, expectation (E) of 10, M=5, N=−4, and a comparison of both strands.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The Tm is the temperature, under defined ionic strength and pH, at which 50% of the target sequence hybridizes to a perfectly matched probe.

The term "isolated" or "purified" refers to a strain, such as a yeast strain, or material, such as a protein or nucleic acid, that is substantially or essentially free from components that normally accompany the material in its native state in nature. Purity or homogeneity generally are determined using analytical chemistry techniques such as polyacrylamide gel electrophoresis, high performance liquid chromatography, rRNA gene sequencing, and the like. A yeast strain, polynucleotide, or polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule. Generally, an isolated yeast strain represents greater than 50% of all microbiological species present in a sample, oftentimes an isolated yeast strain will represent greater than 75%, or greater than about 80%, 85%, 90%, 95%, of more of all microbiological species present in a sample.

EXAMPLES

Example 1

Isolation of Endophytic Yeast from Poplar Stems

One yeast strain isolated from stems of wild cottonwood (*Populus trichocarpa*) in Three Forks Park at the Snoqualmie River near the towns of North Bend and Snoqualmie, King County, Wash. was named wild poplar strain 1 (WP1). Two yeast strains isolated from stems of hybrid poplar (*Populus trichocarpa×P. deltoides*) in greenhouses at the University of Washington, Seattle, and Oregon State University, Corvallis were named as PTD2 and PTD3, respectively. The poplar stems were surface-sterilized with 10% bleach (1.2% active sodium hypochloride) for 10 minutes and 1% iodophor for 5 minutes, and then rinsed for 3-5 times with sterile water. The ends of the explants were removed, and stems were incubated in the light on Murashige and Skoog medium (MS; Caisson 61 laboratories Inc., Rexburg, Id.). Morphologically-distinct colonies were streak purified on YPD (Yeast extract, Peptone, and Dextrose) plates.

*Rhodotorula glutinis* strain ATCC 2527, obtained from American Type Culture Collection (ATCC), and a Baker's yeast *Saccharomyces cerevisiae* Meyen ex E.C. Hansen strain (Lesaffre yeast corporation, Milwaukee, Wis.) were used for comparison. The phylogenetic relatedness in the three rRNA genes: 18S, 26S (D1/D2 domains), and ITS, as well as their phenotypic characteristics was examined. The capacity to produce IAA by the three yeast strains was also examined.

FIG. 1 shows photomicrographs of the three yeast strains and *R. glutinis* ATCC in YPD broth. WP1 cells (1A) were ovoid to subspherical, subhyaline, vacuolate, budding on one end, and 6.5-9×5-8 μm. PTD2 cells (1B) were broadly ovoid, subhyaline, vacuolate, budding on one end, and 5-7×3-4 μm. Strain PTD3 cells (1C) were ovoid to subspherical, subhyaline, vacuolate, exhibited budding on one end, and 4-5.5×3-4 μm. *R. glutinis* (ATCC strain) cells (1D) were ellipsoid to ovoid, sub-olivaceous to sub-hyaline, budding at one or both ends, forming pseudohyphae, and 4.5-7.5×3-5 μm. All strains formed colonies of varying shades of pink on YPD agar plates at 30° C. Sexual reproduction was not observed in any of the three *Populus* isolates during culturing for one-week period at 30° C.

Example 2

Extraction of Yeast Genomic DNA

Genomic DNA of yeast was prepared according to the rapid isolation of yeast chromosomal DNA protocol (Ausubel et al., 1995) with modifications. Yeast cultures grown overnight in 10 mL YPD broth at 30° C. were collected by centrifuging at 3000×g for 5 min under room temperature and washed with 1 mL sterile DI H$_2$O. Cells were lysed by vortexing with 0.5 g glass beads in 1 mL breaking buffer and 1 mL phenol/chloroform/isoamyl alcohol at high speed for 3 min. The water layer was separated by centrifugation, transferred, and washed through multiple phenol/chloroform extraction steps. Extracted DNA was then precipitated using an equal amount of isopropanol at room temperature. Resuspended DNA in TE buffer was stored at −20° C.

Example 3

PCR Amplification of 18S, ITS, and D1/D2 Region

The present example focuses on the phylogenetic relatedness of three rRNA genes: 18S, 26S (D1/D2 domains), and ITS, from the novel isolated yeast strains Yeast DNA was purified and amplified with PCR using three sets of primers for 18S, ITS, and D1/D2 region of rRNA genes, respectively. The primers used in this study are listed in Table 1. A 1.8-kb fragment of 18S rRNA gene was amplified with primers NS8 and NS1. A 600-650 bp fragment of D1/D2 region at the 5' end of the large-subunit rRNA 84 gene was amplified with primers F63 and LR3. A 600-620 bp fragment of ITS1-5.8S-ITS2 region on the rRNA gene was amplified with primers ITS1 and ITS4. PCR was performed on DNA extracts in 25 μl with final concentrations of 1×PCR Pre-Mix buffer E (Epicentre, Madison, Wis.), 100 nM of forward and reverse primers, 5 U of Taq DNA polymerase (Fermentas), and 1 μL of template DNA. The reaction mixture was held at 95° C. for 5 minutes followed by 34 cycles of amplification at 95° C. for 30 s, annealing temperature as shown in Table 1 for 30 s and 72° C. for 60 s, with a final step of 72° C. for 5 minutes in a Mastercycler thermalcycler (Eppendorf, Westbury, N.Y.).

TABLE 1

Primers used for the PCR amplification of 18S, ITS, and D1/D2 genomic rRNA regions.

| Primer | Sequence (5'-3') | SEQ ID NO: | Annealing temperature, ° C. | Reference |
| --- | --- | --- | --- | --- |
| NS8 FP | TCC GCA GGT TCA CCT ACG GA | 1 | 44 | White et al., 1990 |

TABLE 1-continued

Primers used for the PCR amplification of 18S, ITS, and D1/D2 genomic rRNA regions.

| Primer | Sequence (5'-3') | SEQ ID NO: | Annealing temperature, °C. | Reference |
|---|---|---|---|---|
| NS1 RP | GTA GTC ATA TGC TTG TCT C | 2 | 44 | White et al., 1990 |
| F63 FP | GCA TAT CAA TAA GCG GAG GAA AAG | 3 | 45 | Fell et al., 2000 |
| LR3 RP | GGT CCG TGT TTC AAG ACG G | 4 | 45 | Fell et al., 2000 |
| ITS1 FP | TCC GTA GGT GAA CCT GCG G | 5 | 44 | White et al., 1990 |
| ITS4 RP | TCC TCC GCT TAT TGA TATG C | 6 | 44 | White et al., 1990 |

Example 4

Molecular Cloning and Sequencing

PCR products were subjected to electrophoresis in 0.8% agarose gel. Target bands were collected from the agarose gel and DNA extracted from it using the QIAEXII gel extraction kit (Qiagen, Madison, Wis.). DNA fragments were cloned using the pGEM T Easy kit (Promega, Madison, Wis.) following the manufacturer's instructions. Sequencing was conducted using the BigDye Terminator v3.1 Cycle Sequencing kit (Applied Biosystems) and an ABI 3730XL sequencer (Applied 100 Biosystems) at the Department of Biochemistry sequencing facility of the University of Washington. Sequence data have been submitted to Genbank under the accession numbers EU563924-EU563932.

TABLE 2

Genomic rRNA sequences.

| Strain | Gene | Accession number | SEQ ID NO: |
|---|---|---|---|
| WP1 | 18S ribosomal RNA | EU563924 | 7 |
| PTD2 | 18S ribosomal RNA | EU563925 | 8 |
| PTD3 | 18S ribosomal RNA | EU563926 | 9 |
| WP1 | ITS ribosomal RNA | EU563927 | 10 |
| PTD2 | ITS ribosomal RNA | EU563928 | 11 |
| PTD3 | ITS ribosomal RNA | EU563929 | 12 |
| WP1 | 26S D1/D2 ribosomal RNA | EU563930 | 13 |
| PTD2 | 26S D1/D2 ribosomal RNA | EU563931 | 14 |
| PTD3 | 26S D1/D2 ribosomal RNA | EU563932 | 15 |

Example 5

Analysis of DNA Sequences

DNA sequences were aligned with the program ClusterW (Thompson et al., 1994) using default gap penalties. The selection of sequences for construction of phylogenetic trees was done by comparing the target sequences to all sequences in the GenBank by the online BLAST program. Phylogenetic trees were constructed using the neighbor joining distance method (Saitou and Nei, 1987) and distances computed using the Jukes-Cantor methods (Jukes and Cantor, 1969) and using the Maximum Parsimony method (Eck and Dayhoff, 1966). All analyses were conducted with the program MEGA 4 (Tamura et al., 2007).

Analysis of the 18S, ITS1-5.8S-ITS2, and D1/D2 regions suggested that isolates PTD2 and PTD3 were most closely related to *Rhodotorula mucilaginosa* (FIGS. 2-7). PTD2 was identical to *R. mucilaginosa* in both the 18S and D1/D2 region sequences, but differed from *R. mucilaginosa* in 5 of 183 base positions when the ITS1-5.8S-ITS2 sequences were compared. PTD3 was identical to *R. mucilaginosa* in the D1/D2 region, and differed from *R. mucilaginosa* in 1 of 586 bases in the 18S sequence and 7 of 583 bases in the ITS1-5.8S-ITS2 sequence.

Sequences from WP1 appeared to support relationships with several different species. *Rhodosporidium babjevae* and WP1 shared the most similar 18S rRNA gene sequences (FIG. 2), while the ITS1-5.8S-ITS2 and D1/D2 sequences of WP1 were most similar to those of *Rhodotorula graminis* and *Rhodotorula glutinis* (FIGS. 3 and 4), respectively. The ITS1-5.8S-ITS2 sequence of WP1 differed from *R. glutinis* at 4 of 583 base positions (all in the ITS1 region), from *R. graminis* in 1 of 583 base positions (in the ITS1 region), and from that of *R. babjevae* in 6 of 583 positions (4 in ITS1, 1 in 5.8S, and 1 in ITS2). In the D1/D2 region, WP1 was identical to *R. glutinis* based on 586 positions, and differed from *R. graminis* in 1 and from *R. babjevae* in 2 base positions. In the 18S, WP1 was identical to *R. babjevae* based on 952 positions, and differed from *R. glutinis* by 1/952. It should be noted that the WP1 18S sequence was identical to the sequence of a *R. graminis* strain in GenBank (Accession number X83827) but the *R. graminis* sequence contained missing data for 7 positions. The strain was not included in the phylogenetic tree shown in FIGS. 2 and 5.

Example 6

IAA Production Test

To quantify the production of IAA, isolates were grown in YPD/YMA medium with or without 0.1% (w/v) L-tryptophan for 1, 2, 5, and 7 days and 1.5 mL of the cells were pelleted by centrifugation at 10,000×g for 5 min. One mL of supernatant was mixed with 2 mL of Salkowski reagent (2 mL of 0.5 M $FeCl_3$+98 mL 35% $HClO_4$) (Gordon and Weber, 1951), and the intensity of pink color developing in the mixture after 30 min was quantified by a Hach DR/4000 spectrophotometer (Hach, Loveland, Colo.) at wavelength 530 nm. Cell pellets were dried at 100° C. overnight and weighed for normalizing IAA production. Similarly, pink color was also developed for a series of IAA standard solutions to establish a stand curve.

Figure 9:
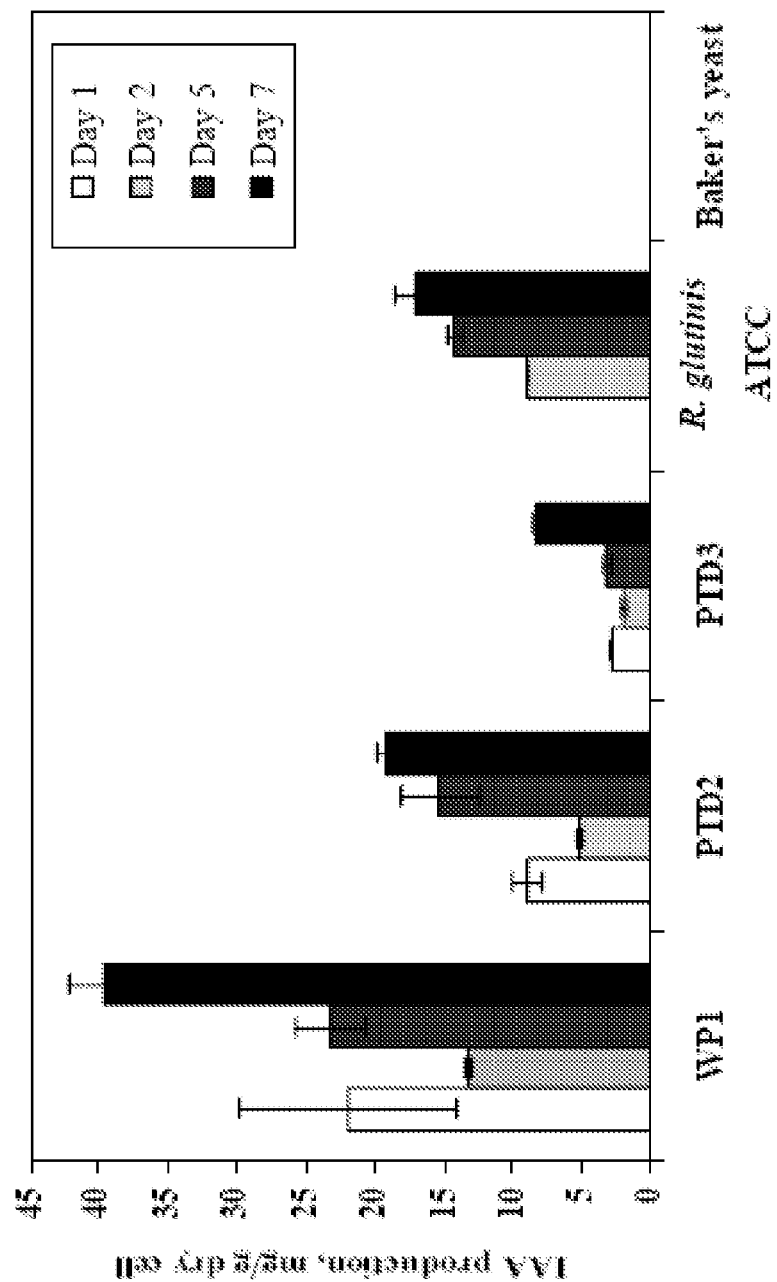
FIG. 9. IAA production by yeast strains incubated with 0.1% L-tryptophan.
Figure 10:
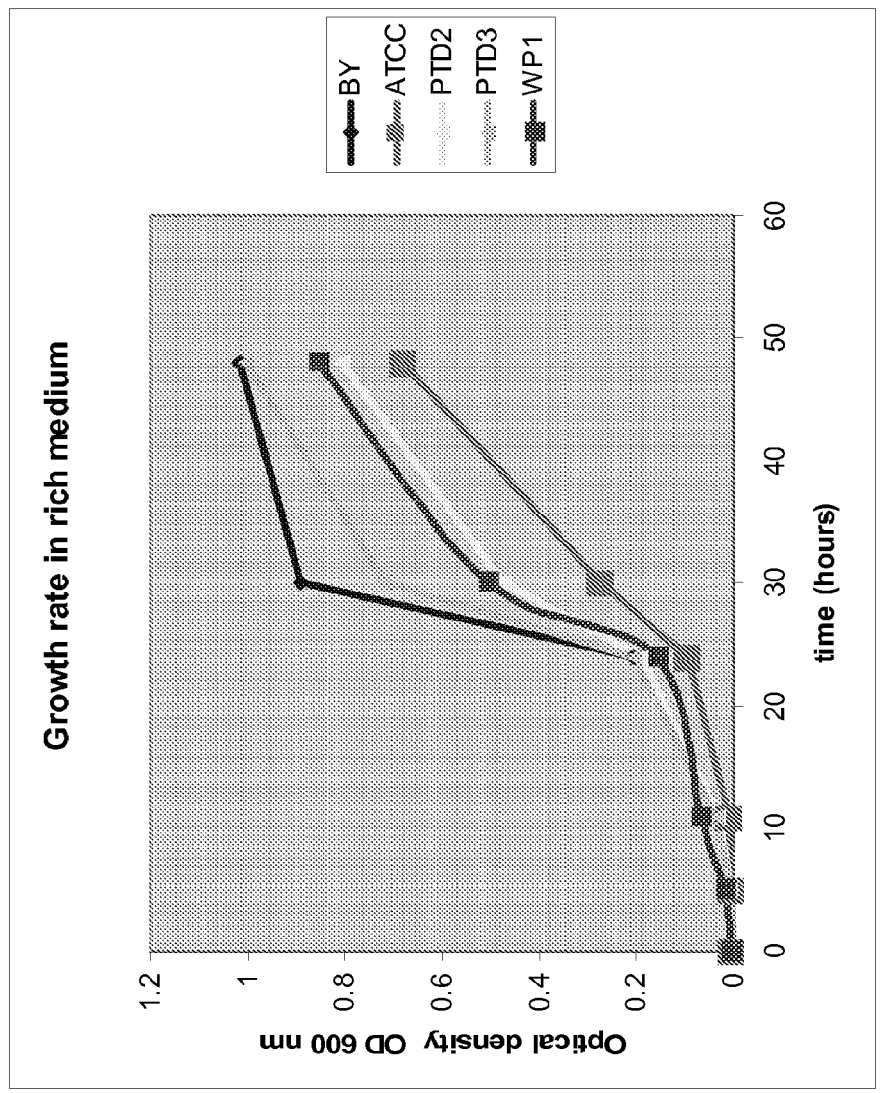
FIG. 10. Growth rates of the yeast strains WP1, PTD2, PTD3, ATCC, and Baker's yeast in rich medium.
Figure 11:
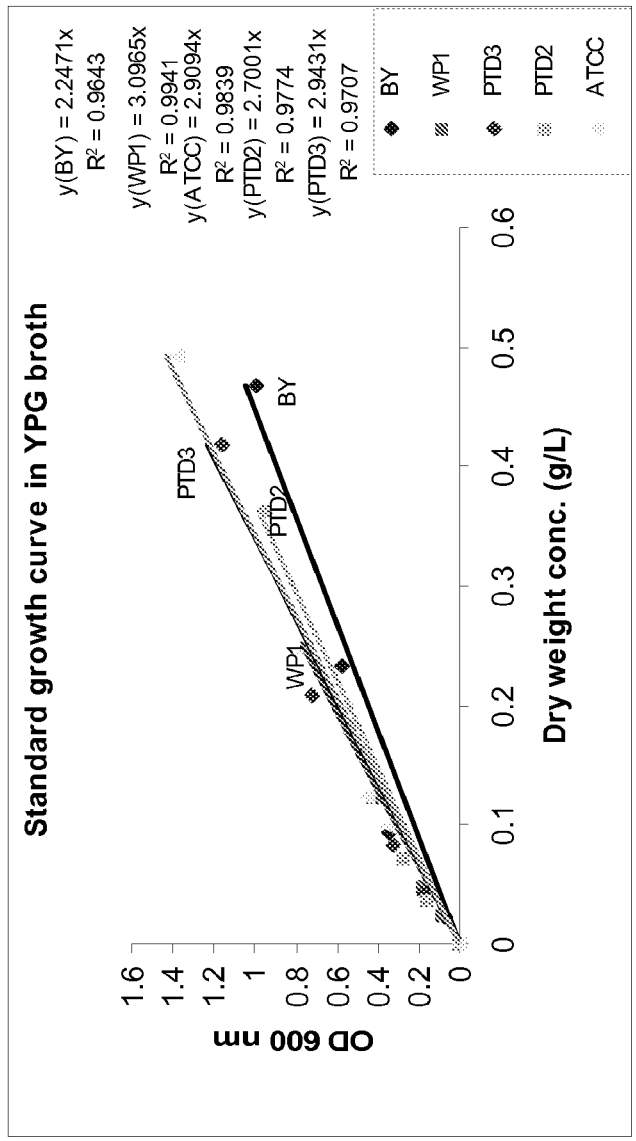
FIG. 11. Experimental growth curves for the yeast strains WP1, PTD2, PTD3, ATCC, and Baker's yeast in YPG medium.
Figure 12:
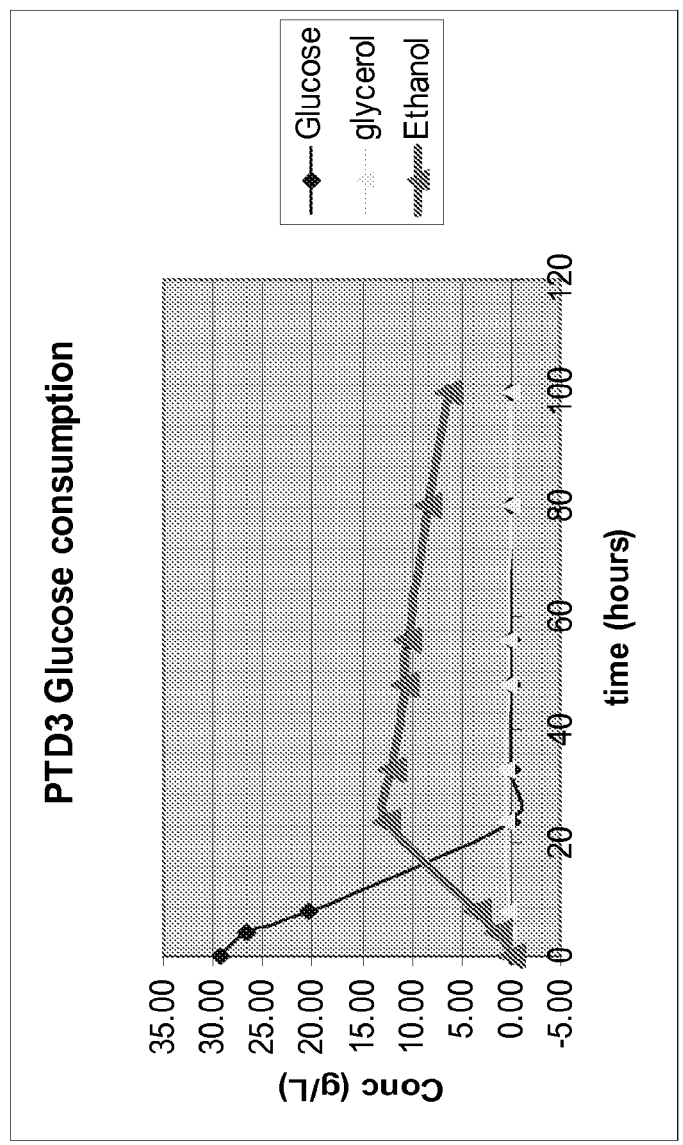
FIG. 12. Glucose consumption, glycerol production, and ethanol production in a culture PTD3 grown in glucose.
Figure 13:
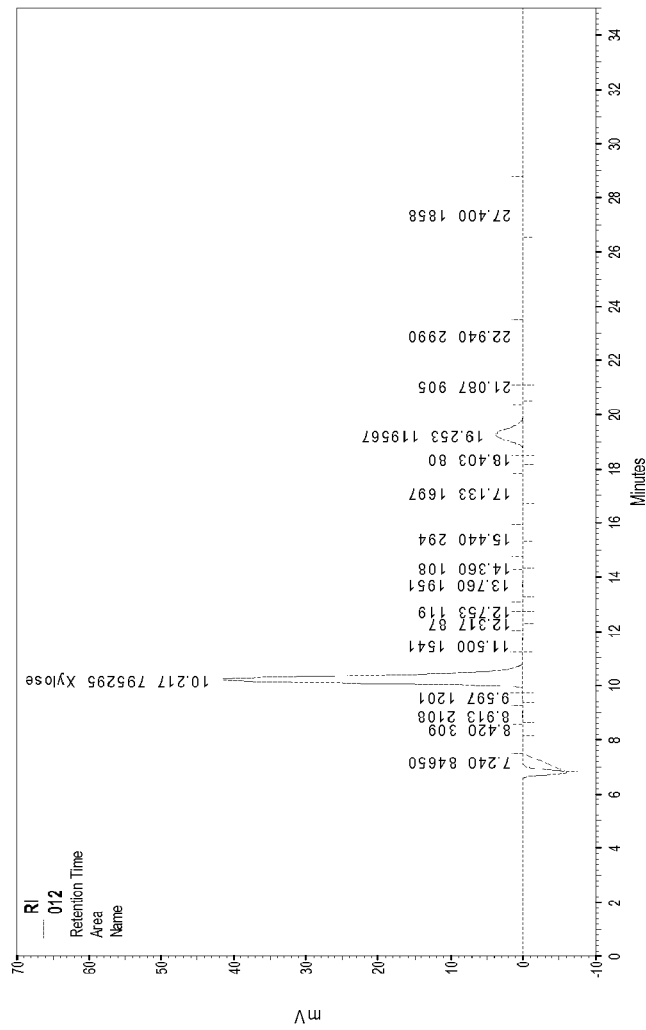
FIG. 13. HPLC chromatograms for the data provided in FIG. 15, showing the amount of the xylose peak at the beginning of the experiment.
Figure 14:
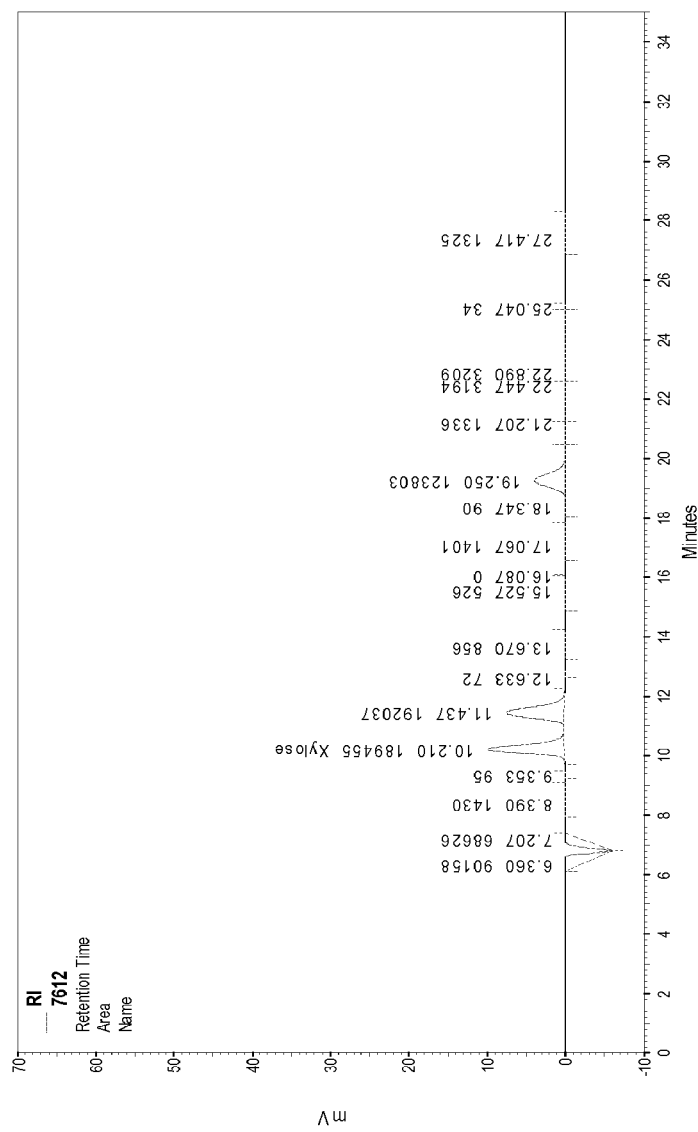
FIG. 14. HPLC chromatograms for the data provided in FIG. 15, showing the reduction of the xylose peak and formation of the xylitol peak at the end of the experiment.
Figure 15:
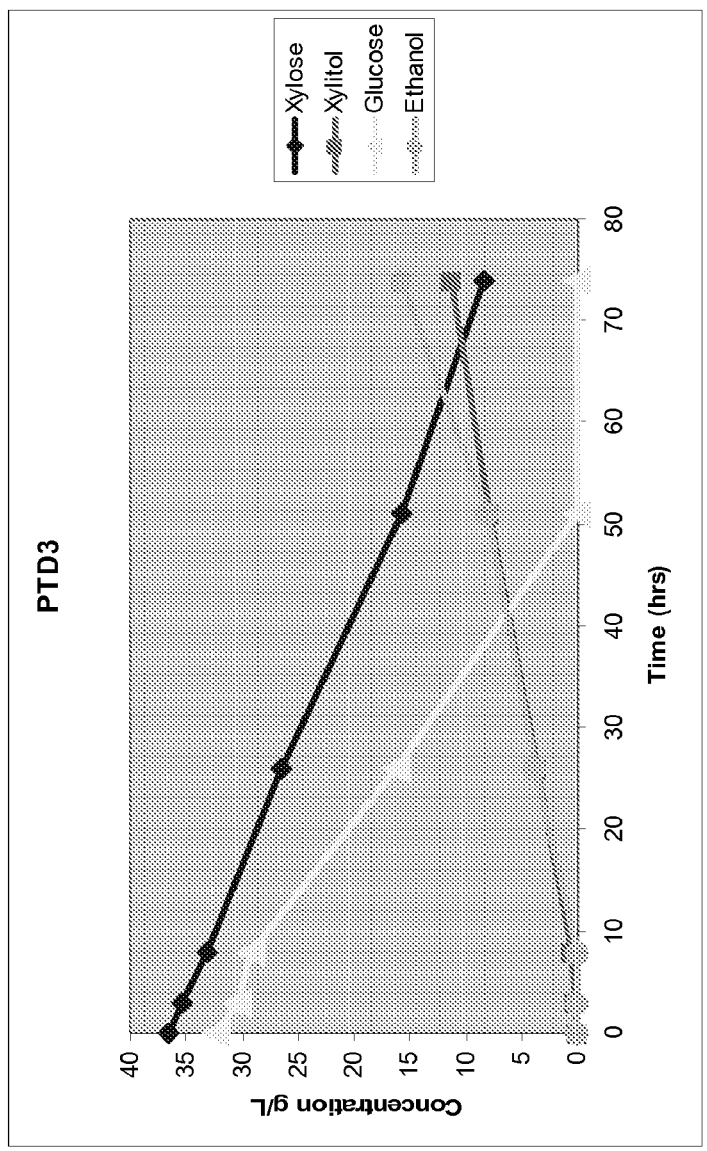
FIG. 15. Consumption of glucose and xylose and production of xylitol and ethanol in a culture of PTD3 yeast grown in glucose and xylose separately.
Figure 16:
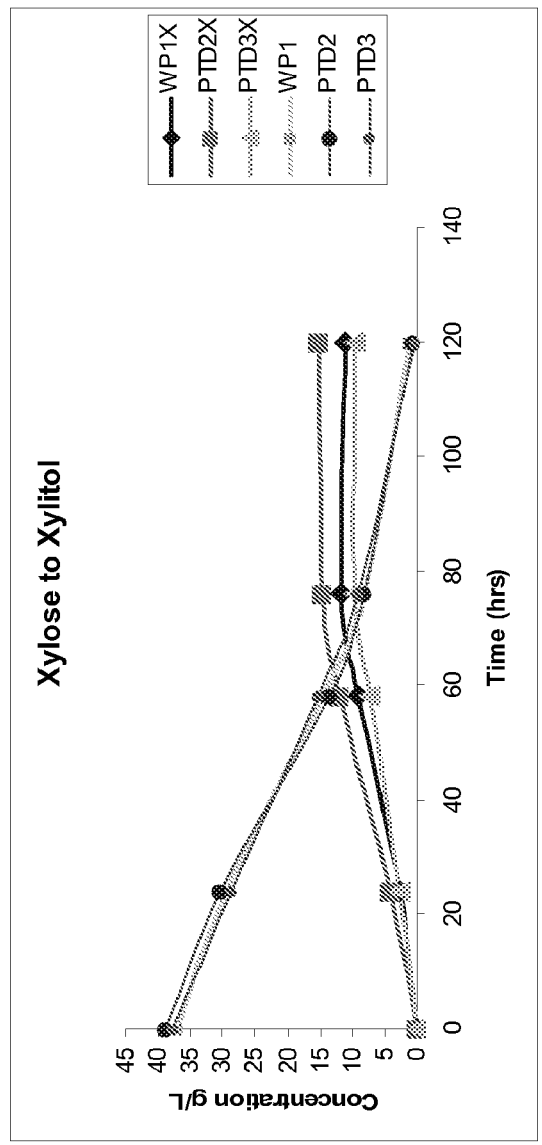
FIG. 16. Conversion of xylose to xylitol by the yeast strains WP1, PTD2, and PTD3 cultured in xylose.
Figure 17:
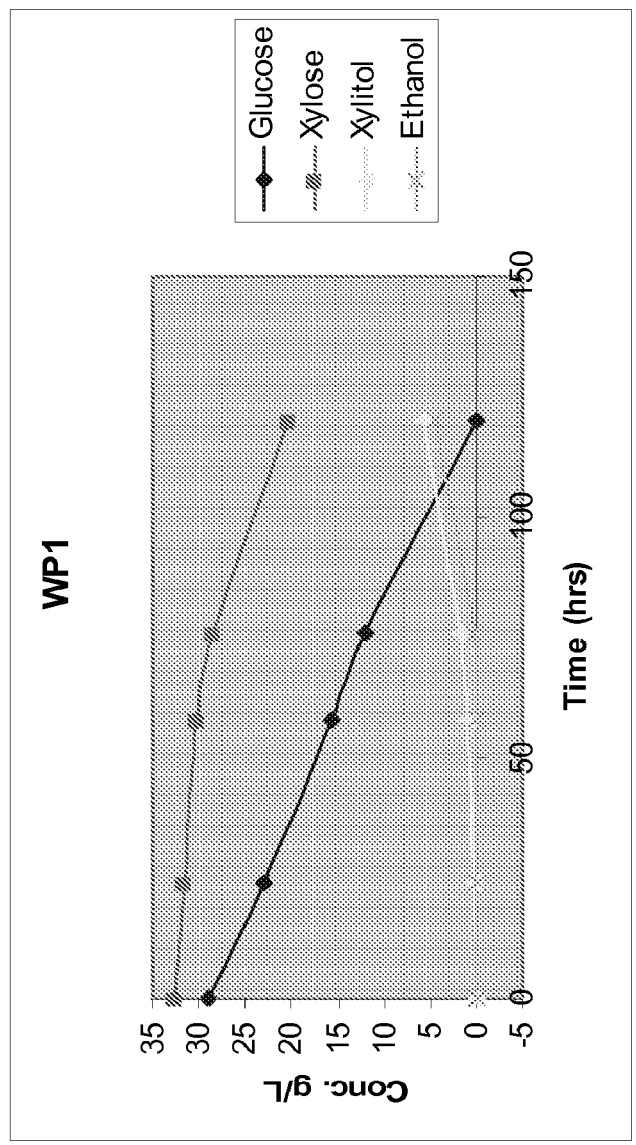
FIG. 17. Consumption of glucose and xylose and production of xylitol and ethanol in a culture of WP1 yeast grown in glucose and xylose separately.
Figure 18:
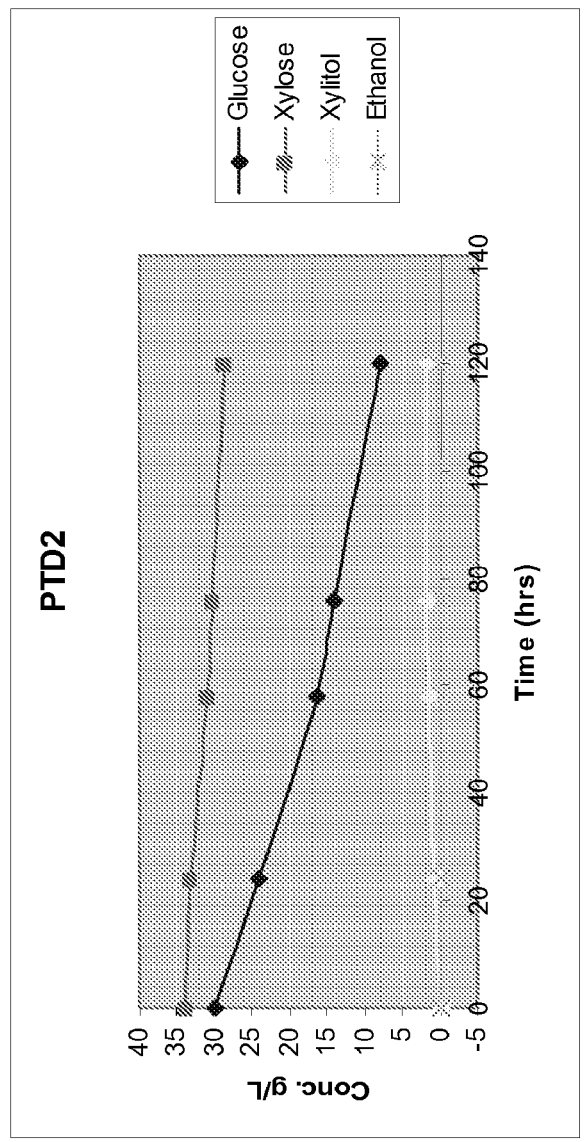
FIG. 18. Consumption of glucose and xylose and production of xylitol and ethanol in a culture of PTD2 yeast grown in glucose and xylose separately.
Figure 19:
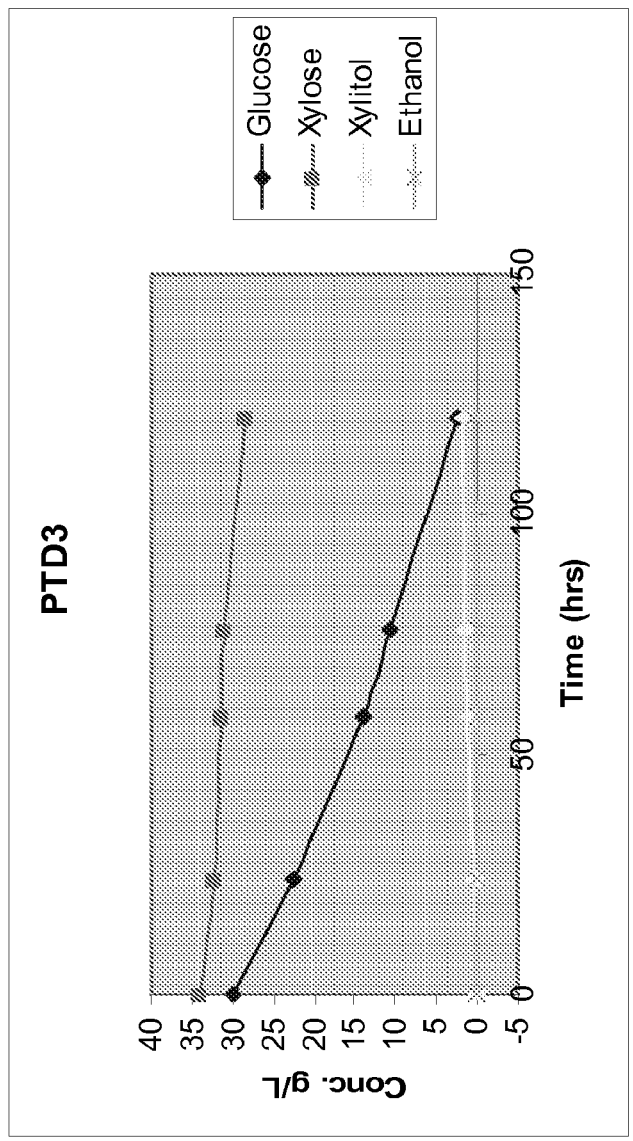
FIG. 19. Consumption of glucose and xylose and production of xylitol and ethanol in a culture of PTD3 yeast grown in glucose and xylose separately.
Figure 24:
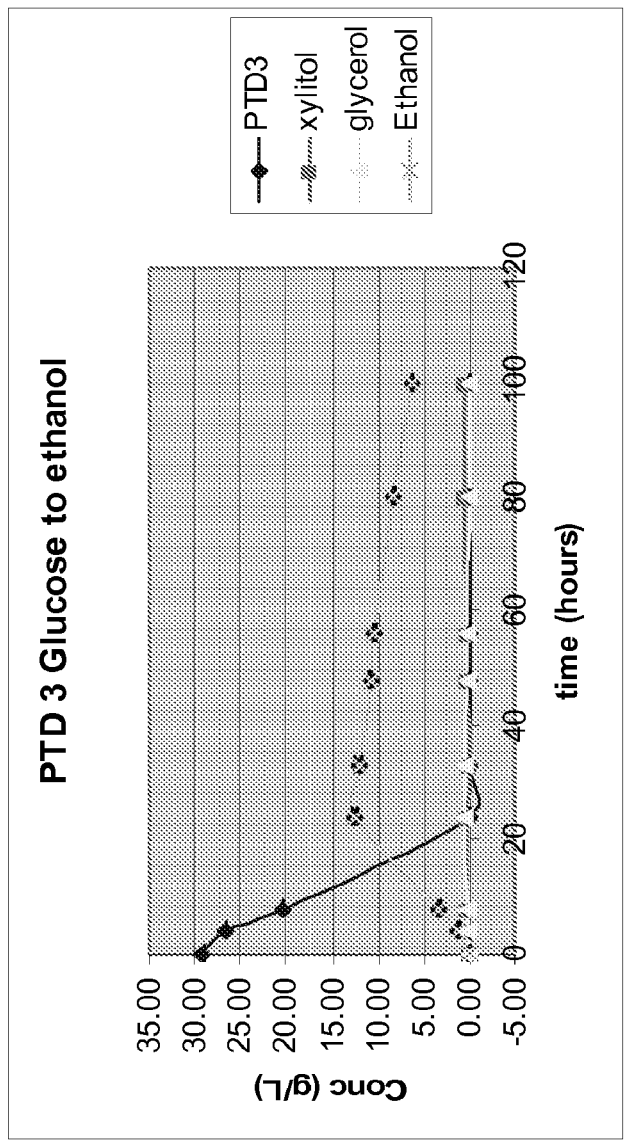
FIG. 24. Fermentation of glucose to ethanol by PTD3 yeast cultured in glucose with MS and yeast extract.
Figure 25:
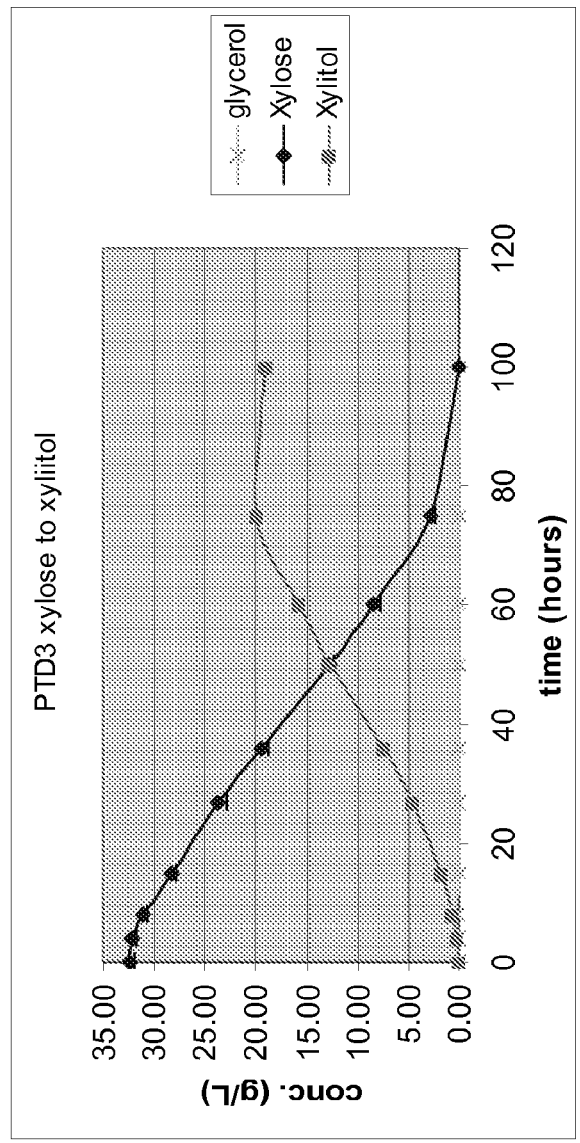
FIG. 25. Fermentation of xylose to xylitol by PTD3 yeast cultured in xylose with MS and yeast extract.
Figure 26:
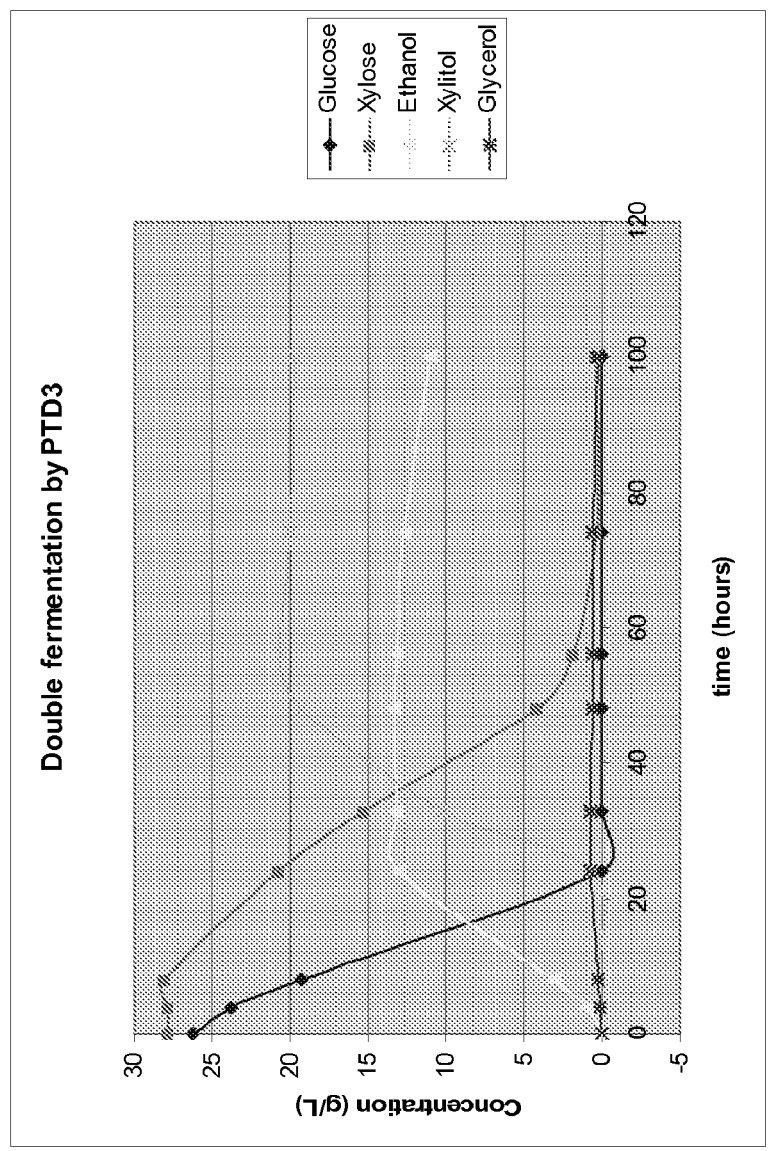
FIG. 26. Double fermentation of glucose and xylitol to ethanol and xylitol by PTD3 yeast cultured in glucose and xylose together and MS and yeast extract.
Figure 27:
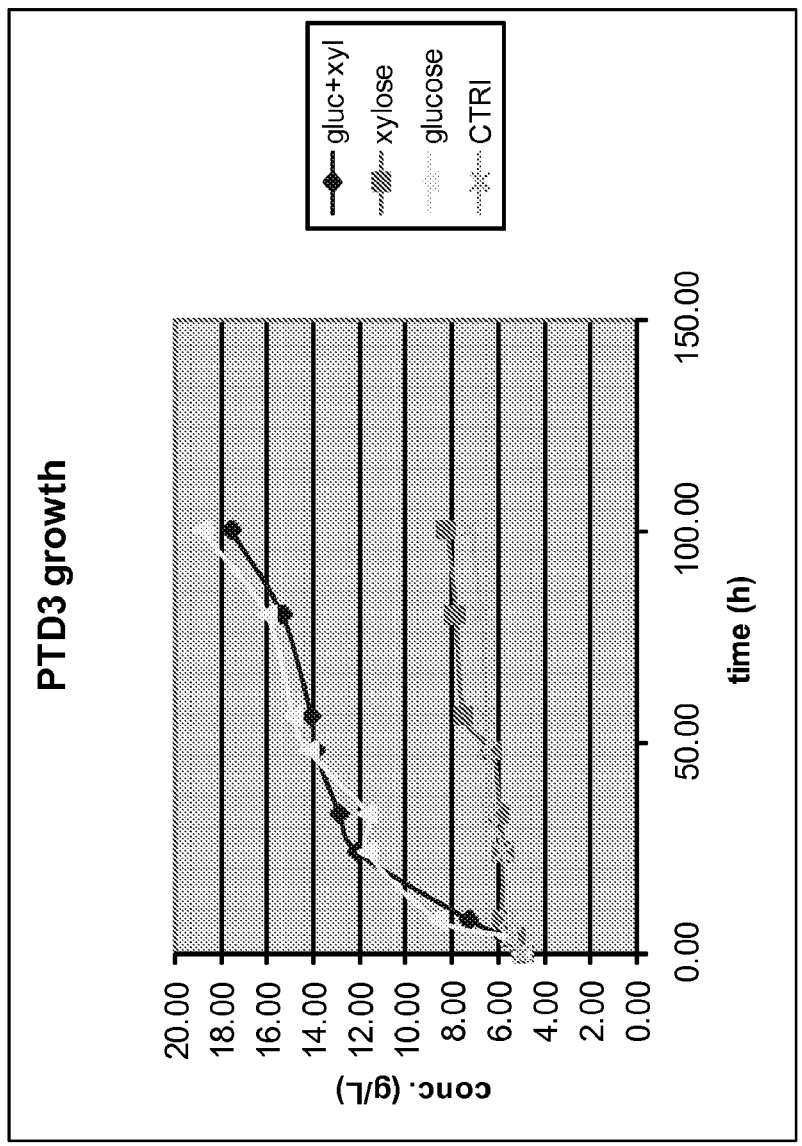
FIG. 27. Growth rate of PTD3 yeast in medium containing glucose and xylose.
Figure 28:
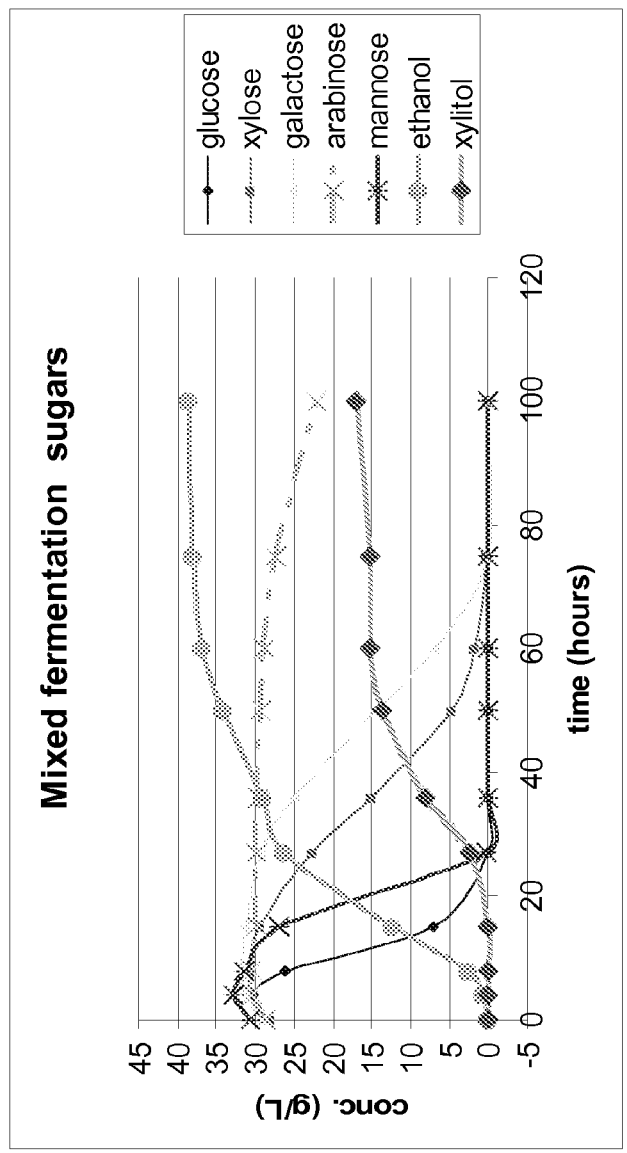
FIG. 28. Mixed fermentation of hexose (28A) and pentose (28B) sugars by PTD3 yeast cultured in MS and yeast extract with arabinose, galactose, glucose, xylose and mannose.
Figure 29:
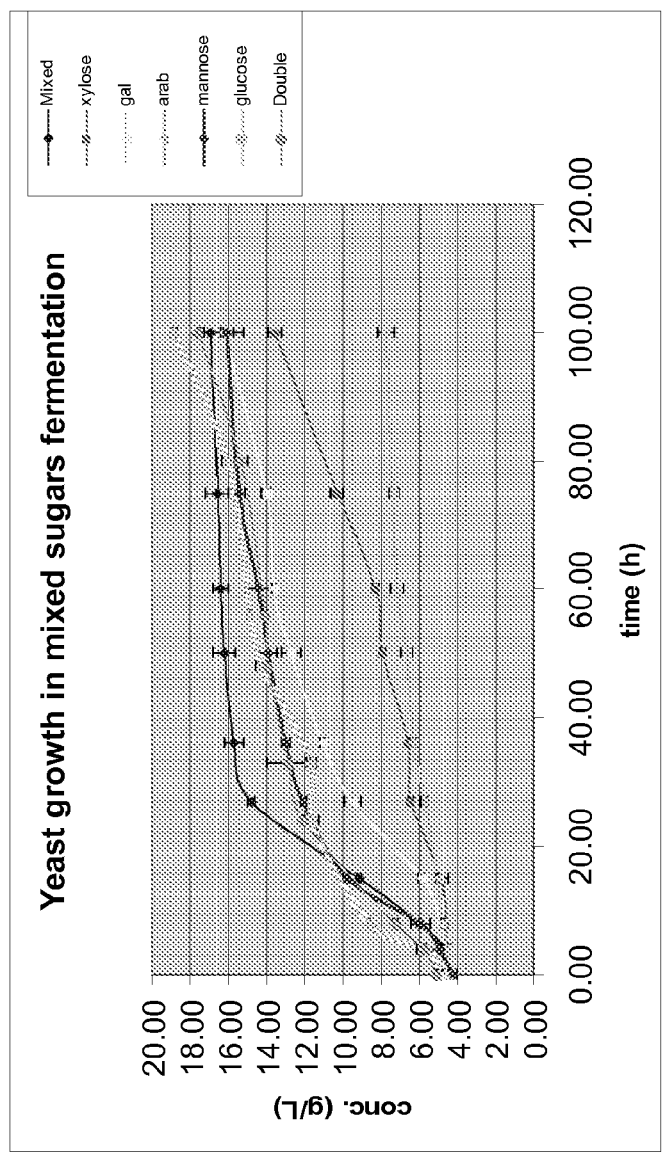
FIG. 29. Growth rate of PTD3 yeast grown in mediums containing mixed sugars, arabinose, xylose, glucose, galactose, and mannose with MS and yeast extract.
Figure 30:
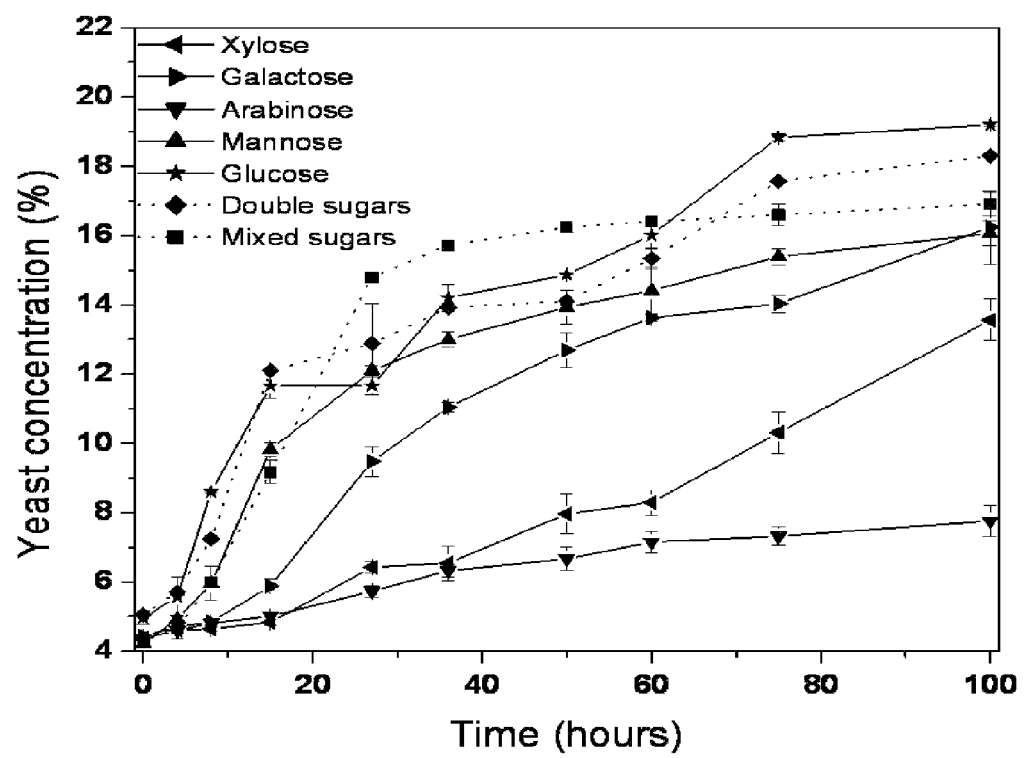
FIG. 30. Growth rate of PTD3 yeast grown in mediums containing mixed sugars, arabinose, xylose, glucose, galactose, and mannose with MS and yeast extract.
Figure 31:
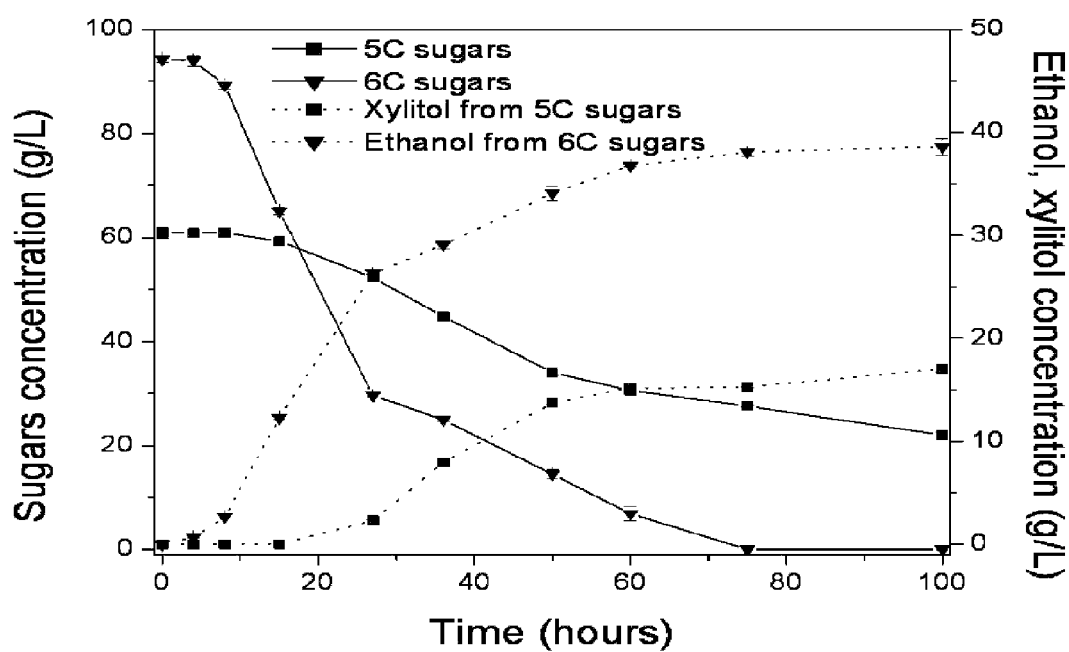
FIG. 31. Mixed fermentation of glucose and xylitol to ethanol and xylitol by PTD3 yeast cultured in arabinose, xylose, glucose, galactose, and mannose with MS and yeast extract.

No detectable IAA was produced for all tested yeast strains after 7-day incubation without L-tryptophan. When incubated with 0.1% L-tryptophan, strains of WP1, PTD2, PTD3, and *R. glutinis* ATCC showed significant production of IAA (FIG. 9). No detectable IAA was produced by Baker's yeast. The overall production of IAA increased with time for the four yeast strains. Among them, WP1 had the highest IAA production and PTD3 had the least Example 7

Phenotypic Characterization of Yeast Strains

The morphology of yeast strains was determined and photographs made using a Leica DMR compound microscope equipped with brightfield and differential interference contrast optics and a Leica DC300 digital camera (Leica Microsystems GmbH, Wetzlar). Utilization of kinds of carbon sources was examined using a commercial API 20C AUX yeast identification kit (bioMerieux, Durham, N.C.) according to the manufacture's instructions. Yeast cultures in YPD broth diluted to an optical density ($OD_{600}$) of 0.451, which is equivalent to McFarland standard No. 2, in 0.85% NaCl solution were applied to the API 20C AUX strips. The strips then were incubated at 30° C. Pink color developed on the incubation strips at 48 and 72 hours to indicate utilization of individual carbon sources by tested yeast strains.

A commonly used method to distinguish many yeast species is comparison of their abilities to utilize certain organic compounds as the sole major source of carbon (Barnett et al., 2000). A commercial yeast identification kit, API 20C AUX, can identify rapidly common and rare clinical yeast isolates with high efficacy (Ramani et al., 1998; Verweij et al., 1999). Table 3 summarizes utilization of 19 different organic compounds by the three *Populus* isolates and two controls (*R. glutinis* ATCC and Baker's yeast), with the API 20C AUX system. Characteristics of *R. graminis* were compiled from the literature (Barnett et al. 2000).

TABLE 3

Summary of utilization of 19 carbon sources by strains WP1, PTD2, PTD3, ATCC, and Baker's yeast assessed using the API 20C AUX system. The profile for *R. graminis* was compiled from Barnett et al. (2000).

| Carbon Source | WP1 | PTD2 | PTD3 | *R. glutinis* ATCC | Baker's yeast | *R. graminis* |
|---|---|---|---|---|---|---|
| D-glucose | + | + | + | + | + | + |
| Glycerol | + | + | − | − | − | + |
| Calcium 2-keto-gluconate | + | − | − | + | − | V |
| L-arabinose | − | + | + | − | − | +, D |
| D-xylose | + | + | + | − | − | + |
| Adonitol | + | + | + | − | − | NA |
| Xylitol | − | + | + | − | − | +, D |
| D-galactose | + | − | − | + | + | + |
| Inositol | − | − | − | − | − | − |
| D-sorbitol | + | + | + | + | − | NA |
| Methyl-αD-glucopyranoside | − | − | − | − | + | NA |
| N-acetyl-glucosamine | − | − | − | − | − | − |
| D-cellobiose | − | − | − | − | + | − |
| D-lactose | − | − | − | − | − | − |
| D-maltose | − | + | + | + | + | V |
| Sucrose | + | + | + | + | + | + |
| D-trehalose | − | + | + | − | + | +, D |
| D-melezitose | − | V | − | + | + | − |
| D-raffinose | + | + | + | + | − | + |

Figure 8:
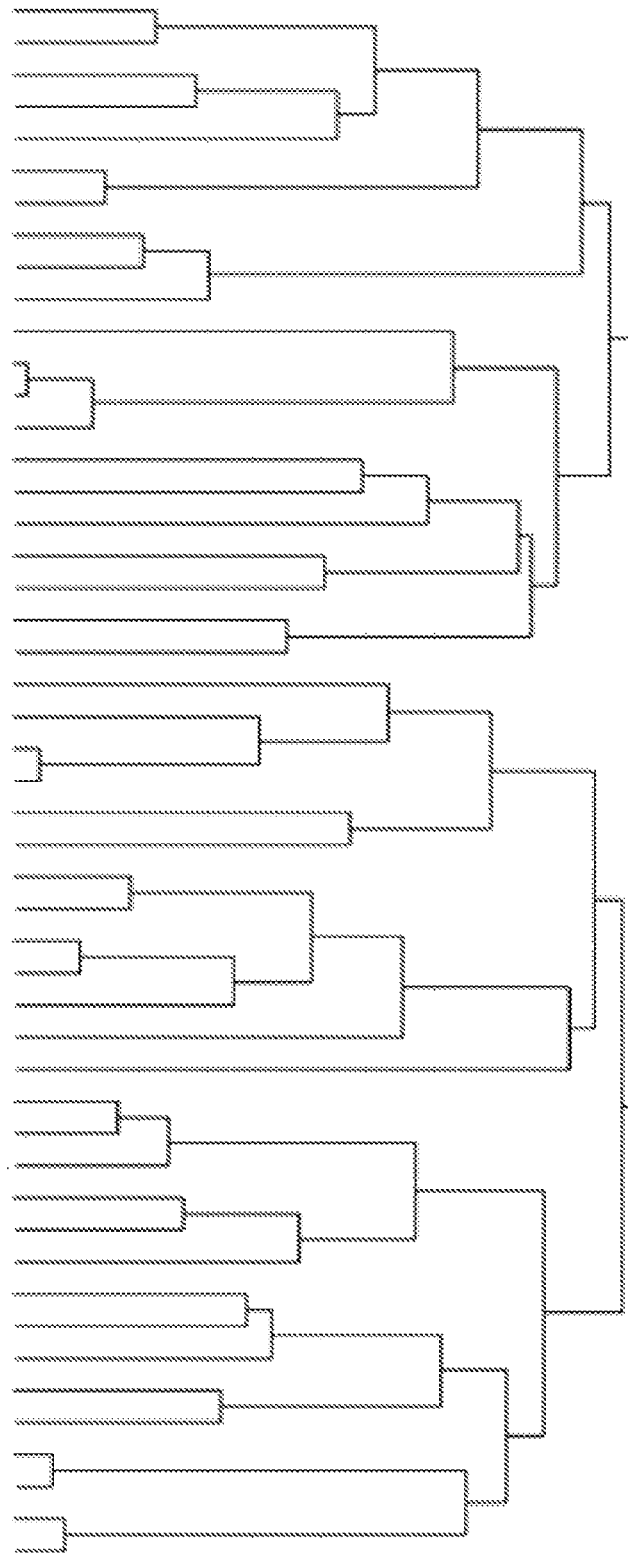
FIG. 8. Clustering of phenotypic characteristics profiles of the studied yeast strains (WP1, PTD2, PTD3, ATCC, and Baker's yeast) and the reference species of the API 20C AUX system (bioMerieux, 2007) based on the overall similarity. The distance between any two clusters was determined by the Ward's minimum variance method (Milligan, 1980).

"+"—positive,
"−"—negative,
"V"—variable,
"NA"—not available,
"D"—delayed longer than 7 days The clusterings between Baker's yeast and *S. cerevisiae* and between *R. glutinis* ATCC and *R. glutinis* in FIG. 8 demonstrated that the identification system was effective. Similarity of PTD2, PTD3, and *R. mucilaginosa* (FIG. 8) carbon utilization profiles confirmed the groupings based on rRNA gene sequences. However, WP1 did not cluster with any *Rhodotorula* species in the reference list of the API 20C AUX system (FIG. 8) and diverged in utilization of 5 compounds (glycerol, D-xylose, adonitol, D-maltose, and D-melezitose) when compared with *R. glutinis* ATCC. Compared to the reported carbon-utilization profile from the literature, WP1 diverged from *R. graminis* only in utilizing D-cellobiose out of 13 organic compounds. Regarding another 3 compounds (L-arabinose, xylitol, and D-trehalose) labeled positive for *R. graminis* in Table 2 with over 7-day delayed observation, direct comparison to the WP1 profile obtained after 3-day incubation with API 20C AUX system is not proper.

Example 8

Clustering Analysis of Phenotypic Characteristics of Yeast Strains

A clustering map was drawn by JMP statistics software version 6 (SAS, Cary, N.C.) according to the Ward's minimum variance method (Milligan, 1980). Distance for Ward's method is determined according to the formula:

$$D_{KL} = \frac{\|\bar{x}_K - \bar{x}_L\|^2}{\frac{1}{N_K} + \frac{1}{N_L}}$$

wherein $X_K$ and $X_L$ are the mean vectors for cluster $C_K$ and $C_L$, respectively, $C_K$ is the $K^{th}$ cluster and $C_L$ is the $L^{th}$ cluster; $N_K$ and $N_L$ are the numbers of observations in $C_K$ and $C_L$.

Three pink-pigmented yeast strains isolated from stems of *Populus* grew well on YPD medium under aerobic conditions. Phylogenetic analysis of rRNA gene sequences supported determination of the yeast strains, PTD2 and PTD3 as *Rhodotorula mucilaginosa*. Determination of WP1 was not as simple as that of PTD2 and PTD3 since analyzing different sequence data provided differing results. *Rhodotorula* and *Rhodosporidium* are members of the class Urediniomycetes of phylum Basidiomycota. *Rhodotorula glutinis, R. graminis, R. babjevae,* and *R. mucilaginosa* grouped together in the *Sporidiobolus* clade, based on phylogenetic analysis of ITS and D1/D1 regions (Fell et al., 2000; Scorzetti et al., 2002). *Rhodotorula glutinis, R. graminis*, and *R. babjevae* occurred on the same branch of the *Sporidiobolus* clade, suggesting a close phylogenetic relationship among them. As the ITS region is generally considered to be less conserved than either small or large subunits of rRNA genes (Scorzetti et al., 2002), the ITS analysis could be more informative in distinguishing close related species. A single substitution out of 583 positions in the ITS1-5.8S-ITS2 between WP1 and *R. graminis* compared to 4 substitutions for WP1 and *R. glutinis* and to 6 substitutions for WP1 and *R. babjevae* suggests that WP1 is more closely related to *R. graminis*. In addition, WP1 shared higher similarity on carbon-utilization profiles with *R. graminis* than *R. glutinis*. Based on the phylogenetic and phenotypic characteristics of WP1, we regard the WP1 isolate as most closely fitting the current concept of *R. graminis*.

*Rhodotorula mucilaginosa* has been isolated from a wide variety of sources, including the bark of *Quercus suber* L. (cork oak) (Villa-Carvajal et al., 2004), soil and mosses from Antarctica (Pavlova et al., 2001), food stuffs (Haridy, 1993; Botes et al., 2007), and humans (Neofytos et al., 2007). The species has been reported frequently from wastewater treatment plants and exhibited tolerance to heavy metals such as copper, cadmium, and uranium (de Siloniz et al., 2002; Balsalobre et al., 2003; Villegas et al., 2005). Epoxide hydrolase of *R. mucilaginosa* can hydrolyze glycidyl ethers (Kotik et al., 240 2005), dibenzofuran (Romero et al., 2002), and other benzene compounds (Middelhoven 241 et al., 1992) in environmental bioremediation processes. *Rhodotorula graminis* was first isolated from the leaf surfaces of pasture grasses (di Menna, 1958) and later found widely in the environment, being isolated from soil (Vadkertiova and Slavikova, 1994; Hobbie et 244 al., 2003), *Ceratonia siliqua* L. (carob trees) (Spencer et al., 1995), and tropical fruits (Trindade et al., 2002). The species has shown an ability to cleave aromatic rings (Durham et al., 1984) and has been studied for the bioremediation of benzene compounds (Middelhoven, 1993).

Recently, the role of endophytes in phytoremediation of xenobiotics has been highlighted, including increasing plant tolerance to heavy metals (Lodewyckx et al., 2001), reducing phytotoxicity of herbicides (Germaine et al., 2006), and facilitating degradation of nitro-aromatic compounds (van Aken et al., 2004b). The tolerance to heavy metals and degradation of xenobiotics by *R. mucilaginosa* and *R. graminis* suggests the new *Populus* endophytic yeast strains may be suitable for phytoremediation applications. Furthermore, the production of IAA by the three yeast strains could potentially promote plant growth.

The three yeast strains produced IAA only with the addition of L-tryptophan. As one of the most expensive standard protein amino acids, in terms of energy, to produce (Hrazdina and Jensen, 1992), tryptophan is not biosynthesized by all bacteria and yeasts. Those microorganisms incapable of synthesizing tryptophan have to rely on their plant hosts or surrounding microbial sources (Radwanski and Last, 1995). With tryptophan available in the *Populus* tissue, the endophytic yeasts do not have to spend high energy on synthesis of the amino acid by themselves. At the same time, the ability to convert tryptophan to IAA by the endophytes would, in return, benefit the tryptophan provider, which may be seen as a mutually advantageous plant-microbe example.

To our knowledge, the yeast strains provided by the present invention are the first endophytic yeast strains isolated from species of *Populus*. The strain from wild *Populus*, WP1, has been chosen for whole genome sequencing by the Joint Genome Institute of the Department of Energy due to its potential applications for bioenergy production. The determination and characterization presented in the present invention should benefit future research on these strains.

Example 8

Growth Requirement Test

In order to study the sugar utilization of the endophytic yeast strains, WP1, PTD3 and the baker's yeast (BK), isolates were streaked from frozen glycerol stocks onto yeast extract, peptone, dextrose (YPD) agar to obtain isolated colonies. A single colony was transferred to 10 ml of YPD broth and incubated on a shaker at 30° C. overnight. The overnight culture was harvested and washed with MS medium (Caisson Labs MSP009) twice. For growth curve assays, cells were grown in 25 ml of MS medium containing either 3% glucose or 3% xylose at pH 5.8. Growth was monitored using a spectrophotometer measuring the optical density at 600 nm (OD600). Statistical analysis was done using split plot ANOVA (Intercooled Stata 10.0, StataCorp LP, College Station, Tex.) in order to account for the multiple measures taken over time on each flask, and the replicated flasks for each sample.

Figure 34A:
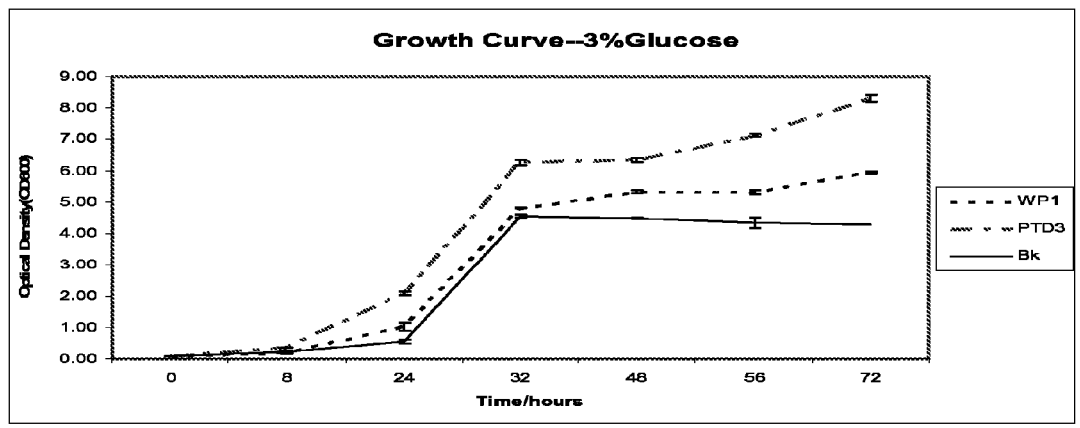
FIG. 34. (A) Growth of WP1 and PTD3 in MS medium with 3% glucose as the carbon source. Baker's yeast (BK; ATCC6037) was used as a positive control. The experiments were performed in triplicate and the error bars indicate the standard deviations. (B) Growth of WP1 and PTD3 in MS medium with 3% xylose as the carbon source. Baker's yeast (BK) was used as a control. The experiments were performed in triplicate and the error bars indicate the standard deviations.
Figure 34B:
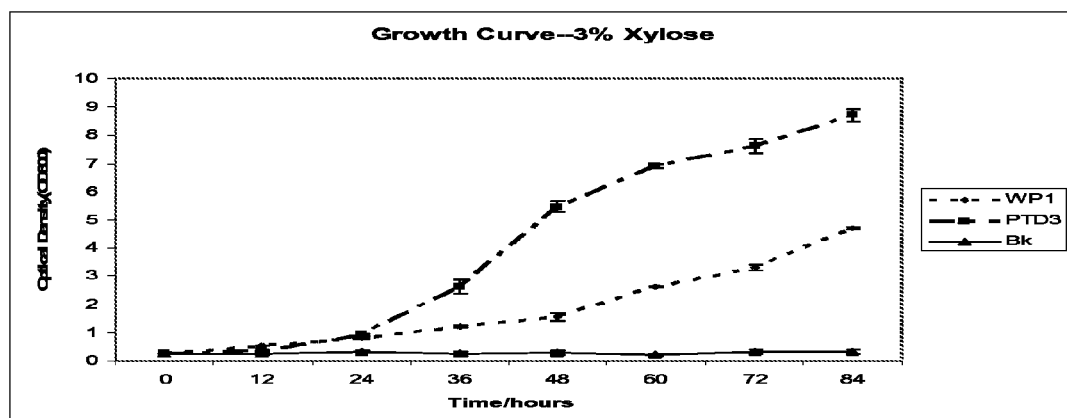

In order to study the sugar utilization of the two endophytic yeast strains, WP1 and PTD3, growth rate was monitored in media with different sugars. The growth curve experiments showed that both WP1 and PTD3 grew well in glucose (FIG. 34A) and xylose (FIG. 34B) sugars. As reported previously, Baker's yeast did not utilize xylose. It is also noteworthy that PTD3 grew better than WP1 under the two conditions and PTD3 was a better xylose utilizer (FIG. 34B). There was about a 24 hour-delay before WP1 and PTD3 started growing in glucose and xylose. The delay was most likely from the shift from rich medium (YPD) to minimal medium (plain MS).

Example 9

Cloning of the Xylose Reductase (XR) and Xylitol Dehydrogenase (XDH) Encoding Genes XYL1 and XYL2 from WP1

Yeast strain WP1 was isolated from stems of wild cottonwood (*Populus trichocarpa*) and was identified as *Rhodotorula graminis* (Xin et al. 2009). Another yeast strain, PTD3, was isolated from stems of hybrid poplar (*Populus trichocarpa×P. deltoides*) and was identified to be species *Rhodotorula mucilaginosa* (Xin et al. 2009). A baker's yeast ATCC6037 strain was used as the control yeast.

WP1 and PTD3 genomic DNA was prepared following a published protocol (Burke et al. 2000) with the following modifications: two extra phenol:chloroform/chloroform extractions and isopropanol precipitation were carried out. For mRNA preparation, cells were grown in YPD, which was prepared as described (Kaiser et al. 1994) except that sugars were autoclaved separately from the basal medium. YPX and YPGX were similar to YPD but replaced dextrose with xylose or xylose plus glucose. Isolation of mRNA was performed by the method described in (Laplaza et al. 2006).

Isolated RNA was quantified using a NanoDrop spectrophotometer (ND1000). Reverse transcription (RT) and subsequent PCR amplifications were performed sequentially using the OneStep RT-PCR Kit (QIAGEN). The whole WP1

XR and XDH-encoding genes were amplified by RT-PCR using two sets of primers (WP1-XR-F, WP1-XR-R and WP1-XDH-F, WP1-XDH-R), which were designed based on the sequences of XYL1 and XYL2 genes in *Pichia stipitis* (GenBank accession numbers: CAA42072, AAD28251) as well as the alignment results with WP1 whole genome sequence (sequencing by JGI and is available online) with the following modifications.

The genome sequence of WP1 was provided through the DOE Joint Genome Institute sequencing effort (see Acknowledgements). Putative XYL1 and XYL2 genes were first found in the JGI sequence using BLAST and the resulting sequences were utilized to design primers for the cloning of the mRNA sequences of the two genes from WP1. Sequence comparisons of the cloned genes with public databases were performed via the Internet at the National Center for Biotechnology Information site (http://www.ncbi.nlm.nih.gov/), by employing the tblast algorithm (Altschul et al. 1997). GenomeScan (Chris Burge, Biology Dept. at MIT http://genes.mit.edu/genomescan.html) was employed to predict the gene exon/intron structures and putative XR and XDH mRNA sequences in WP1. All the resulting sequences in WP1 and PTD3 were aligned with homologous protein sequences of other D-xylose-fermenting yeasts (e.g. *Pichia stipitis, Candida*. spp) using the local BLAST program (Bl2seq).

The resulting PCR products were purified using the QIAEXII gel extraction kit (Qiagen, Madison, Wis.) and then inserted into the pGEM-T Easy vector (Promega, Madison, Wis.) following the manufacturer's instructions. Sequencing of the inserts in both directions was performed by the UW Biochemistry Department Sequencing Facility using the BigDye Terminator v3.1 Cycle sequencing kit (Applied Biosystems).

TABLE 4

Primers used for cloning of the XR and XDH-encoding genes from WP1 and PTD3and in expression studies thereof.

| Primer | Sequence | SEQ ID NO: |
| --- | --- | --- |
| WP1-XR-F | ATGGTCCAGACTGTCCCC | 19 |
| WP1-XR-R | TCAGTGACGGTCGATAGAGATC | 20 |
| WP1-XDH-F | ATGAGCGCTCCCAGTCTCGC | 21 |
| WP1-XDH-R | TCACTCGAGCTTCTCGTCGAC | 22 |
| PTD3-D-XR-F | GCYATCAAGKCGGGYTACCG | 23 |
| PTD3-D-XR-R | GTGGWAGBTGTTCCASAGCTT | 24 |
| PTD3-D-XDH-F | CCMATGGTCYTSGGNCACGA | 25 |
| PTD3-D-XDH-R | CCGACVGGVCCDGCDCCAAAGAC | 26 |
| PTD3-XR-GSP1 (for 5' RACE) | GCCAGTGGATGAGGTAGAGG | 27 |
| PTD3-XR-GSP2 (for 5' RACE) | GTGATGAAGATGTCCTTGCG | 28 |
| PTD3-XR-GSP3 (for 3' RACE) | AGGTCTACGGCAACCAGAAG | 29 |
| PTD3-XR-GSP4 (for 3' RACE) | ATCACCTCGAAGCTCTGGAAC | 30 |

TABLE 4-continued

Primers used for cloning of the XR and XDH-encoding genes from WP1 and PTD3and in expression studies thereof.

Figure 35A:
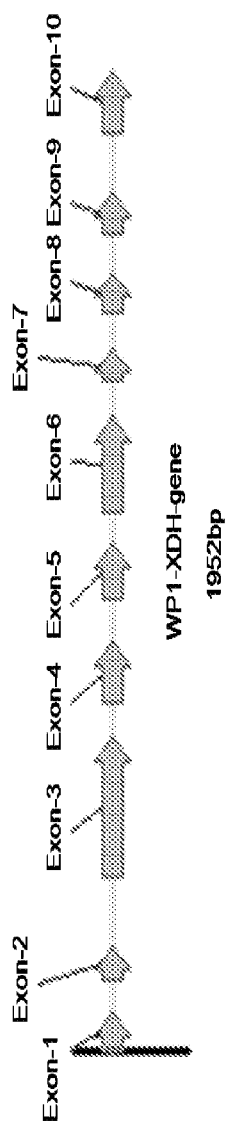
FIG. 35. Exon/Intron structures of the XR (A) and XDH-(B) encoding genes of *Rhodotorula graminis* strain WP1.
Figure 35B:
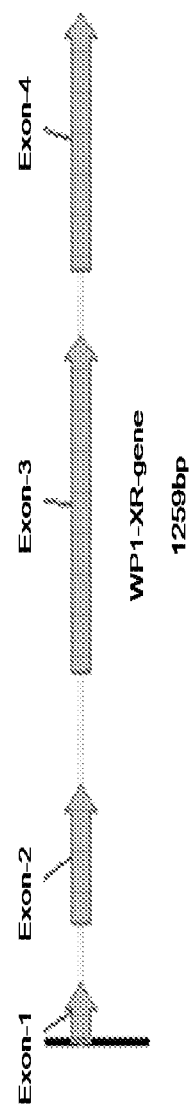
Figure 36A:
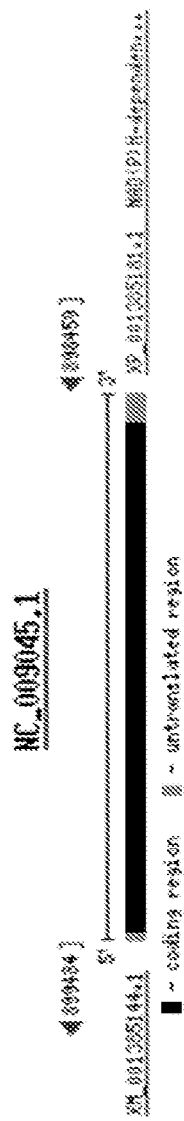
FIG. 36. Exon/Intron structures of the XR (A) and XDH-(B) encoding genes of *Pichia stipitis*.
Figure 36B:
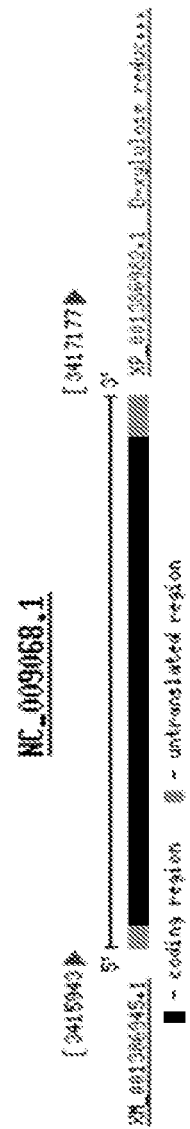

| Primer | Sequence | SEQ ID NO: |
| --- | --- | --- |
| PTD3-XDH-GSP1 (for 5' RACE) | GATGAGCGATTTGAGGTTGAC | 31 |
| PTD3-XDH-GSP2 (for 5' RACE) | CCTTGGCAACTGCGTGGAC | 32 |
| PTD3-XDH-GSP3 (for 3' RACE) | GCAAAGGTGGTCATTACGAAC | 33 |
| PTD3-XDH-GSP4 (for 3' RACE) | CTCCTTGAGCCCATGTCGGT | 34 |
| #XR-F | ATCACCTCGAAGCTCTGGAAC | 35 |
| #XR-R | GCCAGTGGATGAGGTAGAGG | 36 |
| #XDH-F | CTCCTTGAGCCCATGTCGGT | 37 |
| #XDH-R | GATGAGCGATTTGAGGTTGAC | 38 |
| 515F (18S rRNA) | GTGCCAAGGCAGCCGCGGTAA | 39 |
| 1209R (18S rRNA) | GGGCATCACAGACCTG | 40 | note: K = G/T V = A/C/G M = A/C N = A/C/G/T R = A/G B = C/G/T S = C/G W = A/T Y = C/T D = A/T/G The XR and XDH-encoding genes were cloned and sequenced from WP1 using primers based on the genomic sequence of WP1 provided by the DOE JGI sequencing project. Analysis of the two genes was then performed on the cloned sequences (not directly from the JGI sequences provided). The 1259 nucleotide sequence of WP1-XR contains an open reading frame of 966 nucleotides (SEQ ID NO:41) encoding a polypeptide of 321 amino acids (SEQ ID NO:42). The 1216 nucleotide sequence of WP1-XDH contains an open reading frame of 1191 nucleotides (SEQ ID NO:43) encoding a polypeptide of 396 amino acids (SEQ ID NO:44). At the amino acid level, the WP1-XR gene is 37% and 36% identical to XYL1 gene of *Pichia stipitis* (XP_001385181) and *Candida guilliermondii* (O94735), respectively; the WP1-XDH gene is slightly more conserved: 41% identity to XYL2 gene of *Pichia stipitis* (XP_001386982) and *Candida tropicalis*. The visualized annotation pictures (by using vector NTI10) of the two genes show that both XR and XDH genes are more complex than those of *Pichia stipitis* which has no introns in the genes (FIGS. 35 and 36) (Amore et al. 1991).

Example 10

WP1 XR and XDH Gene Expression Levels in Glucose and Xylose

Figure 37A:
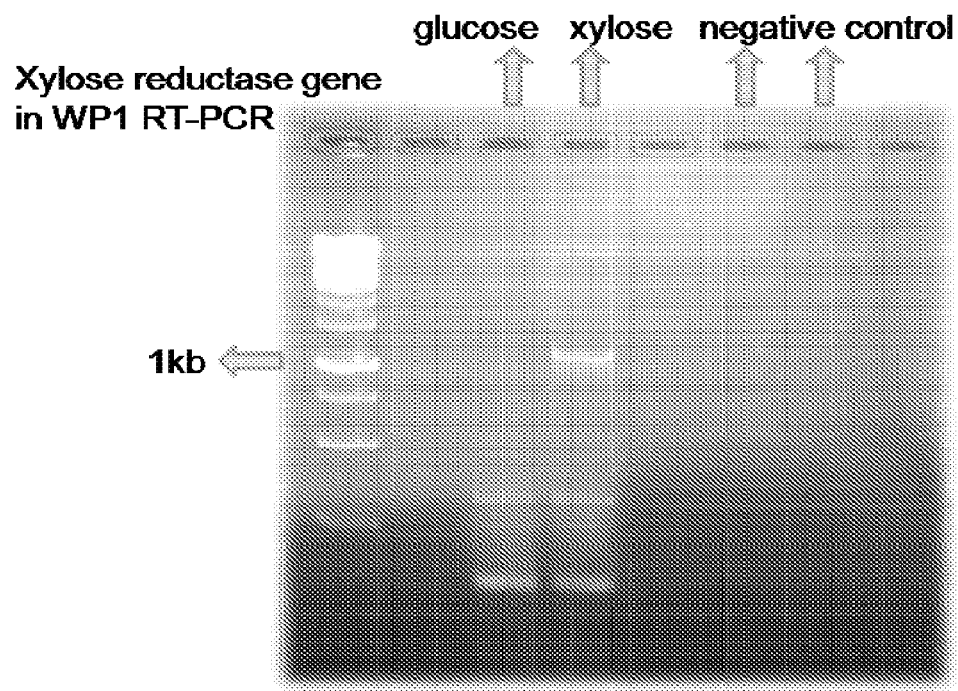
FIG. 37. Amplification of WP1 XR mRNA (A) and XDH mRNA (B) from cells grown in glucose or xylose. The first lane is a Fermentas 1 kb DNA ladder. RNA templates directly subjected to a regular PCR (without reverse transcriptase) served as negative controls for both genes. The 1 kb bands were cloned and the sequences were verified to be XR and XDH-encoding genes.
Figure 37B:
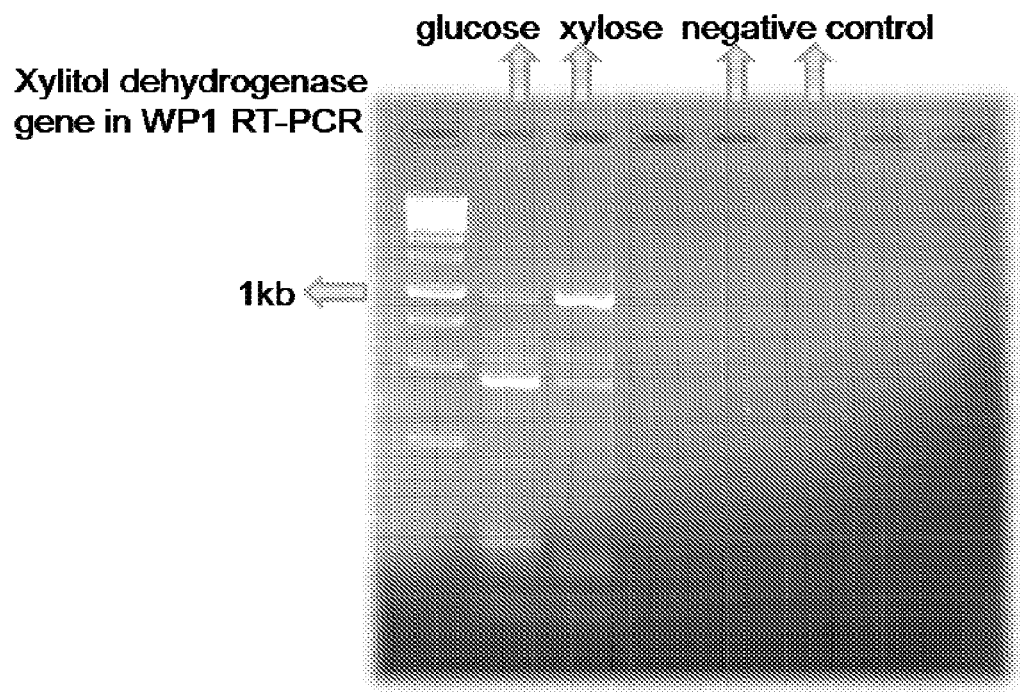

To investigate the XR and XDH gene expression in WP1, cells were grown in medium containing either glucose or xylose, and the RNA was purified from the cultures. Segments from the mRNA were amplified using RT-PCR with primers specific for each of the two genes. As shown in FIG. 37, the XR and XDH genes were expressed in WP1 cells grown in xylose. These results indicated that the genes are indeed transcribed and that XR and XDH gene expression was upregulated by xylose. The XR gene expression was not detectable when the cells were grown in glucose; however, there was some low-level constitutive expression of the XDH in glucose.

Briefly, total RNA was isolated from cells grown in media containing 2% glucose, 2% xylose, 1% glucose+1% xylose or 2% glucose+2% xylose respectively. RT-PCR was applied on the same amount of total RNAs from different media using the primer sets #XR-F, #XR-R and #XDH-F, #XDH-R (Table 4) designed to work equally well for both WP1 and PTD3. To verify that the same amount of total RNA was used, 18S rRNA semiquantitative RT-PCR was performed in WP1 under these different culture conditions using primer set 515F and 1209R (downloaded from JGI for eukaryotic 18S rRNA gene amplification).

Example 11

Cloning of the Xylose Reductase (XR) and Xylitol Dehydrogenase (XDH) Encoding Genes XYL1 and XYL2 from PTD3

For cloning the partial XR and XDH-encoding genes in PTD3 (genome sequences are not available), RT-PCR was performed using the degenerate primers PTD3-D-XR-F, PTD3-D-XR-R and PTD3-D-XDH-F, PTD3-D-XDH-R, which were designed based on the multiple sequence alignment amongst PTD3, WP1 and other D-xylose-fermenting yeasts (CLUSTALW, Thompson et al. 1994). Following RT-PCR, samples were subjected to electrophoresis in a 1% agarose gel, using Sybersafe (Invitrogen) as a DNA intercalating and visualizing agent, at 100V for 1 hour.

Since strain PTD3 was a more effective utilizer of xylose compared to WP1, the xylose metabolism genes where cloned from this strain. However, the PTD3 genome has not been sequenced, so a different approach was used to clone the two genes than was used for WP1. The partial PTD3 XR and XDH-encoding genes were cloned using degenerate primer sets that were designed based on the multiple sequence alignment amongst PTD3, WP1 and other D-xylose-fermenting yeasts (Table 4). The complete nucleotide sequences were subsequently determined by 5' and 3' rapid amplification of cDNA ends (RACE) using gene specific primers based on the cDNA fragment sequences. Briefly, the partial PTD3 XR and XDH-encoding genes were amplified by RT-PCR and sequenced, and the complete nucleotide sequences were subsequently determined by 5' and 3' rapid amplification of cDNA ends (RACE) using a 5'/3' RACE kit (FirstChoice RLM-RACE Kit, Applied Biosystems). For 5'RACE, the gene-specific primers PTD3-XR-GSP1, PTD3-XR-GSP2, PTD3-XDH-GSP1 and PTD3-XDH-GSP2 were used. For 3' RACE, the gene-specific primer PTD3-XR-GSP3, PTD3-XR-GSP4, PTD3-XDH-GSP3 and PTD3-XDH-GSP4 were used. Primer sequences are listed in Table 4.

The 1087 bp nucleotide sequence of the cloned PTD3-XR contained an open reading frame of 975 bp nucleotides (SEQ ID NO:45) encoding a polypeptide of 324 amino acids (SEQ ID NO:46). The alignment results show that PTD3-XR protein is 67% identical to the WP1 XR protein (Table 5). The 1409 bp nucleotide sequence of PTD3-XDH contains an open reading frame of 1185 bp nucleotides (SEQ ID NO:47) encoding a polypeptide of 394 amino acids (SEQ ID NO:48). The alignment results showed that PTD3-XDH protein is 69% identical to the WP1 XDH protein. Alignments with other yeasts were also performed to study the homology with the two genes in PTD3 (Table 5). The XR and XDH proteins of WP1 and PTD3 were 69-73% identical, whereas they are only 37-41% identical to these proteins from other known xylose-utilizing species.

TABLE 5

XR and XDH identities between homologous proteins in several yeast strains. GenBank Accession No.: XR: CAA42072 (*P. stipitis*); ABX60132 (*C. tropicalis*); AAD09330 (*C. guilliermondii*). XDH: AAD28251 (*P. stipitis*); ABB01368 (*C. tropicalis*). The XDH protein sequence of *Candida guilliermondii* was unavailable.

| Identity | WP1 | Pichia stipitis | Candida guilliermondii | Candida tropilis |
|---|---|---|---|---|
| PTD3 XR | 73% | 38% | 37% | 39% |
| PTD3 XDH | 69% | 37% | Null | 41% |

Example 12

PTD3 XR and XDH Gene Expression Levels in Glucose and Xylose

Figure 38:
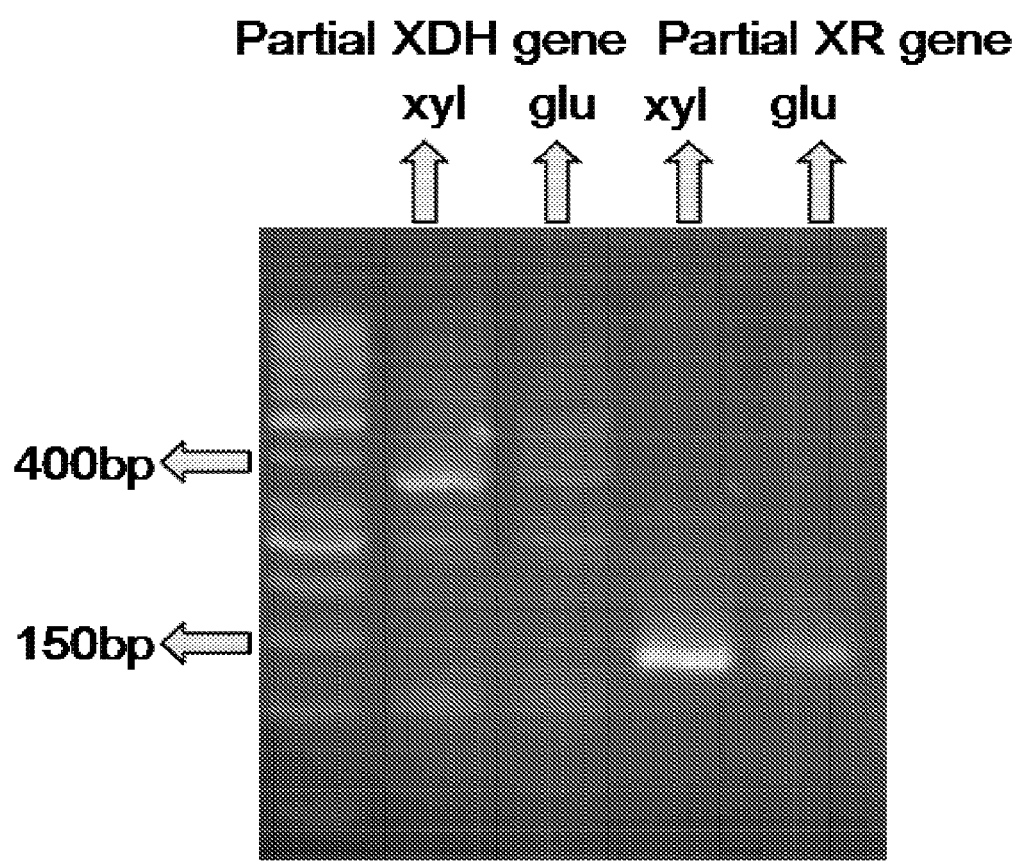
FIG. 38. Amplification of PTD3 XDH mRNA and XR mRNA from cells grown in glucose ("glu") or xylose ("xyl"). The first lane is a Fermentas 100 bp DNA ladder.

To investigate the expression of the two genes in PTD3, cells were grown in glucose and xylose media as with the WP1 study. PTD3 gene specific primers were used to amplify the segments from mRNA by using RT-PCR. Different bands corresponding to XR and XDH were observed in mRNA from cells grown on either glucose or xylose (FIG. 38). These results indicate that the genes are indeed transcribed within mRNA and that the XR and XDH gene expression was induced by xylose. As in WP1, the genes were barely expressed in medium containing only glucose as the carbon source.

Example 13

Comparison of the Gene Expression Levels of XR and XDH Between WP1 and PTD3

Figure 39:
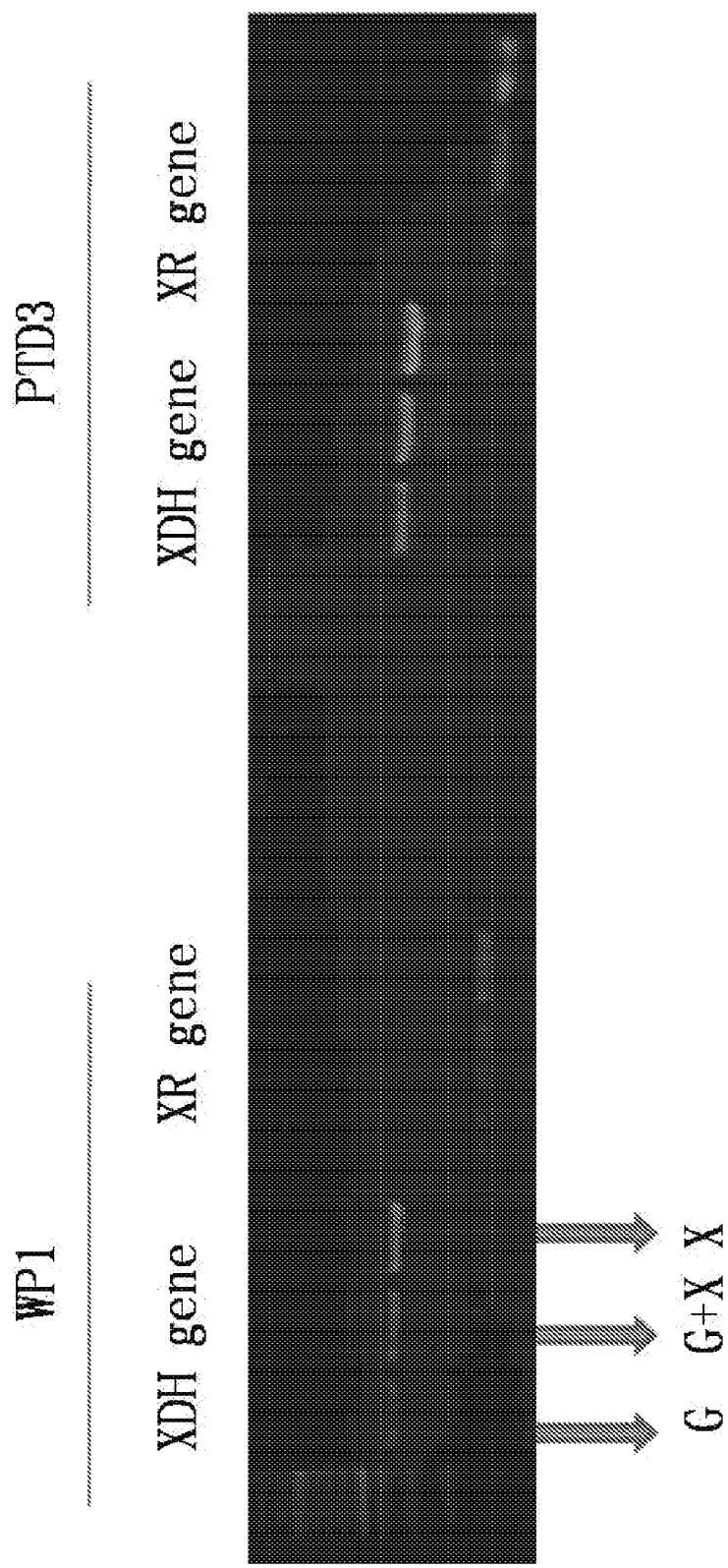
FIG. 39. WP1 and PTD3 XR/XDH gene expressions from cells grown in 2% glucose (lanes 1, 4, 7, 10), 1% glucose+ 1% xylose (lane 2, 5, 8, 11), and 2% xylose (lanes 3, 6, 9, 12). Lane 1-6: WP1 gene expression; Lane 7-12: PTD3 gene expression.

In order to better understand the differences in utilization of xylose between the two endophytic yeast strains, the expression levels of the XR and XDH genes were compared between the strains. Using the aligned WP1 and PTD3 sequences, primers were designed to the gene regions of identity so that the expression of XR and XDH-encoding genes could be directly comparable. RT-PCR was performed to amplify the mRNA segments from WP1 and PTD3 cells grown in YP medium containing different sugars (2% glucose, 2% xylose, 1% glucose+1% xylose, 2% glucose+2% xylose). As shown in FIG. 39, both the XDH and XR genes are expressed to higher levels in PTD3 than in WP1 when the yeast were grown in xylose medium. The expression of the two genes appeared slightly suppressed in 1% xylose+1% glucose medium compared to 2% xylose medium.

Figure 40A:
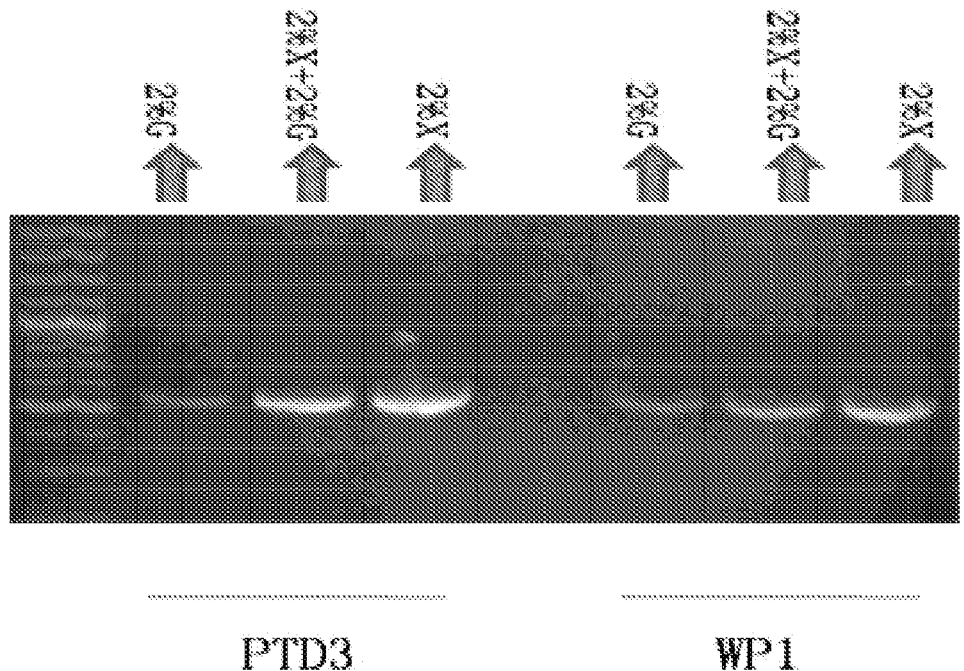
FIG. 40. WP1 and PTD3 XR (A)/XDH (B) gene expressions from cells grown in 2% glucose, 2% xylose and 2% glucose+2% xylose. RNA templates used in different conditions were labeled in the figure.
Figure 40B:
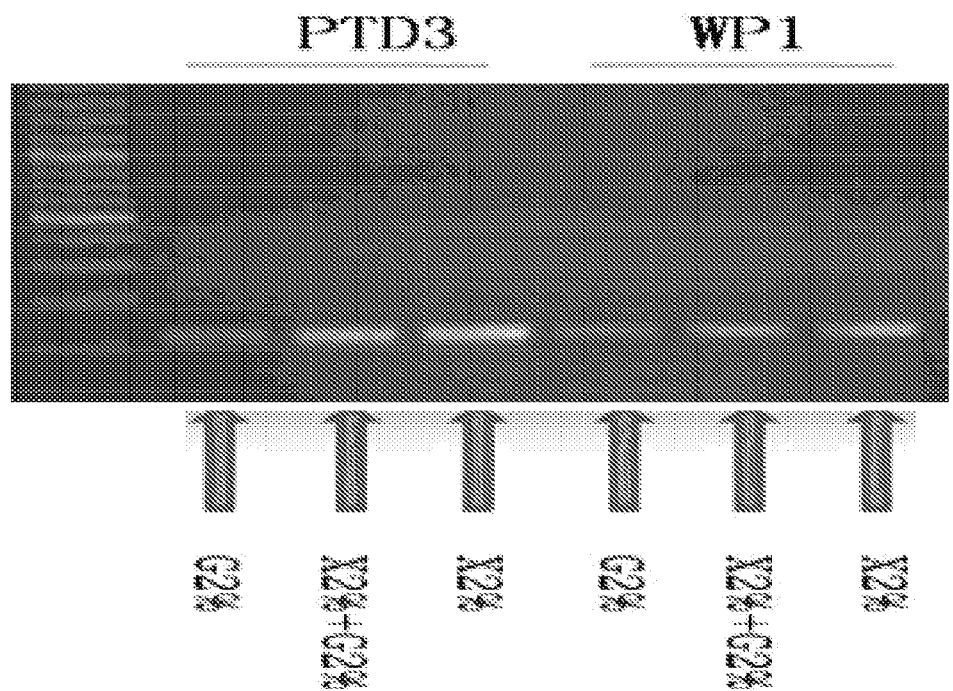
Figure 41:
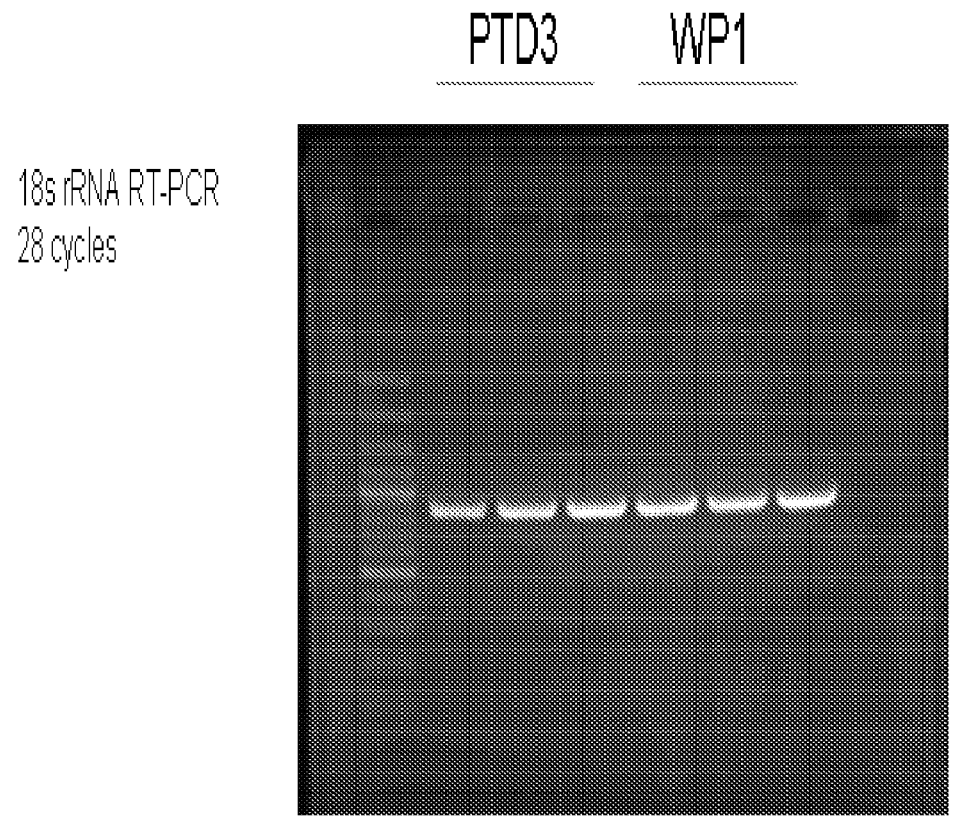
FIG. 41. WP1 and PTD3 XR/XDH gene 18S rRNA RT-PCR from cells grown in 2% glucose (lanes 1, 3), 2% glucose+2% xylose (lanes 2, 4) and 2% xylose (lanes 3, 6) medium. Lane S is a Fermentas 1 kb DNA ladder.
Figure 43B:
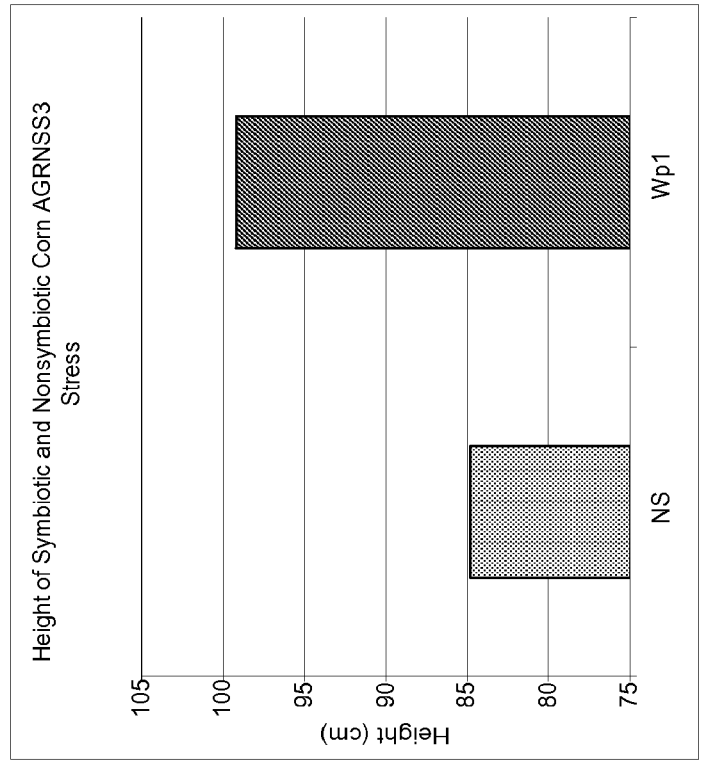
FIG. 43. Greenhouse studies with corn (line3) that were either NS=nonsymbiotic (uninoculated control) or symbiotic (N=9) with *Rhodotorula* sp. WP1 in the absence of stress. The biomass, yields (A) and heights (B) of plants were assessed, and WP1 colonized plants were found to be larger and produced higher yields (ears) than NS plants. (P≤0.004). N=9; SE≤0.21, 0.56, and 0.27 for biomass, yields, and heights, respectively.
Figure 43A:
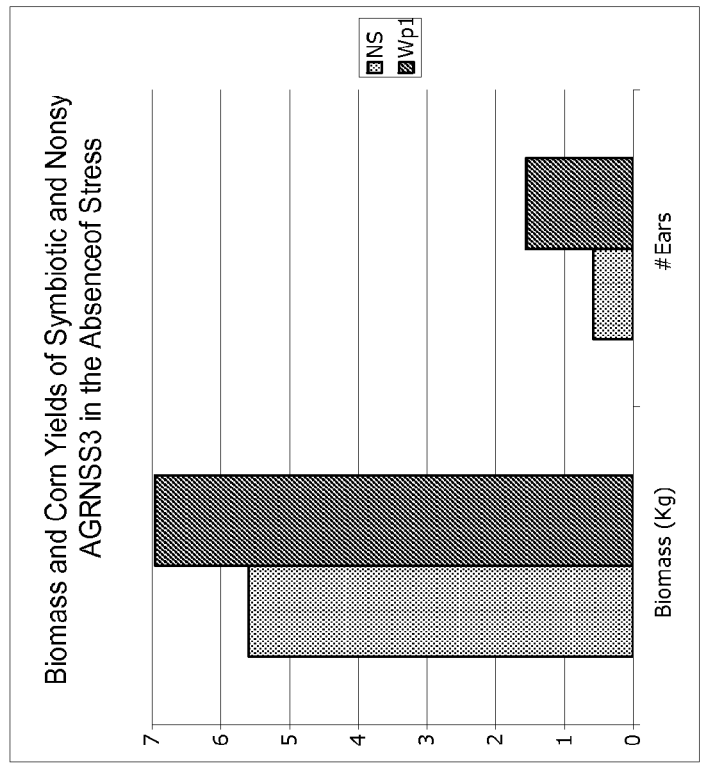

In order to investigate whether the expression differences resulted from the lower xylose concentration in the mixed sugar medium or from repression by glucose, an RT-PCR experiment was also conducted under 2% glucose+2% xylose culture condition. As shown in (FIG. 40) in WP1, the expression of the two genes were still slightly suppressed in 2% xylose+2% glucose medium compared to 2% xylose medium. However, the gene expression was not suppressed by glucose in PTD3. In this strain, the level of the XR and XDH gene expression was about equal in both the mixed sugar medium and the xylose medium. 18S rRNA RT-PCR was performed as an internal control showing that equal amounts of total RNA were used under these different culture conditions (FIG. 41).

Example 14

Nitrogen Fixation of Endophytic Yeast

Figure 33:
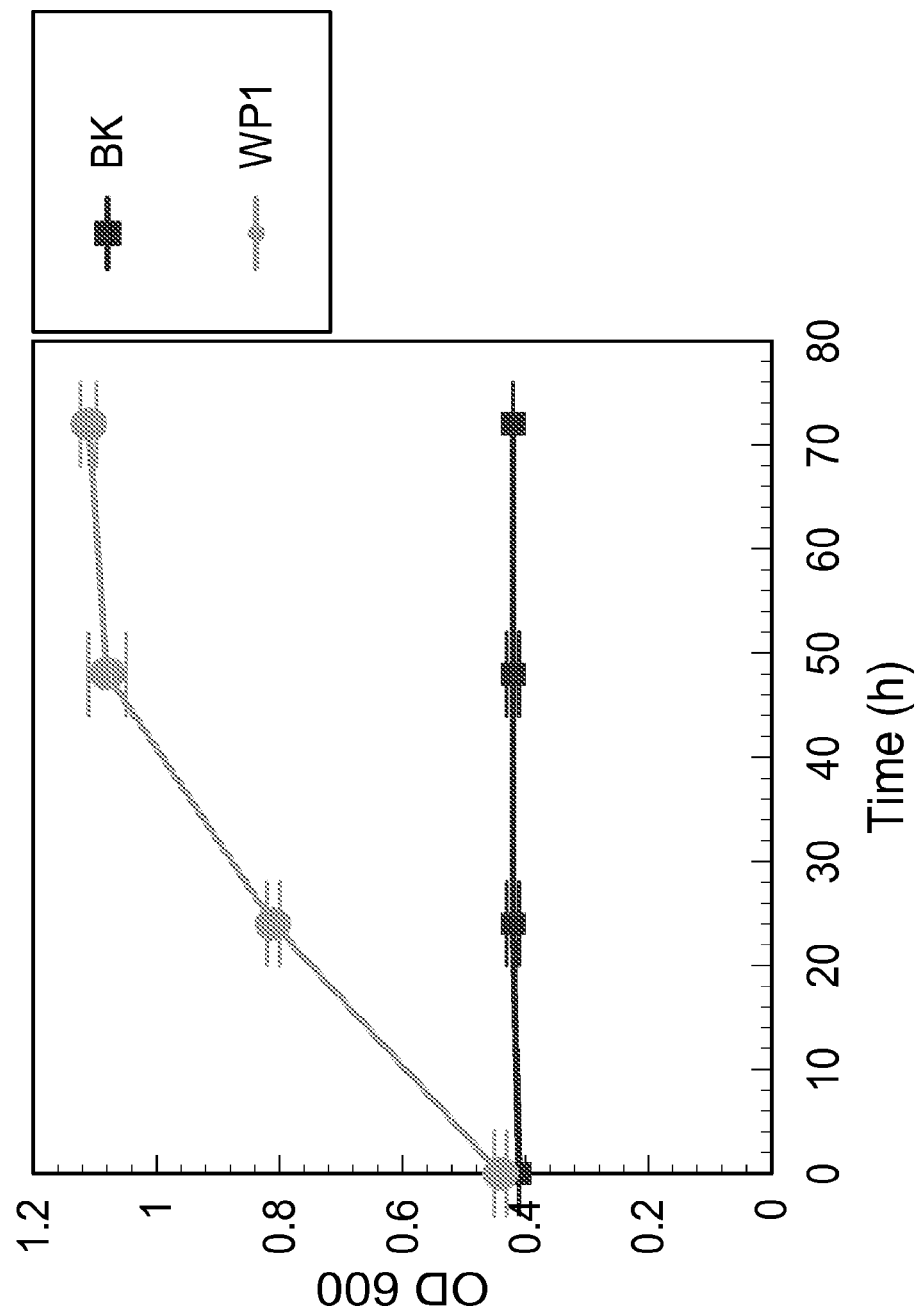
FIG. 33. Growth curve of *Rhodotorula graminis* strain WP1 and *Saccharomyces cerevisiae* (ATCC strain #6037) in nitrogen-free MS medium (Caisson) containing dextrose and mannitol. Growth in three flasks of each strain was monitored for 3 days. The experiment was repeated with similar results.

To determine if any of the isolated endophytic yeast strains could fix atmospheric nitrogen, several isolated strains were incubated in nitrogen limiting media (NFM). Surprisingly, it was found that WP1, as well as two other pink yeasts isolated from greenhouse-grown poplar hybrids, were among the endophytes that grew well on NFM. Amplification of the nifH gene using universal primers indicated that these isolates contain the nitrogenase gene required for nitrogen fixation. FIG. 33 shows the growth of WP1 and *Saccharomyces cerevisiae* (baker's yeast) in NFM as quantified by OD600. These results suggest that the isolated endophytic yeast strains provided herein are able to fix atmospheric nitrogen.

Example 15

Use of Endophytic Yeast for Nitrogen Fixation and Supplementation of Nitrogen Deficiencies for Plant Growth To determine if nitrogen fixing yeast could be used to promote plant growth under nitrogen limiting conditions, corn was grown for 11 weeks in soil without nitrogen supplementation in the presence (WP1) or absence (non-symbiotic; NS) or the nitrogen fixing strain WP1. As seen in FIG. 42, corn grown in the presence of the WP1 yeast strain consistently grew much more robustly, providing about 5 times more biomass (B(g)) than corn grown in the absence of WP1 (compare FIG. 42B with FIG. 42A, respectively). In addition, the % viability in WP1 colonized plants (58-92%) was higher than uninoculated plants (8.3-29.2%) plants. Statistical analysis indicated significant differences ($P \leq 0.1$) for both viability and biomass with WP1 symbiotic plants having higher viability and biomass compared to uninoculated plants. A graphic representation of these data are provided in FIG. 44. Thus, nitrogen fixing endophytic yeast strains isolated from within poplar trees can significantly promote the growth of corn, even in the absence of traditional nitrogen sources. As such, these yeast can be used for biological nitrogen fixation instead of chemical fertilizers to lower costs and reduce nitrous oxide emissions into the atmosphere.

REFERENCES

Altschul S F, Madden T L, Schaffer A A, Zhang J, Zhang Z, Miller W, and Lipman D J (1997) Gapped BLAST and PSI-BLAST: a new generation of protein database search programs. Nucleic Acids Research 25: 3389-3402.

Amore R, Kotter P, Kuster C, Ciriacy M, and Hollenberg C P (1991) Cloning and expression in *Saccharomyces cerevisiae* of the NAD(P)H-dependent xylose reductase-encoding gene (XYL1) from the xylose-assimilating yeast *Pichia stipitis*. Gene 109: 89-97.

Aristidou A and Penttila M (2000) Metabolic engineering applications to renewable resource utilization. Curr Opin Biotechnol 11: 187-198.

Ausubel F, Brent R, Kingston R E, Moore D D, Seidman J G, Smith J A, Struhl K, 1995. Short Protocols in Molecular Biology, John Wiley & Sons, Hoboken, N.J.

Balsalobre L, De Siloniz M I, Valderrama M J, Benito T, Larrea M T, Peinado J M, 2003. Occurrence of yeasts in municipal wastes and their behavior in presence of cadmium, copper and zinc. Journal of Basic Microbiology 43: 185-193.

Barbosa M F S, Medeiros M B, de Mancilha I M, Schneider H, and Lee H (1988) Screening of yeasts for production of xylitol from D-xylose and some factors which affect xylitol yield in *Candida guilliermondii*. J Ind Microbiol 3: 241-251.

Barnett J A, Payne R W, Yarrow D, 2000. Yeasts: Characteristics and Identification, Cambridge University Press, Cambridge, UK.

Bichio P A, Runnals P L, Cunningham J D, and Lee H (1988) Induction of xylose reductase and xylitol dehydrogenase activities in *Pachysolen tannophilus* and *Pichia stipitis* on mixed sugars. Appl Environ Microbiol 54: 50-54.

bioMerieux, 2007. API 20C AUX Yeast Identification System User Manual. bioMerieux, Inc., Marcy l'Etoile, France.

Boekhout T, 1991. A revision of ballistoconidia-forming yeasts and fungi. Studies in Mycology 33: 1-194.

Borges Y S A (1991) Sugar substitutes in the prevention of dental caries: review of the literature. Pract Odontol 12: 59-60.

Botes A, Todorov S D, von Mollendorff J W, Botha A, Dicks L M T, 2007. Identification of lactic acid bacteria and yeast from Boza. Process Biochemistry 42: 267-270.

Brown C L, Graham S M, Cable B B, Ozer E Z, Taft P J, and Zabner J (2004) Xylitol enhances bacterial killing in the rabbit maxillary sinus. Laryngoscope 114: 2021-2024.

Bruinenberg P M and van Dijken J P (1983) An enzymatic analysis of NAPDH production and consumption in *Candida utilis*. J Gen Microbiol 129: 965-971.

Burke D, Dawson D, and Stearns T (2000) Methods in Yeast Genetics. Cold Spring Harbor Laboratory Press, Cold Spring Harbor.

Cao L X, You J L, Zhou S N, 2002. Endophytic fungi from *Musa* acuminata leaves and roots in South China. World Journal of Microbiology & Biotechnology, 18: 169-294 171.

de Siloniz M I, Payo E M, Callejo M A, Marquina D, Peinado J M, 2002. Environmental adaptation factors of two yeasts isolated from the leachate of a uranium mineral heap. FEMS Microbiology Letters 210: 233-237.

di Menna M E, 1958. Two new species of yeasts from New Zealand. Journal of General Microbiology 18: 269-272.

Doty S L, Dosher M R, Singleton G L, Moore A L, van Aken B, Stettler R F, Strand S E, Gordon M P, 2005. Identification of an endophytic *Rhizobium* in stems of *Populus*. Symbiosis 39: 27-35. Doty, S. L., Oakley, B., Xin, G., Kang, J. W., Singleton, G., Khan, Z., Vajzovic, A., and Staley, J. T. 2009. Diazotrophic endophytes of native black cottonwood and willow. Symbiosis Vol 47: 23-33.

Du Preez J C (1994) Process parameters and environmental factors affecting D-xylose fermentation by yeasts. Enzyme Microb Technol 16: 944-956.

Durham D R, McNamee C G., Stewart D B, 1984. Dissimilation of aromatic compounds in *Rhodotorula graminis*: biochemical characterization of pleiotropically negative mutants. Journal of Bacteriology 160: 771-777.

Eck R V, Dayhoff M D, 1966. Atlas of Protein Sequence and Structure, National Biomedical Research Foundation, Silver Springs, Md.

El-Tarabily K A, 2004. Suppression of *Rhizoctonia solani* diseases of sugar beet by antagonistic and plant growth-promoting yeasts. Journal of Applied Microbiology 312 96: 69-75.

Fell J W, Boekhout T, Fonseca A, Scorzetti G, Statzell-Tallman A, 2000. Biodiversity and systematics of Basidiomycetous yeasts as determined by large-subunit rRNA gene D1/D2 domain sequence analysis. International Journal of Systematic and Evolutionary Microbiology 50: 1351-1371.

Freer S N, Skory C D, and Bothast R J (1997) D-Xylose metabolism in *Rhodosporidium toruloides*. Biotechnol Lett 19: 1119-1122.

Gadanho M, Sampaio J P, 2002. Polyphasic taxonomy of the Basidiomycetous yeast genus *Rhodotorula*: *Rh. glutinis* sensu stricto and *Rh. dairenensis* comb. nov. FEMS Yeast Research 2: 47-58.

Germaine K J, Liu X M, Cabellos G G, Hogan J P, Ryan D, Dowling D N, 2006. Bacterial endophyte-enhanced phytoremediation of the organochlorine herbicide 2,4-dichlorophenoxyacetic acid. FEMS Microbiology Ecology 57: 302-310.

Gong C S, Chen L F, and Tsao G T (1981) Quantitative production of xylitol from D-xylose by a high xylitol producing yeast mutant *Candida tropicalis* HPX 2. Biotechnol Lett 3: 125-130.

Gordon S A, Weber R P, 1951. Colorimetric estimation of indolacetic acid. Plant Physiology 26: 192-195.

Haridy M S A, 1993. Occurrence of yeasts in yogurt, cheese and whey. Cryptogamie Mycologie 14: 255-262.

Hobbie E A, Watrud L S, Maggard S, Shiroyama T, Rygiewicz P T, 2003. Carbohydrate use and assimilation by litter and soil fungi assessed by carbon isotopes and biolog (R) assays. Soil Biology & Biochemistry 35: 303-311.

Hrazdina G, Jensen R A, 1992. Spatial-organization of enzymes in plant metabolic pathways. Annual Review of Plant Physiology and Plant Molecular Biology 43: 241-267.

James S A, Collins M D, Roberts I N, 1996. Use of an rRNA gene internal transcribed spacer region to distinguish phylogenetically closely related species of the genera *Zygosaccharomyces* and *Torulaspora*. International Journal of Systematic Bacteriology 46: 189-194.

Jeffries T W (1983) Utilization of xylose by bacteria, yeasts, and fungi. Adv Biochem Eng Biotechnol 27: 1-32.

Jeffries T W, Grigoriev I V, Grimwood J, Laplaza J M, Aerts A, Salamov A, Schmutz J, Lindquist E, Dehal P, Shapiro H, Jin Y S, Passoth V, and Richardson P M (2007) Genome sequence of the lignocellulose-bioconverting and xylose-fermenting yeast *Pichia stipitis*. Nat Biotechnol 25: 319-326.

Jukes T H, Cantor C R, 1969. Evolution of protein molecules. In: Munro H N, (eds), Mammalian Protein Metabolism, Academic Press, New York, N.Y., pp. 21-132.

Kaiser C, Michaelis S, and Mitchell A (1994) Methods in Yeast Genetics: A Cold Spring Harbor Course Manual. Cold Spring Harbor Laboratory Press, Cold Spring Harbor.

Kotik M, Brichac J, Kyslik P, 2005. Novel microbial epoxide hydrolases for biohydrolysis of glycidyl derivatives. Journal of Biotechnology 120: 364-375.

Kurtzman C P, Robnett C J, 1998. Identification and phylogeny of ascomycetous yeasts from analysis of nuclear large subunit (26S) ribosomal DNA partial sequences. Antonie Van Leeuwenhoek International Journal of General and Molecular Microbiology 73: 331-371.

Kurtzman C P, Robnett C J, 2003. Phylogenetic relationships among yeasts of the '*Saccharomyces* complex' determined from multigene sequence analyses. FEMS Yeast Research 3: 417-432.

Laplaza J M, Torres B R, Jin Y-S, and Jeffries T W (2006) Sh ble and Cre adapted for functional genomics and metabolic engineering of *Pichia stipitis*. Enzyme Microb Technol 38: 741-747.

Larran S, Monaco C, Alippi H E, 2001. Endophytic fungi in leaves of *Lycopersicon esculentum* mill. World Journal of Microbiology & Biotechnology 17: 181-184.

Larran S, Perello A, Simon M R, Moreno V, 2002. Isolation and analysis of endophytic microorganisms in wheat (*Triticum aestivum* L.) leaves. World Journal of Microbiology & Biotechnology 18: 683-686.

Lee Y Y, Lin C M, Johnson T, and Chambers R P (1979) Selective hydrolysis of hardwood hemicellulose by acids. Biotechnol Bioeng Symp 8: 75-88.

Lin S-L, Miller J D, and Ying S-Y (2010) Intronic microRNA (miRNA). J Biomed Biotechnol 26818.

Lodewyckx C, Taghavi S, Mergeay M, Vangronsveld J, Clijsters H, van der Lelie D, 2001. The effect of recombinant heavy metal resistant endophytic bacteria in heavy metal uptake by their host plant. International Journal of Phytoremediation 3: 356 173-187.

Meyrial V, Delgenes J P, Moletta R, and Navarro J M (1991) Xylitol production from D-xylose by *Candida guilliermondii*. Biotechnol Lett 11: 281-286.

Middelhoven W J, 1993. Catabolism of benzene compounds by Ascomycetous and Basidiomycetous yeasts and yeast-like fungi—a literature review and an experimental approach. Antonie Van Leeuwenhoek International Journal of General and Molecular Microbiology 63: 125-144.

Middelhoven W J, Koorevaar M, Schuur G W, 1992. Degradation of benzene compounds by yeasts in acidic soils. Plant and Soil 145: 37-43.

Milligan G W, 1980. An examination of the effect of six types of error perturbation on fifteen clustering algorithms. Psychometrika 45: 325-342.

Nassar A H, El-Tarabily K A, Sivasithamparam K, 2005. Promotion of plant growth by an auxin-producing isolate of the yeast *Williopsis saturnus* endophytic in maize (*Zea mays* L.) roots. Biology and Fertility of Soils 42: 97-108.

Neofytos D, Horn D, de Simone J A, 2007. *Rhodotorula mucilaginosa* catheter-related fungemia in a patient with sickle cell disease: case presentation and literature review. Southern Medical Journal 100: 198-200.

Ojama H (1994) Yeast xylose metabolism and xylitol production. Helsinki University of Technology.

Passon C (1993) Xylitol: a sugar that fights tooth decay. J Colo Dent Assoc 71: 19-23.

Pavlova K, Grigorova D, Hristozova T, Angelov A, 2001. Yeast strains from Livingston Island, Antarctica. Folia Microbiologica 46: 397-401.

Petrini, O. (1991). Fungal endophytes of tree leaves. In: Andrews J H, Hirano S S, (eds), Microbial Ecology of Leaves, Springer, New York, pp. 179-197.

Pizzo G, Giuliana G, Milici M E, and Giangreco R (2000) Effect of dietary carbohydrates on the in vitro epithelial adhesion of *Candida albicans, Candida tropicalis*, and *Candida krusei*. New Microbiol 23: 63-71.

Radwanski E R, Last R L, 1995. Tryptophan biosynthesis and metabolism-biochemical and molecular-genetics. Plant Cell 7: 921-934.

Ramani R, Gromadzki S, Pincus D H, Salkin I F, Chaturvedi V, 1998. Efficacy of API 20C and ID 32C systems for identification of common and rare clinical yeast isolates. Journal of Clinical Microbiology 36: 3396-3398.

Romero M C, Hammer E, Cazau M C, Arambarri A M, 2002. Isolation and characterization of biarylic structure-degrading yeasts: hydroxylation potential of dibenzofuran. Environmental Pollution 118: 379-382.

Ryan R P, Germaine K, Franks A, Ryan D J, Dowling D N, 2008. Bacterial endophytes: recent developments and applications. FEMS Microbiology Letters 278: 1-9.

Saitou N, Nei M, 1987. The neighbor joining method—a new method for reconstructing phylogenetic trees. Molecular Biology and Evolution 4: 406-425.

Sakai T, Hamakawa M, and Kubo S (1996) Glucose and xylitol tolerance tests for ketotic and healthy dairy cows. J Dairy Sci 79: 372-377.

Salminen E K, Salminen S J, Porkka L, Kwasowski P, Marks V, and Koivistoinen P E (1989) Xylitol vs glucose: effect on the rate of gastric emptying and motilin, insulin, and gastric inhibitory polypeptide release. Am J Clin Nutr 49: 1228-1232.

Schneider H (1989) Conversion of D-xylose to ethanol by yeasts and fungi. CRC Crit. Rev biotechnol 9: 1-40.

Scorzetti G., Fell J W, Fonseca A, Statzell-Tallman A, 2002. Systematics of Basidiomycetous yeasts: a comparison of large subunit D1/D2 and internal transcribed spacer rRNA gene regions. FEMS Yeast Research 2: 495-517.

Skoog K and Hahn-Hagerdal B (1988) Xylose fermentation. Enzyme Microb Technol 10: 66-80.

Smith D R and Lee R W (2008) Nucleotide diversity in the mitochondrial and nuclear compartments of *Chlamydomonas reinhardtii*: investigating the origins of genome architecture. BMC Evol Biol 8: 156.

Spencer D M, Spencer J F T, Fengler E, Defigueroa L I, 1995. Yeasts associated with algarrobo trees (*Prosopis* spp.) in Northwest Argentina—a preliminary report. Journal of Industrial Microbiology 14: 472-474.

Sugai J K and Delgenes J P (1995) Catabolite repression of induction of aldose reductase activity and utilization of mixed hemicellulosic sugars in *Candida guilliermondii*. Curr Microbiol 31: 239-244.

Tamura K, Dudley J, Nei M, Kumar S, 2007. MEGA4: molecular evolutionary genetics analysis (MEGA) software version 4.0. Molecular Biology and Evolution 24: 1596-1599.

Thompson J D, Higgins D G, Gibson T J, 1994. Clustal-W-improving the sensitivity of progressive multiple sequence alignment through sequence weighting, position-specific gap penalties and weight matrix choice. Nucleic Acids Research 22: 4673-4680.

Tian X L, Cao L X, Tan H M, Zeng Q G, Jia Y Y, Han W Q, Zhou S N, 2004. Study on the communities of endophytic fungi and endophytic Actinomycetes from rice and their antipathogenic activities in vitro. World Journal of Microbiology & Biotechnology 20: 303-309.

Trindade R C, Resende M A, Silva C M, Rosa CA, 2002. Yeasts associated with fresh and frozen pulps of Brazilian tropical fruits. Systematic and Applied Microbiology 25: 294-300.

Vadkertiova R, Slavikova E, 1994. Yeasts from sediments and soil along the Lake Jakubov. Biologia 49: 841-847.

van Aken B, Yoon J M, Schnoor J L, 2004. Biodegradation of nitro-substituted explosives 2,4,6-trinitrotoluene, hexahydro-1,3,5-trinitro-1,3,5-triazine, and octahydro-1,3,5,7-tetranitro-1,3,5-tetrazocine by a phytosymbiotic *Methylobacterium* sp. associated with poplar tissues (*Populus deltoides*×nigra DN34). Applied and Environmental Microbiology 70: 508-517.

Verweij P E, Breuker I M, Rijs A, Meis J, 1999. Comparative study of seven commercial yeast identification systems. Journal of Clinical Pathology 52: 271-273.

Villa-Carvajal M, Coque J J R, Alvarez-Rodriguez M L, Uruburu F, Belloch C, 2004. Polyphasic identification of yeasts isolated from bark of cork oak during the manufacturing process of cork stoppers. FEMS Yeast Research 4: 745-750.

Villegas L B, Amoroso M J, de Figueroa L I C, 2005. Copper tolerant yeasts isolated from polluted area of Argentina. Journal of Basic Microbiology 45: 381-391.

White T J, Bruns T, Lee S, Taylor J, 1990. Amplification and direct sequencing of fungal ribosomal RNA genes for phylogenetics. In: Innis M A, Gelfand D H, Sninsky J J, White T J, (eds), PCR Protocols: A Guide to Methods and Applications, Academic Press, San Diego, pp. 315-322.

Winkelhausen E and Kuzmanova S (1998) Review: Microbial conversion of D-xylose to xylitol. J Fermentation Bioeng 86: 1-14.

Xin G, Glawe D, and Doty S L (2009) Characterization of three endophytic, indole-3-acetic acid-producing yeasts occurring in *Populus* trees. Mycol Res 113: 973-980.

It is understood that the examples and embodiments described herein are for illustrative purposes only and that various modifications or changes in light thereof will be suggested to persons skilled in the art and are to be included within the spirit and purview of this application and scope of the appended claims. All publications, Genbank accession numbers, patents, and patent applications cited herein are hereby incorporated by reference in their entirety for all purposes.

---

What is claimed is:

1. An isolated yeast strain capable of fixing nitrogen, wherein the strain of yeast is heterologous gene from an endophytic yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1 wherein said strain is identified by sequencing an rRNA gene sequence comprising SEQ ID NO:7.

2. The isolated yeast strain of claim 1, wherein the yeast strain is *Rhodotorula graminis* strain WP1, identified by an rRNA gene sequence of SEQ ID NO:7.

3. The isolated yeast strain of claim 2, deposited under deposit number ATCC-PTA-120764.

4. A culture comprising one or more isolated yeast strains of claim 1.

5. A method for fertilizing a crop, the method comprising inoculating the crop with a strain of yeast of claim 1 capable of fixing nitrogen.

6. The method of claim 5, wherein the step of inoculating the crop comprises colonizing the soil the crop is planted in with the yeast.

7. The method of claim 5, wherein the strain of yeast is an endophytic strain of yeast selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1 wherein said strain is identified by an rRNA gene sequence comprising SEQ ID NO: 7.

8. The method of claim 5, wherein the strain of yeast is a recombinant yeast harboring a heterologous gene sequence from an endophytic yeast strain selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1, wherein said endophytic strain is identified by an rRNA gene sequence comprising SEQ ID NO: 7.

9. The method of claim 5, wherein the crop is a food crop.

10. The method of claim 9, wherein the food crop is selected from the group consisting of sugar cane, maize, wheat, rice, potatoes, sugar beets, soybean, oil palm fruit, barley, tomato, coffee, and cocoa.

11. The method of claim 5, wherein the crop is a non-food crop.

12. The method of claim 11, wherein the non-food crop is selected from the group consisting of cottonwood, willow, a woody plant, cotton, a grass, hemp, and bamboo.

13. A method of producing ethanol, xylitol or a mixture thereof, the method comprising fermenting a carbon source with an endophytic strain of yeast selected from the group consisting of *Rhodotorula graminis* strain WP1, *Rhodotorula mucilaginosa* strain PTD2, *Rhodotorula mucilaginosa* strain PTD3, and *Rhodotorula mucilaginosa* strain Ad1 wherein said strain is identified by an rRNA gene sequence comprising SEQ ID NO: 7.

14. The isolated yeast strain of claim 1, wherein the yeast strain comprises the nifH gene.

* * * * *

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: synthetic PCR amplification forward primer NS8
      FP for genomic 18S rRNA

<400> SEQUENCE: 1
tccgcaggtt cacctacgga                                              20

<210> SEQ ID NO 2
```

```
<211> LENGTH: 19
<212> TYPE: DNA
<213> ORGANISM: Artificial Sequence
<220> FEATURE:
<223> OTHER INFORMATION: synthetic PCR amplification reverse primer NS1
      RP for genomic 18S rRNA

<400> SEQUENCE: 2
gtagtcatat gcttgtctc                                              19

<210> SEQ ID NO 3
<211> LENGTH: 24
<212> TYPE: DNA
<213> ORGANISM: Artificial Sequence
<220> FEATURE:
<223> OTHER INFORMATION: synthetic PCR amplification forward primer F63
      FP for genomic sequencing domains 1 and 2 (D1/D2) of
      26S large subunit rRNA region

<400> SEQUENCE: 3
gcatatcaat aagcggagga aaag                                        24

<210> SEQ ID NO 4
<211> LENGTH: 19
<212> TYPE: DNA
<213> ORGANISM: Artificial Sequence
<220> FEATURE:
<223> OTHER INFORMATION: synthetic PCR amplification forward primer LR3
      RP for genomic sequencing domains 1 and 2 (D1/D2) of
      26S large subunit rRNA region

<400> SEQUENCE: 4
ggtccgtgtt tcaagacgg                                              19

<210> SEQ ID NO 5
<211> LENGTH: 19
<212> TYPE: DNA
<213> ORGANISM: Artificial Sequence
<220> FEATURE:
<223> OTHER INFORMATION: synthetic PCR amplification forward primer ITS1
      FP for genomic internal transcribed spacer (ITS) rRNA
      region

<400> SEQUENCE: 5
tccgtaggtg aacctgcgg                                              19

<210> SEQ ID NO 6
<211> LENGTH: 20
<212> TYPE: DNA
<213> ORGANISM: Artificial Sequence
<220> FEATURE:
<223> OTHER INFORMATION: synthetic PCR amplification reverse primer ITS4
      RP for genomic internal transcribed spacer (ITS) rRNA
      region

<400> SEQUENCE: 6
tcctccgctt attgatatgc                                             20

<210> SEQ ID NO 7
<211> LENGTH: 1738
<212> TYPE: DNA
<213> ORGANISM: Rhodotorula graminis
<220> FEATURE:
<223> OTHER INFORMATION: Rhodotorula graminis strain WP1 18S ribosomal
      RNA gene, partial sequence

<400> SEQUENCE: 7
aaagattaag ccatgcatgt ctaagtttaa gcaataaaca gtgaaactgc gaatggctca    60
```

```
ttaaatcagt catagtttat tgatggtac cttactacat ggataactgt ggtaattcta      120
gagctaatac atgctgaaaa atcccgactt ctggaaggga tgtatttatt agatccaaaa      180
ccaatggcct tcgggtctcc ttggtgaatc atgataactg ctcgaatcgc atggccttgc      240
gccggcgatg cttcattcaa atatctgccc tatcaacttt cgatggtagg atagaggcct      300
accatggtga tgacgggtaa cggggaataa ggcttcgatt ccggagagag ggcctgagaa      360
acggccctca ggtctaagga cacgcagcag gcgcgcaaat tatcccctgg caacactttg      420
ccgagatagt gacaataaat aacaatgcag ggctcttacg ggtcttgcaa ttggaatgag      480
tacaatttaa atcccttaac gaggatcaat tggagggcaa gtctggtgcc agcagccgcg      540
gtaattccag ctccaatagc gtatattaaa gttgttgccg ttaaaaagct cgtagtcgaa      600
cttcgggtcc tgtccgccgg tccgccttct tggtgtgtac ttgttggatg ggaccttacc      660
tcctggtgaa cagcgatgtc ctttactggg tgtcgttgca aaccaggacg tttactttga      720
aaaaattaga gtgttcaaag caggcctttg cccgaataca ttagcatgga aataatagaa      780
taggacgcgc gttcccattt tgttggtttc tgagatcgcc gtaatgatta atagggatag      840
ttgggggcat ttgtattccg acgtcagagg tgaaattctt ggattgccgg aagacaaact      900
actgcgaaag catttgccaa ggatgttttc attgatcaag aacgaaggaa ggggatcga      960 aaacgattag ataccgttgt agtctcttct gtaaactatg ccaattgggg atcggcacag     1020 gattttaat gactgtgtcg gcacccgaag agaaatcttt aaatgaggtt cgggggggag     1080
tatggtcgca aggctgaaac ttaaaggaat tgacggaagg gcaccaccag gtgtggagcc     1140
tgcggcttaa tttgactcaa cacggggaaa ctcaccaggt ccagacacaa taaggattga     1200
cagattgata gctctttctt gatcttgtgg ttggtggtgc atggccgttc ttagttggtg     1260
gagtgatttg tctggttaat ccgataacg aacgagacct aacctgcta aatagaccag     1320 ccgactttgg ttagctgctg tcttcttaga gggactatca gcgtttagct gatgaaagtt     1380
tgaggcaata acaggtctgt gatgcccta gatgttctgg gccgcacgcg cgctacactg     1440
acagagccag cgagtctacc acctttgccg gaaggcatgg gtaatcttgt gaaactctgt     1500
cgtgatgggg atagaacatt gcaattattg ttcttcaacg aggaatacct agtaagcgtg     1560
attcatcaga tcgcgttgat tacgtccctg ccctttgtac acaccgcccg tcgctactac     1620
cgattgaatg gcttagtgag gcctccggat tggctattgg gagctcgcga gagcacctga     1680
ctgctgagaa gttgtacgaa cttggtcatt tagaggaagt aaaagtcgta acaaggtt     1738

<210> SEQ ID NO 8
<211> LENGTH: 1281
<212> TYPE: DNA
<213> ORGANISM: Rhodotorula mucilaginosa
<220> FEATURE:
<223> OTHER INFORMATION: Rhodotorula mucilaginosa strain PTD2 18S
      ribosomal RNA gene, partial sequence

<400> SEQUENCE: 8
tgtagtcata tgcttgtctc aaagattaag ccatgcatgt ctaagtttaa gcaataaaca       60
gtgaaactgc gaatggctca ttaaatcagt catagtttat ttgatggtac cttactacat      120
ggataactgt ggtaattcta gagctaatac atgctgaaaa atcccgactt ctggaaggga     180
tgtatttatt agatccaaaa ccaatggcct tcgggtccct atggtgaatc atgataactg      240
ctcgaatcgc atggccttgc gccggcgatg cttcattcaa atatctgccc tatcaacttt     300
cgatggtagg atagaggcct accatggtga tgacgggtaa cggggaataa ggttcgatt     360
```

```
ccggagagag ggcctgagaa acggccctca ggtctaagga cacgcagcag gcgcgcaaat      420
tatcccctgg caacactttg ccgagatagt gacaataaat aacaatgcag ggctcttacg      480
ggtcttgcaa ttggaatgag tacaatttaa atcccttaac gaggatcaat tggagggcaa      540
gtctggtgcc agcagccgcg gtaattccag ctccaatagc gtatattaaa attgttgccg      600
ttaaaaagct cgtagtcgaa cttcgggctc tgtcagccgg tccgccttct tggtgtgtac      660
ttgtttgacg gagccttacc tcctggtgaa cggcgatgtc ctttactggg tgtcgtcgca      720
aaccaggact tttactttga aaaattaga gtgttcaaag caggcctttg cccgaataca      780
ttagcatgga ataataaaat aggacgcgcg ttcccatttt gttggtttct gagatcgccg      840
taatgattaa tagggatagt tgggggcatt tgtattcccg tcgtcagagg tgaaattctt      900
ggattgccgg aagacaaact actgcgaaag catttgccaa ggatgttttc attgatcaag      960
aacgaaggaa gggggatcga aaacgattta gataccgttg tagtctcttc tgtaaactat     1020
gccaattggg gatcggtaca ggattttaa tgactgtatc ggcacccgaa gagaaatctt     1080
taaatgaggt tcgggggga gtatggtcgc aaggctgaaa cttaaaggaa ttgacggaag     1140
ggcaccacca ggtgtggagc ctgcggctta atttgactca acacggggaa actcaccagg     1200
tccagacaca ataaggattg acagattgat agctcttttct tgatcttgtg gttggtggtg     1260
catggccgtt cttagttggt c                                              1281

<210> SEQ ID NO 9
<211> LENGTH: 980
<212> TYPE: DNA
<213> ORGANISM: Rhodotorula mucilaginosa
<220> FEATURE:
<223> OTHER INFORMATION: Rhodotorula mucilaginosa strain PTD3 18S
      ribosomal RNA gene, partial sequence

<400> SEQUENCE: 9
tgtagtcata tgcttgtctc aaagattaag ccatgcatgt ctaagtttaa gcaataaaca       60
gtgaaactgc gaatggctca ttaaatcagt catagtttat ttgatggtac cttactacat      120
ggataactgt ggtaattcta gagctaatac atgctgaaaa atcccgactt ctggaaggga      180
tgtatttatt agatccaaaa ccaatggcct tcgggtccct atggtgaatc atgataactg      240
ctcgaatcgc atggccttgc gccggcgatg cttcattcaa atatctgccc tattaacttt      300
cgatggtagg atagaggcct accatggtga tgacgggtaa cggggaataa gggttcgatt      360
ccggagagag ggcctgagaa acggccctca ggtctaagga cacgcagcag gcgcgcaaat      420
tatcccctgg caacactttg ccgagatagt gacaataaat aacaatgcag ggctcttacg      480
ggtcttgcaa ttggaatgag tacaatttaa atcccttaac gaggatcaat tggagggcaa      540
gtctggtgcc agcagccgcg gtaattccag ctccaatagc gtatattaaa attgttgccg      600
ttaaaaagct cgtagtcgaa cttcgggctc tgtcagccgg tccgccttct tggtgtgtac      660
ttgtttgacg gagccttacc tcctggtgaa cggcgatgtc ctttactggg tgtcgtcgca      720
aaccaggact tttactttga aaaattaga gtgttcaaag caggcctttg cccgaataca      780
ttagcatgga ataataaaat aggacgcgcg ttcccatttt gttggtttct gagatcgccg      840
taatgattaa tagggatagt tgggggcatt tgtattccgt cgtcagaggt gaaattctt      900 ggattgccgg aagacaaact actgcgaaag catttgccaa ggatgttttc attgatcaag      960
aacgaaggaa gggggatcga                                                 980
```

<210> SEQ ID NO 10
<211> LENGTH: 608
<212> TYPE: DNA
<213> ORGANISM: Rhodotorula graminis
<220> FEATURE:
<223> OTHER INFORMATION: Rhodotorula graminis strain WP1 internal
    transcribed spacer 1 (ITS1), partial sequence; 5.8S ribosomal RNA
    gene, complete sequence; internal transcribed spacer 2 (ITS2),
    partial sequence

<400> SEQUENCE: 10

```
tccgtaggtg aacctgcgga cggatcatta gtgaatctag gacgtccaac ttaacttgga      60
gtccgaactc tcactttcta accctgtgca tctgttaaat tggactagta gctcttcgga     120
gtgaaccgcc attcacttat aaacacaaag tctatgaatg tatacaaatt tataacaaaa     180
caaaactttc aacaacggat ctcttggctc tcgcatcgat gaagaacgca gcgaaatgcg     240
atacgtaatg tgaattgcag aattcagtga atcatcgaat ctttgaacgc accttgcgct     300
ccttggtatt ccgaggagca tgcctgtttg agtgtcatga atcttcaac ccacctcttt      360 cttagtgaat ctggtggtgc ttggtttctg agcgctgctc tgcttcggct tagctcgttc     420
gtaatgcatt agcatccgca accgaacttc ggattgactt ggcgtaatag actattcgct     480
gaggattcta gttttactag agccgagttg ggttaaagga agctcctaat cctaaagtct     540 atttttttgat tagatctcaa atcaggtagg actacccgct gaacttaagc atatcaataa    600
gcggagga                                                              608
```

<210> SEQ ID NO 11
<211> LENGTH: 618
<212> TYPE: DNA
<213> ORGANISM: Rhodotorula mucilaginosa
<220> FEATURE:
<223> OTHER INFORMATION: Rhodotorula mucilaginosa strain PTD2 internal
    transcribed spacer 1 (ITS1), partial sequence; 5.8S ribosomal RNA
    gene, complete sequence; internal transcribed spacer 2 (ITS2),
    partial sequence
<220> FEATURE:
<221> NAME/KEY: modified_base
<222> LOCATION: (20)...(21)
<223> OTHER INFORMATION: n = g, a, c or t

<400> SEQUENCE: 11

```
tccgtaggtg aacctgcggn nggatcatta gtgaatatag gacgtccaac ttaacttgga      60
gtccgaactc tcactttcta accctgtgca tttgttggg atagtaactc tcgcaagagg      120
gcgaactcct attcacttat aaacacaaag tctatgaatg tattaaattt tataacaaaa     180
taaaactttc aacaacggat ctcttggctc tcgcatcgat gaagaacgca gcgaaatgcg     240
ataagtaatg tgaattgcag aattcagtga atcatcgaat ctttgaacgc accttgcgct     300
ccatggtatt ccgtggagca tgcctgtttg agtgtcatga atacttcaac cctcctcttt     360
cttaatgatt gaagaggtgt ttggtttctg agcgctgctg gcctttaggg tctagctcgt     420
tcgtaatgca ttagcatccg caatcgaact tcggattgac ttggcgtaat agactattcg     480
ctgaggaatt ctagtcttcg gactagagcc gggttgggtt aaaggaagct tctaatcaga     540
atgtctacat tttaagatta gatctcaaat caggtaggac tacccgctga acttaagcat     600
atcaaataaa gcggagga                                                   618
```

<210> SEQ ID NO 12
<211> LENGTH: 617
<212> TYPE: DNA
<213> ORGANISM: Rhodotorula mucilaginosa
<220> FEATURE:

<223> OTHER INFORMATION: Rhodotorula mucilaginosa strain PTD3 internal
transcribed spacer 1 (ITS1), partial sequence; 5.8S ribosomal RNA
gene, complete sequence; internal transcribed spacer 2 (ITS2),
partial sequence

<400> SEQUENCE: 12

```
tccgtaggtg aacctgcgga cggatcatta gtgaatatag gacgtccaac ttaacttgga    60
gtccgaactc tcactttcta accctgtgca tttgtttggg atagtaactc tcgcaagagg   120
gcgaactcct attcacttat aaacacaaag tctatgaatg tattaaattt tataacaaaa   180
taaaactttc aacaacggat ctcttggctc tcgcatcgat gaagaacgca gcgaaatgcg   240
ataagtaatg tgaattgcag aattcagtga atcatcgaat ctttgaacgc accttgcgct   300
ccatggtatt ccgtggagca tgcctgtttg agtgtcatga atacttcaac cctcctcttt   360
cttaatgatt gaagaggtgt ttggtttctg agcgctgctg gcctttaggg tctagctcgt   420
tcgtaatgca ttagcatccg caatcgaact tcggattgac ttggcgtaat agactattcg   480
ctgaggaatt ctagtcttcg gactagagcc gggttgggtt aaaggaagct tctaatcaga   540
atgtctacat tttaagatta gatctcaaat caggtaggac tacccgctga acttaagcat   600
atcaataaag cggagga                                                  617
```

<210> SEQ ID NO 13
<211> LENGTH: 617
<212> TYPE: DNA
<213> ORGANISM: Rhodotorula graminis
<220> FEATURE:
<223> OTHER INFORMATION: Rhodotorula graminis strain WP1 genomic
sequencing domains 1 and 2 (D1/D2) of 26S large subunit ribosomal
RNA gene, partial sequence

<400> SEQUENCE: 13

```
gcatatcaat aagcggagga aaagaaacta acaaggattc ccctagtagc ggcgagcgaa    60
gcgggaagag ctcaaattta taatctggca ccttcggtgt ccgagttgta atctctagaa   120
gtgttttccg cgttggaccg cacacaagtc tgttggaata cagcggcata gtggtgaaac   180
ccccgtatat ggtgcggacg cccagcgctt tgtgatacac tttcaatgag tcgagttgtt   240
tgggaatgca gctcaaattg ggtggtaaat tccatctaaa gctaaatatt ggcgagagac   300
cgatagcgaa caagtaccgt gagggaaaga tgaaaagcac tttggaaaga gagttaacag   360
tacgtgaaat tgttggaagg gaaacgcttg aagtcagact tgcttgccgg agcttgcttc   420 ggttttgcagg ccagcatcag ttttccgggg tggataatga cggtttgaag gtagcagtct   480
cggctgtgtt atagctttcc gttggataca tcctggggga ctgaggaacg cagcgtgctt   540
tttgcgaaag actcgtcttt ttcacgctta ggatgctggt ggaatggctt taaacgaccc   600
gtcttgaaac acggacc                                                  617
```

<210> SEQ ID NO 14
<211> LENGTH: 614
<212> TYPE: DNA
<213> ORGANISM: Rhodotorula mucilaginosa
<220> FEATURE:
<223> OTHER INFORMATION: Rhodotorula mucilaginosa strain PTD2 genomic
sequencing domains 1 and 2 (D1/D2) of 26S large subunit ribosomal
RNA gene, partial sequence

<400> SEQUENCE: 14

```
gcatatcaat aagcggagga aaagaaacta acaaggattc ccctagtagc ggcgagcgaa    60
gcgggaagag ctcaaattta taatctggca ccttcggtgt ccgagttgta atctctagaa   120
```

```
atgttttccg cgttggaccg cacacaagtc tgttggaata cagcggcata gtggtgagac      180
ccccgtatat ggtgcggacg cccagcgctt tgtgatacat tttcgaagag tcgagttgtt      240
tgggaatgca gctcaaattg ggtggtaaat tccatctaaa gctaaatatt ggcgagagac      300
cgatagcgaa caagtaccgt gagggaaaga tgaaaagcac tttggaaaga gagttaacag      360
tacgtgaaat tgttggaagg gaaacgcttg aagtcagact tgcttgccga gcaatcggtt      420
tgcaggccag catcagtttt ccgggatgga taatggtaga gagaaggtag cagtttcggc      480
tgtgttatag ctctctgctg gatacatctt ggggggactga ggaacgcagt gtgcctttg       540 gcggggtttt cgacctcttc acacttagga tgctggtgga atggctttaa acgacccgtc      600
ttgaaacacg gacc                                                       614
```

<210> SEQ ID NO 15
<211> LENGTH: 614
<212> TYPE: DNA
<213> ORGANISM: Rhodotorula mucilaginosa
<220> FEATURE:
<223> OTHER INFORMATION: Rhodotorula mucilaginosa strain PTD3 genomic sequencing domains 1 and 2 (D1/D2) of 26S large subunit ribosomal RNA gene, partial sequence

<400> SEQUENCE: 15

```
gcatatcaat aagcggagga aaagaaacta acaaggattc ccctagtagc ggcgagcgaa      60 gcggaagag ctcaaattta taatctggca ccttcggtgt ccgagttgta atctctagaa       120
atgttttccg cgttggaccg cacacaagtc tgttggaata cagcggcata gtggtgagac      180
ccccgtatat ggtgcggacg cccagcgctt tgtgatacat tttcgaagag tcgagttgtt      240
tgggaatgca gctcaaattg ggtggtaaat tccatctaaa gctaaatatt ggcgagagac      300
cgatagcgaa caagtaccgt gagggaaaga tgaaaagcac tttggaaaga gagttaacag      360
tacgtgaaat tgttggaagg gaaacgcttg aagtcagact tgcttgccga gcaatcggtt      420
tgcaggccag catcagtttt ccgggatgga taatggtaga gagaaggtag cagtttcggc      480
tgtgttatag ctctctgctg gatacatctt ggggggactga ggaacgcagt gtgcctttg       540 gcggggtttt cgacctcttc acacttagga tgctggtgga atggctttaa acgacccgtc      600
ttgaaacacg gacc                                                       614
```

<210> SEQ ID NO 16
<211> LENGTH: 1079
<212> TYPE: DNA
<213> ORGANISM: Artificial Sequence
<220> FEATURE:
<223> OTHER INFORMATION: synthetic Rhodotorula mucilaginosa strain Ad1 18S rRNA insert in pGEM expression vector using primers T7U and Ad1FP18S
<220> FEATURE:
<221> NAME/KEY: modified_base
<222> LOCATION: (1)...(1079)
<223> OTHER INFORMATION: n = g, a, c or t

<400> SEQUENCE: 16

```
cnngcgatnc agctccggcc gccatggcgg ccgcgggaaa ttcgattccg tcaggttcac      60
ctacggaaac cttgattacg acttttactt cctctaaatg accaagttcg tacaacttct      120
cggcagtcgg gtgctctcgc gagctcccaa tagccaatcc ggaggcctca ctaagccatt      180
caatcggtag tagcgacggg cggtgtgtac aaagggcagg gacgtaatca acgcgatctg      240
atgaatcacg cttactaggt attcctcgtt gaagaacaat aattgcaatg ttctatcccc      300
atcacgacag agtttcacaa gattacccat gccttccggc aaaggtggta gactcgctgg      360
```

```
ctctgtcagt gtagcgcgcg tgcggcccag aacatctaag ggcatcacag acctgttatt    420
gcctcaaact tccatcagct aaacgctgat agtccctcta agaagacagc agctagccaa    480
agccggctgg tctatttagc aggttaaggt ctcgttcgtt atcggaatta accagacaaa    540
tcactccacc aactaagaac ggccatgcac caccaaccac aagatcaaga aagagctatc    600
aatctgtcaa tccttattgt gtctggacct ggtgagtttc cccgtgttga gtcaaattaa    660
gccgcaggct ccacacctgg tggtgccctt ccgtcaattc ctttaagttt cagccttgcg    720
accatactcc cccccgaacc tcatttaaag atttctcttc gggtgccgat acagtcatta    780
aaaatcctgt accgatcccc aattggcata gtttacagaa gagactacaa cggtatctaa    840
tcgttttcga tccccctttcc ttcgttcttg atcaatgaaa acatccttgg caanggcttt    900
tcgcagtagt ttgtcttccg gcaatccaag aatttcacct ctgacgacgg aatacaaatg    960
cccccaacta tccctattaa tcattacggg ngatctcana aaccaacaaa atgggaacgc   1020
gngnccnaat ttnattattc cntggctaat ggnttcnggg caaaggcntn cttngancc    1079
```

<210> SEQ ID NO 17
<211> LENGTH: 1078
<212> TYPE: DNA
<213> ORGANISM: Artificial Sequence
<220> FEATURE:
<223> OTHER INFORMATION: synthetic Rhodotorula mucilaginosa strain Ad1 18S rRNA insert in pGEM expression vector using primers SP6 and Ad1RP18S
<220> FEATURE:
<221> NAME/KEY: modified_base
<222> LOCATION: (1)...(1078)
<223> OTHER INFORMATION: n = g, a, c or t

<400> SEQUENCE: 17

```
tctcacgcgt gggagctctc ccatatggtc gacctgcagg cggccgcgaa ttcactagtg     60
attgtagtca tatgcttgtc tcaaagatta agccatgcat gtctaagttt aagcaataaa    120
cagtgaaact gcgaatggct cattaaatca gtcatagttt atttgatggt accttactac    180
atggataact gtggtaattc tagagctaat acatgctgaa aaatcccgac ttctggaagg    240
gatgtattta ttagatccaa aaccaatggc cttcgggtcc ctatggtgaa tcatgataac    300
tgctcgaatc gcatggcctt gcgccggcga tgcttcattc aaatatctgc cctatcaact    360
ttcgatggta ggatagaggc ctaccatggt gatgacgggt aacggggaat aagggttcga    420
ttccggagag agggcctgag aaacggccct caggtctaag gacacgcagc aggcgcgcaa    480
attatcccct ggcaacactt tgccgagata gtgacaataa ataacaatgc agggctctta    540
cgggtcttgc aattggaatg agtacaattt aaatcccttta acgaggatca attggagggc    600
aagtctggtg ccagcagccg cggtaattcc agctccaata gcgtatatta aaattgttgc    660
cgttaaaaag ctcgtagtcg aacttcgggc tctgtcagcc ggtccgcctt cttggtgtgt    720
acttgtttga cggagcctta cctcctggtg aacggcgatg tcctttactg ggtgtcgtcg    780
caaaccagga cttttacttt gaaaaaatta gagtgttcaa gcaggccttt gccccgaata    840
cattagcatg gaataataaa ataggacgcg cgttcccntt tttgntggnt tctgaaatcg    900
ccgtaatgat taatanggat agttgggggg catttngtat tccgtcgtcn gaagtgaaat    960
tcttggattg ccggaaaaca aactactgcg aaagcatttg ccaaggatgt tttccttgat   1020
caagaacgaa ggaaggggga tcgaaaacga tnanataccg ttgtagtcnc ttctgtaa     1078
```

<210> SEQ ID NO 18

<211> LENGTH: 1890
<212> TYPE: DNA
<213> ORGANISM: Artificial Sequence
<220> FEATURE:
<223> OTHER INFORMATION: synthetic Rhodotorula mucilaginosa strain Ad1 18S ribosomal RNA isolated from Arundo donax giant reed
<220> FEATURE:
<221> NAME/KEY: modified_base
<222> LOCATION: (1)...(1890)
<223> OTHER INFORMATION: n = g, a, c or t

<400> SEQUENCE: 18

```
ngcgatncag ctccggccgc catggcggcc gcgggaaatt cgattccgtc aggttcacct      60
acggaaacct tgattacgac ttttacttcc tctaaatgac caagttcgta caacttctcg     120
gcagtcgggt gctctcgcga gctcccaata gccaatccgg aggcctcact aagccattca     180
atcggtagta gcgacgggcg gtgtgtacaa agggcaggga cgtaatcaac gcgatctgat     240
gaatcacgct tactaggtat tcctcgttga agaacaataa ttgcaatgtt ctatccccat     300
cacgacagag tttcacaaga ttacccatgc cttccggcaa aggtggtaga ctcgctggct     360
ctgtcagtgt agcgcgcgtg cggcccagaa catctaaggg catcacagac ctgttattgc     420
ctcaaacttc catcagctaa acgctgatag tccctctaag aagacagcag ctagccaaag     480
ccggctggtc tatttagcag gttaaggtct cgttcgttat cggaattaac cagacaaatc     540
actccaccaa ctaagaacgg ccatgcacca ccaaccacaa gatcaagaaa gagctatcaa     600
tctgtcaatc cttattgtgt ctggacctgg tgagtttccc cgtgttgagt caaattaagc     660
cgcaggctcc acacctggtg gtgcccttcc gtcaattcct ttaagtttca gccttgcgac     720
catactcccc cccgaacctc atttaaagat ttctcttcgg gtgccgatac agtcattaaa     780
aatcctgtac cgatccccaa ttggcatagt ttacagaaga gactacaacg gtatctaatc     840
gttttcgatc ccccttcctt cgttcttgat caakgaaaac atccttggca aakgcttttc     900
gcagtagttt gtyttccggc aatccaagaa tttcacytct gacgacggaa tacnaaatgc     960
cccccaacta tccctattaa tcattacggs ngatytcaga aaccaacaaa awngggaacg    1020
cgcgtcctat tttattattc catgctaatg tattcggggc aaaggcctgc ttgaacactc    1080
taattttttc aaagtaaaag tcctggtttg cgacgacacc cagtaaagga catcgccgtt    1140
caccaggagg taaggctccg tcaaacaagt acacaccaag aaggcggacc ggctgacaga    1200
gcccgaagtt cgactacgag cttttttaacg gcaacaattt taatatacgc tattggagct    1260
ggaattaccg cggctgctgg caccagactt gccctccaat tgatcctcgt taagggattt    1320
aaattgtact cattccaatt gcaagacccg taagagccct gcattgttat ttattgtcac    1380
tatctcggca aagtgttgcc aggggataat ttgcgcgcct gctgcgtgtc cttagacctg    1440
agggccgttt ctcaggccct ctctccggaa tcgaacccct attccccgtt acccgtcatc    1500
accatggtag gcctctatcc taccatcgaa agttgatagg gcagatattt gaatgaagca    1560
tcgccggcgc aaggccatgc gattcgagca gttatcatga ttcaccatag ggacccgaag    1620
gccattggtt ttggatctaa taaatacatc ccttccagaa gtcgggattt ttcagcatgt    1680
attagctcta gaattaccac agttatccat gtagtaaggt accatcaaat aaactatgac    1740
tgatttaatg agccattcgc agtttcactg tttattgctt aaacttagac atgcatggct    1800
taatctttga dacaagcata tgactacaat cactagtgaa ttcgcggccg cctgcaggtc    1860
gaccatatgg gagagctccc acgcgtgaga                                    1890
```

<210> SEQ ID NO 19

```
<211> LENGTH: 18
<212> TYPE: DNA
<213> ORGANISM: Artificial Sequence
<220> FEATURE:
<223> OTHER INFORMATION: synthetic RT-PCR amplification and cloning
      primer WP1-XR-F

<400> SEQUENCE: 19
atggtccaga ctgtcccc                                                18

<210> SEQ ID NO 20
<211> LENGTH: 22
<212> TYPE: DNA
<213> ORGANISM: Artificial Sequence
<220> FEATURE:
<223> OTHER INFORMATION: synthetic RT-PCR amplification and cloning
      primer WP1-XR-R

<400> SEQUENCE: 20
tcagtgacgg tcgatagaga tc                                           22

<210> SEQ ID NO 21
<211> LENGTH: 20
<212> TYPE: DNA
<213> ORGANISM: Artificial Sequence
<220> FEATURE:
<223> OTHER INFORMATION: synthetic RT-PCR amplification and cloning
      primer WP1-XDH-F

<400> SEQUENCE: 21
atgagcgctc ccagtctcgc                                              20

<210> SEQ ID NO 22
<211> LENGTH: 21
<212> TYPE: DNA
<213> ORGANISM: Artificial Sequence
<220> FEATURE:
<223> OTHER INFORMATION: synthetic RT-PCR amplification and cloning
      primer WP1-XDH-R

<400> SEQUENCE: 22
tcactcgagc ttctcgtcga c                                            21

<210> SEQ ID NO 23
<211> LENGTH: 20
<212> TYPE: DNA
<213> ORGANISM: Artificial Sequence
<220> FEATURE:
<223> OTHER INFORMATION: synthetic RT-PCR amplification and cloning
      degenerate primer PTD3-D-XR-F

<400> SEQUENCE: 23
gcyatcaagk cgggytaccg                                              20

<210> SEQ ID NO 24
<211> LENGTH: 21
<212> TYPE: DNA
<213> ORGANISM: Artificial Sequence
<220> FEATURE:
<223> OTHER INFORMATION: synthetic RT-PCR amplification and cloning
      degenerate primer PTD3-D-XR-R

<400> SEQUENCE: 24
gtggwagbtg ttccasagct t                                            21

<210> SEQ ID NO 25
<211> LENGTH: 20
```

<212> TYPE: DNA
<213> ORGANISM: Artificial Sequence
<220> FEATURE:
<223> OTHER INFORMATION: synthetic RT-PCR amplification and cloning
      degenerate primer PTD3-D-XDH-F
<220> FEATURE:
<221> NAME/KEY: modified_base
<222> LOCATION: (15)...(15)
<223> OTHER INFORMATION: n = g, a, c or t

<400> SEQUENCE: 25
ccmatggtcy tsggncacga                                                   20

<210> SEQ ID NO 26
<211> LENGTH: 23
<212> TYPE: DNA
<213> ORGANISM: Artificial Sequence
<220> FEATURE:
<223> OTHER INFORMATION: synthetic RT-PCR amplification and cloning
      degenerate primer PTD3-D-XDH-R

<400> SEQUENCE: 26
ccgacvggvc cdgcdccaaa gac                                               23

<210> SEQ ID NO 27
<211> LENGTH: 20
<212> TYPE: DNA
<213> ORGANISM: Artificial Sequence
<220> FEATURE:
<223> OTHER INFORMATION: synthetic 5' rapid amplification of cDNA ends
      (5' RACE) primer PTD3-XR-GSP1

<400> SEQUENCE: 27
gccagtggat gaggtagagg                                                   20

<210> SEQ ID NO 28
<211> LENGTH: 20
<212> TYPE: DNA
<213> ORGANISM: Artificial Sequence
<220> FEATURE:
<223> OTHER INFORMATION: synthetic 5' rapid amplification of cDNA ends
      (5' RACE) primer PTD3-XR-GSP2

<400> SEQUENCE: 28
gtgatgaaga tgtccttgcg                                                   20

<210> SEQ ID NO 29
<211> LENGTH: 20
<212> TYPE: DNA
<213> ORGANISM: Artificial Sequence
<220> FEATURE:
<223> OTHER INFORMATION: synthetic 3' rapid amplification of cDNA ends
      (3' RACE) primer PTD3-XR-GSP3

<400> SEQUENCE: 29
aggtctacgg caaccagaag                                                   20

<210> SEQ ID NO 30
<211> LENGTH: 21
<212> TYPE: DNA
<213> ORGANISM: Artificial Sequence
<220> FEATURE:
<223> OTHER INFORMATION: synthetic 3' rapid amplification of cDNA ends
      (3' RACE) primer PTD3-XR-GSP4

<400> SEQUENCE: 30
atcacctcga agctctggaa c                                                 21

<210> SEQ ID NO 31
<211> LENGTH: 21
<212> TYPE: DNA
<213> ORGANISM: Artificial Sequence
<220> FEATURE:
<223> OTHER INFORMATION: synthetic 5' rapid amplification of cDNA ends
      (5' RACE) primer PTD3-XDH-GSP1

<400> SEQUENCE: 31
gatgagcgat ttgaggttga c                                              21

<210> SEQ ID NO 32
<211> LENGTH: 19
<212> TYPE: DNA
<213> ORGANISM: Artificial Sequence
<220> FEATURE:
<223> OTHER INFORMATION: synthetic 5' rapid amplification of cDNA ends
      (5' RACE) primer PTD3-XDH-GSP2

<400> SEQUENCE: 32
ccttggcaac tgcgtggac                                                 19

<210> SEQ ID NO 33
<211> LENGTH: 21
<212> TYPE: DNA
<213> ORGANISM: Artificial Sequence
<220> FEATURE:
<223> OTHER INFORMATION: synthetic 3' rapid amplification of cDNA ends
      (3' RACE) primer PTD3-XR-GSP3

<400> SEQUENCE: 33
gcaaaggtgg tcattacgaa c                                              21

<210> SEQ ID NO 34
<211> LENGTH: 20
<212> TYPE: DNA
<213> ORGANISM: Artificial Sequence
<220> FEATURE:
<223> OTHER INFORMATION: synthetic 3' rapid amplification of cDNA ends
      (3' RACE) primer PTD3-XR-GSP4

<400> SEQUENCE: 34
ctccttgagc ccatgtcggt                                                20

<210> SEQ ID NO 35
<211> LENGTH: 21
<212> TYPE: DNA
<213> ORGANISM: Artificial Sequence
<220> FEATURE:
<223> OTHER INFORMATION: synthetic RT-PCR amplification primer #XR-F

<400> SEQUENCE: 35
atcacctcga agctctggaa c                                              21

<210> SEQ ID NO 36
<211> LENGTH: 20
<212> TYPE: DNA
<213> ORGANISM: Artificial Sequence
<220> FEATURE:
<223> OTHER INFORMATION: synthetic RT-PCR amplification primer #XR-R

<400> SEQUENCE: 36
gccagtggat gaggtagagg                                                20

<210> SEQ ID NO 37
<211> LENGTH: 20

```
<212> TYPE: DNA
<213> ORGANISM: Artificial Sequence
<220> FEATURE:
<223> OTHER INFORMATION: synthetic RT-PCR amplification primer #XDH-F

<400> SEQUENCE: 37
ctccttgagc ccatgtcggt                                              20

<210> SEQ ID NO 38
<211> LENGTH: 21
<212> TYPE: DNA
<213> ORGANISM: Artificial Sequence
<220> FEATURE:
<223> OTHER INFORMATION: synthetic RT-PCR amplification primer #XDH-R

<400> SEQUENCE: 38
gatgagcgat ttgaggttga c                                            21

<210> SEQ ID NO 39
<211> LENGTH: 21
<212> TYPE: DNA
<213> ORGANISM: Artificial Sequence
<220> FEATURE:
<223> OTHER INFORMATION: synthetic cloning primer 515F(18S rRNA)

<400> SEQUENCE: 39
gtgccaaggc agccgcggta a                                            21

<210> SEQ ID NO 40
<211> LENGTH: 16
<212> TYPE: DNA
<213> ORGANISM: Artificial Sequence
<220> FEATURE:
<223> OTHER INFORMATION: synthetic cloning primer 1209R(18S rRNA)

<400> SEQUENCE: 40
gggcatcaca gacctg                                                  16

<210> SEQ ID NO 41
<211> LENGTH: 966
<212> TYPE: DNA
<213> ORGANISM: Rhodotorula graminis
<220> FEATURE:
<223> OTHER INFORMATION: Rhodotorula graminis strain WP1 xylose
      reductase (XR) gene open reading frame (ORF)

<400> SEQUENCE: 41
atgcctcacg tcacccagcc acccgcgtcc ttccagctca acacgggcgc gtcgatcccg     60
tctgtcggcc tcggcacgtg gcaggccaag ccgggcgagg tcgcgagcgc cgtcgagcac    120
gccctcaagt cgggctaccg tcacctcgac tgcgcgctca tctaccagaa cgagcaagaa    180
gtcggcgctg gcatcaaggc gtcgagcgtg ccgaggtccg agatctttat cacgtcgaag    240
ctgtggaaca cgtaccacga caaggtcgag caatgcctcg acgagtcgct cgcatcgctc    300
ggcgtcgact acctcgacct gtacctcatc cactggcccg tgcggctcgt cccgaacgag    360
tcgtcggcgc tcctccccgt caacccggac ggctctcgcg ccgtcgaccg cgactgggac    420
atgagcaaga cgtgggcgag catggaggcc ctgctcaaga cgggcaaggt caaggcggtt    480
ggcgtctcga actggagcgt cgcgtacctc gagaagctcg agaagacgtg gacggtcgtc    540
cctgccgtca accaggtcga gctccacccg ttcaacccgc agcacaagct caaggcctgg    600
tgcgacaagc gcggcatcct cctcgaggcc tactgccctc tcggctcgac caactcgccc    660
ctcctgtccg acccggagct gaacgccatc gccgacaagc acggcgtctc gcccgcgacc    720
```

```
gtcctcatct cgtaccagcc tcaacgcggc tgcgtcgtgc tccccaagtc ggtgagcgca    780
gcacgcatcg aggccaacct tcacctcatc acgctcgacg ccgacgacat ggacacgctc    840
gacggcatgg ccgccaaggg caagcagcag cgcgtcaaca cgccgctctt tgggtgggac    900
ctcgggttcg aggattggta tcctgcgcag gccaaggcga tgctggccaa tggcgggtac    960
ctttag                                                                966
```

```
<210> SEQ ID NO 42
<211> LENGTH: 321
<212> TYPE: PRT
<213> ORGANISM: Rhodotorula graminis
<220> FEATURE:
<223> OTHER INFORMATION: Rhodotorula graminis strain WP1 xylose
      reductase (XR) gene open reading frame (ORF) translation

<400> SEQUENCE: 42
```

| | | | | | | | | | | | | | | | |
|---|---|---|---|---|---|---|---|---|---|---|---|---|---|---|---|
| Met | Pro | His | Val | Thr | Gln | Pro | Pro | Ala | Ser | Phe | Gln | Leu | Asn | Thr | Gly |
| 1 | | | | 5 | | | | | 10 | | | | | 15 | |
| Ala | Ser | Ile | Pro | Ser | Val | Gly | Leu | Gly | Thr | Trp | Gln | Ala | Lys | Pro | Gly |
| | | | 20 | | | | | 25 | | | | | 30 | | |
| Glu | Val | Ala | Ser | Ala | Val | Glu | His | Ala | Leu | Lys | Ser | Gly | Tyr | Arg | His |
| | | 35 | | | | | 40 | | | | | 45 | | | |
| Leu | Asp | Cys | Ala | Leu | Ile | Tyr | Gln | Asn | Glu | Gln | Glu | Val | Gly | Ala | Gly |
| | 50 | | | | | 55 | | | | | 60 | | | | |
| Ile | Lys | Ala | Ser | Ser | Val | Pro | Arg | Ser | Glu | Ile | Phe | Ile | Thr | Ser | Lys |
| 65 | | | | | 70 | | | | | 75 | | | | | 80 |
| Leu | Trp | Asn | Thr | Tyr | His | Asp | Lys | Val | Glu | Gln | Cys | Leu | Asp | Glu | Ser |
| | | | | 85 | | | | | 90 | | | | | 95 | |
| Leu | Ala | Ser | Leu | Gly | Val | Asp | Tyr | Leu | Asp | Leu | Tyr | Leu | Ile | His | Trp |
| | | | 100 | | | | | 105 | | | | | 110 | | |
| Pro | Val | Arg | Leu | Val | Pro | Asn | Glu | Ser | Ser | Ala | Leu | Leu | Pro | Val | Asn |
| | | 115 | | | | | 120 | | | | | 125 | | | |
| Pro | Asp | Gly | Ser | Arg | Ala | Val | Asp | Arg | Asp | Trp | Asp | Met | Ser | Lys | Thr |
| | 130 | | | | | 135 | | | | | 140 | | | | |
| Trp | Ala | Ser | Met | Glu | Ala | Leu | Leu | Lys | Thr | Gly | Lys | Val | Lys | Ala | Val |
| 145 | | | | | 150 | | | | | 155 | | | | | 160 |
| Gly | Val | Ser | Asn | Trp | Ser | Val | Ala | Tyr | Leu | Glu | Lys | Leu | Glu | Lys | Thr |
| | | | | 165 | | | | | 170 | | | | | 175 | |
| Trp | Thr | Val | Val | Pro | Ala | Val | Asn | Gln | Val | Glu | Leu | His | Pro | Phe | Asn |
| | | | 180 | | | | | 185 | | | | | 190 | | |
| Pro | Gln | His | Lys | Leu | Lys | Ala | Trp | Cys | Asp | Lys | Arg | Gly | Ile | Leu | Leu |
| | | 195 | | | | | 200 | | | | | 205 | | | |
| Glu | Ala | Tyr | Cys | Pro | Leu | Gly | Ser | Thr | Asn | Ser | Pro | Leu | Leu | Ser | Asp |
| | 210 | | | | | 215 | | | | | 220 | | | | |
| Pro | Glu | Leu | Asn | Ala | Ile | Ala | Asp | Lys | His | Gly | Val | Ser | Pro | Ala | Thr |
| 225 | | | | | 230 | | | | | 235 | | | | | 240 |
| Val | Leu | Ile | Ser | Tyr | Gln | Pro | Gln | Arg | Gly | Cys | Val | Val | Leu | Pro | Lys |
| | | | | 245 | | | | | 250 | | | | | 255 | |
| Ser | Val | Ser | Ala | Ala | Arg | Ile | Glu | Ala | Asn | Leu | His | Leu | Ile | Thr | Leu |
| | | | 260 | | | | | 265 | | | | | 270 | | |
| Asp | Ala | Asp | Asp | Met | Asp | Thr | Leu | Asp | Gly | Met | Ala | Ala | Lys | Gly | Lys |
| | | 275 | | | | | 280 | | | | | 285 | | | |
| Gln | Gln | Arg | Val | Asn | Thr | Pro | Leu | Phe | Gly | Trp | Asp | Leu | Gly | Phe | Glu |
| | 290 | | | | | 295 | | | | | 300 | | | | |

Asp Trp Tyr Pro Ala Gln Ala Lys Ala Met Leu Ala Asn Gly Gly Tyr
305                 310                 315                 320

Leu

<210> SEQ ID NO 43
<211> LENGTH: 1191
<212> TYPE: DNA
<213> ORGANISM: Rhodotorula graminis
<220> FEATURE:
<223> OTHER INFORMATION: Rhodotorula graminis strain WP1 xylose
      dehydrogenase (XDH) gene open reading frame (ORF)

<400> SEQUENCE: 43
atgagcgctc ccagtctcgc tgctcccgtc cacaacgagg acacggcgct ccccaccggc      60
gcccacaaca tctcctgcgt cttgcacggc atcgacgacg tccgcttcga ggaccggcct     120
gtgccgaccg agtgcggcga ggacgacgcg atcgtttcgc cagccaaaat ctcggtttgc     180
ggctccgaca cgcactatat caagcatggc cgcatcggcg actttatcgt cgagaagccc     240
atggtcctcg ccacgagac ggcggccgtc gtcgtccagg ttggcagccg cgtcaccaac     300
atcaaggccg cgaccgcgt cgcgctcgaa ccaggtcgct cctgcagggt ctgctccgac     360
tgcaaggccg gcttctacaa ccgctgcgcc agcatggcct ttgcagctac cccgccttat     420
gatggcaccc tcgccgccta ctacacgctc cctgccgacc tgtgctaccc cttgccgagc     480
aacatgtctc tcgaggaagg cgccctgctc gagcccatgt cggtcggtgt ccacgccgtt     540
cacaaggtgg cccaaatgaa agcgccgcc aacgtggttg tctttggcgc aggcccggtc     600
ggcctcctca gtgcgctgt cgccaagggt ctcggagcgc gcaaggtcat cgctgtcgac     660
atccaggagg ctcgtctcgc gttcgccaag gagcagggcc tcgtcgacga ctactacctt     720
ccgcccaagc cgcaggacgg cgaggccaag gccgactacc gcgccgcaa cgccaaggag     780 ctttgcgaac gctttgggtt cgaggagcgc gggcctcgcg gcgtcgacct cgtcctcgac     840
tgctcgggag ccgaggtgtg catccagacc ggcgtcttcg tcctcaagca cggcggcacg     900
ctcgtccagg tcggcatggg caagcccgac atcacgctcg acatgcacac gatcatcacg     960
cgcgagttga cgctcaaggg ctcgttccgc tacggtccgg cgtttacga gctcgcgatg    1020 gacctcgtcg ctcgcggcgc cgtcaacctc aagtcgctca tctcgcacag gtacgcgttc    1080
cgcgacgcac tcaaggcgtt cgaggcgaac cacacgggca tcgcggagga tggaaggccg    1140
ttgatcaagg cggtcatcga cgggcctcgc gtcgacgaga agctcgagtg a             1191

<210> SEQ ID NO 44
<211> LENGTH: 396
<212> TYPE: PRT
<213> ORGANISM: Rhodotorula graminis
<220> FEATURE:
<223> OTHER INFORMATION: Rhodotorula graminis strain WP1 xylose
      dehydrogenase (XDH) gene open reading frame (ORF) translation

<400> SEQUENCE: 44

Met Ser Ala Pro Ser Leu Ala Ala Pro Val His Asn Glu Asp Thr Ala
  1               5                  10                  15

Leu Pro Thr Gly Ala His Asn Ile Ser Cys Val Leu His Gly Ile Asp
                 20                  25                  30

Asp Val Arg Phe Glu Asp Arg Pro Val Pro Thr Glu Cys Gly Glu Asp
             35                  40                  45

Asp Ala Ile Val Ser Pro Ala Lys Ile Ser Val Cys Gly Ser Asp Thr
         50                  55                  60

```
His Tyr Ile Lys His Gly Arg Ile Gly Asp Phe Ile Val Glu Lys Pro
 65                  70                  75                  80

Met Val Leu Gly His Glu Thr Ala Ala Val Val Gln Val Gly Ser
                 85                  90                  95

Arg Val Thr Asn Ile Lys Ala Gly Asp Arg Val Ala Leu Glu Pro Gly
            100                 105                 110

Arg Ser Cys Arg Val Cys Ser Asp Cys Lys Ala Gly Phe Tyr Asn Arg
        115                 120                 125

Cys Ala Ser Met Ala Phe Ala Thr Pro Tyr Asp Gly Thr Leu
130                 135                 140

Ala Ala Tyr Tyr Thr Leu Pro Ala Asp Leu Cys Tyr Pro Leu Pro Ser
145                 150                 155                 160

Asn Met Ser Leu Glu Glu Gly Ala Leu Leu Glu Pro Met Ser Val Gly
                165                 170                 175

Val His Ala Val His Lys Val Ala Gln Met Lys Ser Ala Ala Asn Val
            180                 185                 190

Val Val Phe Gly Ala Gly Pro Val Gly Leu Leu Thr Cys Ala Val Ala
        195                 200                 205

Lys Gly Leu Gly Ala Arg Lys Val Ile Ala Val Asp Ile Gln Glu Ala
210                 215                 220

Arg Leu Ala Phe Ala Lys Glu Gln Gly Leu Val Asp Asp Tyr Tyr Leu
225                 230                 235                 240

Pro Pro Lys Pro Gln Asp Gly Glu Ala Lys Ala Asp Tyr Pro Arg Arg
                245                 250                 255

Asn Ala Lys Glu Leu Cys Glu Arg Phe Gly Phe Glu Glu Arg Gly Pro
            260                 265                 270

Arg Gly Val Asp Leu Val Leu Asp Cys Ser Gly Ala Glu Val Cys Ile
        275                 280                 285

Gln Thr Gly Val Phe Val Leu Lys His Gly Gly Thr Leu Val Gln Val
        290                 295                 300

Gly Met Gly Lys Pro Asp Ile Thr Leu Asp Met His Thr Ile Ile Thr
305                 310                 315                 320

Arg Glu Leu Thr Leu Lys Gly Ser Phe Arg Tyr Gly Pro Gly Val Tyr
                325                 330                 335

Glu Leu Ala Met Asp Leu Val Ala Arg Gly Ala Val Asn Leu Lys Ser
            340                 345                 350

Leu Ile Ser His Arg Tyr Ala Phe Arg Asp Ala Leu Lys Ala Phe Glu
        355                 360                 365

Ala Asn His Thr Gly Ile Ala Glu Asp Gly Arg Pro Leu Ile Lys Ala
    370                 375                 380

Val Ile Asp Gly Pro Arg Val Asp Glu Lys Leu Glu
385                 390                 395

<210> SEQ ID NO 45
<211> LENGTH: 975
<212> TYPE: DNA
<213> ORGANISM: Rhodotorula mucilaginosa
<220> FEATURE:
<223> OTHER INFORMATION: Rhodotorula mucilaginosa strain PTD3 xylose
      reductase (XR) gene open reading frame (ORF)

<400> SEQUENCE: 45
atgtcgcagc agatccctc cgtcaagctc tcgaacggcg ccgagttccc cctccttggc      60
ttcggcacct gcagtccgc cccgggcgag gtcggcaaag ccgttgaggt cgctctcaag     120
gccggctacc gtcacctcga ccttgccaag gtctacggca accagaagga gattgctccg     180
```

```
gcgatcgcca actcgggcgt tgaccgcaag gacatcttca tcacctcgaa gctctggaac    240
ccgcagcaca agccggaact cgtcgaggct gctctcgacg acaccctcaa ggagctcggc    300
ctcgagtacc tcgacctcta cctcatccac tggccggttg ctttcccggt tgagggcgac    360
ccccactcga acctcttccc gaaggagaac ggcgagtgca agatcgacac ctcgatctcg    420
atcgtcgaca cctggaaggc gatgatcaag ctcctcgaca ctggcaagac caaggctgtc    480
ggtgttccca acttctcgcc ggccatggtc gacgccatca ccgaggccac tggtgtcaag    540
ccggtcgtca accagatcga gcgtcacccg cgcctgctcc agaaggacct cctcaagcac    600
cacaaggaga gaacattgt cgtcaccgcc tactccggct cggaaacaa cagcgtcggc     660 gagccgctcc tcctcgagca cccgaccgtc aagaagatcg ccgaggccaa gggcgccaac    720
ccgggtcagg tcctcattgc ctggggcatg acggcggcc acgccatcat tcccgagtcg     780
gttaccccgt cgcgcatcga atcgaacttc aaggtcatct cgctcaccga cgacgaggtt    840
gctgagatca acaagatcgg cgaggagaag cccgcacgtt ttaacctgcc gatcgattat    900
acaccaaagt ggaacatcaa cgtctttgac acgccgcagg agaaggacgc caagtaccag    960
gtcaagatcc agtaa                                                     975
```

<210> SEQ ID NO 46
<211> LENGTH: 324
<212> TYPE: PRT
<213> ORGANISM: Rhodotorula mucilaginosa
<220> FEATURE:
<223> OTHER INFORMATION: Rhodotorula mucilaginosa strain PTD3 xylose
      reductase (XR) gene open reading frame (ORF) translation

<400> SEQUENCE: 46

Met Ser Gln Gln Ile Pro Ser Val Lys Leu Ser Asn Gly Ala Glu Phe
 1               5                  10                  15

Pro Leu Leu Gly Phe Gly Thr Trp Gln Ser Ala Pro Gly Glu Val Gly
            20                  25                  30

Lys Ala Val Glu Val Ala Leu Lys Ala Gly Tyr Arg His Leu Asp Leu
        35                  40                  45

Ala Lys Val Tyr Gly Asn Gln Lys Glu Ile Ala Pro Ala Ile Ala Asn
    50                  55                  60

Ser Gly Val Asp Arg Lys Asp Ile Phe Ile Thr Ser Lys Leu Trp Asn
65                  70                  75                  80

Pro Gln His Lys Pro Glu Leu Val Glu Ala Ala Leu Asp Asp Thr Leu
                85                  90                  95

Lys Glu Leu Gly Leu Glu Tyr Leu Asp Leu Tyr Leu Ile His Trp Pro
            100                 105                 110

Val Ala Phe Pro Val Glu Gly Asp Pro His Ser Asn Leu Phe Pro Lys
        115                 120                 125

Glu Asn Gly Glu Cys Lys Ile Asp Thr Ser Ile Ser Ile Val Asp Thr
    130                 135                 140

Trp Lys Ala Met Ile Lys Leu Leu Asp Thr Gly Lys Thr Lys Ala Val
145                 150                 155                 160

Gly Val Ser Asn Phe Ser Pro Ala Met Val Asp Ala Ile Thr Glu Ala
                165                 170                 175

Thr Gly Val Lys Pro Val Val Asn Gln Ile Glu Arg His Pro Arg Leu
            180                 185                 190

Leu Gln Lys Asp Leu Leu Lys His His Lys Glu Lys Asn Ile Val Val
        195                 200                 205

```
Thr Ala Tyr Ser Gly Phe Gly Asn Asn Ser Val Gly Glu Pro Leu Leu
    210                 215                 220
Leu Glu His Pro Thr Val Lys Lys Ile Ala Glu Ala Lys Gly Ala Asn
225                 230                 235                 240
Pro Gly Gln Val Leu Ile Ala Trp Gly Met His Gly Gly His Ala Ile
                245                 250                 255
Ile Pro Glu Ser Val Thr Pro Ser Arg Ile Glu Ser Asn Phe Lys Val
            260                 265                 270
Ile Ser Leu Thr Asp Asp Glu Val Ala Glu Ile Asn Lys Ile Gly Glu
        275                 280                 285
Glu Lys Pro Ala Arg Phe Asn Leu Pro Ile Asp Tyr Thr Pro Lys Trp
    290                 295                 300
Asn Ile Asn Val Phe Asp Thr Pro Gln Glu Lys Asp Ala Lys Tyr Gln
305                 310                 315                 320
Val Lys Ile Gln
```

<210> SEQ ID NO 47
<211> LENGTH: 1185
<212> TYPE: DNA
<213> ORGANISM: Rhodotorula mucilaginosa
<220> FEATURE:
<223> OTHER INFORMATION: Rhodotorula mucilaginosa strain PTD3 xylose
      dehydrogenase (XDH) gene open reading frame (ORF)

<400> SEQUENCE: 47

```
atggctccga ccaacacccc actttcgcct ccgctcgccg aagacacggc cgcaacctcg    60
cgcaacgtca gcttcgttct gcacggaatc gacgacgtcc gctttgaaga gaggccggtt   120
cctgtcgact gcgatgatga tgccgccatt gtcgctccca aggctacggg aatctgcggc   180
agcgacgtac actacctcaa gcacggccga atcggcgact ttatcgttaa ggaccctatg   240
gttctcggac acgagagtgc cgccgtcgtc gtcaaggtcg gcaagaatgt caagaacgtc   300
aagccgggcg accgcgttgc ccttgagccg ggcaagtcgt gccgatcctg ctacgactgc   360
aaaggtggtc attacgaacg ctgcccggac atgatctttg cggcgactcc tccttacgat   420
ggtacccttg ccgacgcta cgttcttccg gccgacctct gctacaagct gccgacaac    480
ctgtccatgg aggagggagc tctccttgag cccatgtcgg tgggcgtcca cgcagttgcc   540
aaggttgccg agctcaagcc gggctcgaac gtggtggtgt ttggtgccgg accggtcgga   600
ctcctcaccg cagccgcggc aaaaggcctc ggtgctgccc gcgtcattgc cgtcgacatt   660
caggagagtc gcttgcaatt cgccaaggag aacggcctga tccacgacta ctgtgtcccg   720
tcaaagccgc aagaaggcga ggacaaggtt gacttccagc gacgaaacgc caaggagatt   780
cagactcggt tcggcttcac ggagcgaggg gcgaccggcg tcgactacgt ctttgagtgc   840
tctggcgccg aggtctgcat cggaacttcg gttttcctgc tcaagcacgg tggcacgatg   900
gttcagatcg gtatgggccg gcccgacatc agcctcgaca tgcacaccgt ccttacccac   960
gaactcacca tcaagggcag cttccggtac ggcccggacg tgtaccggct ctcgctcgac  1020
ctggtcgctc gcggcgccgt caacctcaaa tcgctcatca ctcaccgcta cactttcaag  1080
gaggcgaagg aggcgttcga agccaacacg aagggcgtcg gcaaagatgg ccacgccgtc  1140
atcaagatca tcattgccgg cccgctcgag tctgacacgg catga             1185
```

<210> SEQ ID NO 48
<211> LENGTH: 394
<212> TYPE: PRT
<213> ORGANISM: Rhodotorula mucilaginosa
<220> FEATURE:
<223> OTHER INFORMATION: Rhodotorula mucilaginosa strain PTD3 xylose
      dehydrogenase (XDH) gene open reading frame (ORF) translation

<400> SEQUENCE: 48

```
Met Ala Pro Thr Asn Thr Pro Leu Ser Pro Pro Leu Ala Glu Asp Thr
 1               5                  10                  15

Ala Ala Thr Ser Arg Asn Val Ser Phe Val Leu His Gly Thr Asp Asp
             20                  25                  30

Val Arg Phe Glu Glu Arg Pro Val Pro Val Asp Cys Asp Asp Asp Ala
         35                  40                  45

Ala Thr Val Ala Pro Lys Ala Thr Gly Thr Cys Gly Ser Asp Val His
 50                  55                  60

Tyr Leu Lys His Gly Arg Thr Gly Asp Phe Thr Val Lys Asp Pro Met
 65                  70                  75                  80

Val Leu Gly His Glu Ser Ala Ala Val Val Lys Val Gly Lys Asn
             85                  90                  95

Val Lys Asn Val Lys Pro Gly Asp Arg Val Ala Leu Glu Pro Gly Lys
            100                 105                 110

Ser Cys Arg Ser Cys Tyr Asp Cys Lys Gly His Tyr Glu Arg Cys
            115                 120                 125

Pro Asp Met Thr Phe Ala Ala Thr Pro Pro Tyr Asp Gly Thr Leu Ala
            130                 135                 140

Gly Arg Tyr Val Leu Pro Ala Asp Leu Cys Tyr Lys Leu Pro Asp Asn
145                 150                 155                 160

Leu Ser Met Glu Glu Gly Ala Leu Leu Glu Pro Met Ser Val Gly Val
                165                 170                 175

His Ala Val Ala Lys Val Ala Glu Leu Lys Pro Gly Ser Asn Val Val
            180                 185                 190

Val Phe Gly Ala Gly Pro Val Gly Leu Leu Thr Ala Ala Ala Ala Lys
            195                 200                 205

Gly Leu Gly Ala Ala Arg Val Thr Ala Val Asp Thr Gln Glu Ser Arg
        210                 215                 220

Leu Gln Phe Ala Lys Glu Asn Gly Leu Thr His Asp Tyr Cys Val Pro
225                 230                 235                 240

Ser Lys Pro Gln Glu Gly Glu Asp Lys Val Asp Phe Gln Arg Arg Asn
                245                 250                 255

Ala Lys Glu Thr Gln Thr Arg Phe Gly Phe Thr Glu Arg Gly Ala Thr
            260                 265                 270

Gly Val Asp Tyr Val Phe Glu Cys Ser Gly Ala Glu Val Cys Thr Gly
        275                 280                 285

Thr Ser Val Phe Leu Leu Lys His Gly Gly Thr Met Val Gln Thr Gly
        290                 295                 300

Met Gly Arg Pro Asp Thr Ser Leu Asp Met His Thr Val Leu Thr His
305                 310                 315                 320

Glu Leu Thr Thr Lys Gly Ser Phe Arg Tyr Gly Pro Asp Val Tyr Arg
                325                 330                 335

Leu Ser Leu Asp Leu Val Ala Arg Gly Ala Val Asn Leu Lys Ser Leu
            340                 345                 350

Thr Thr His Arg Tyr Thr Phe Lys Glu Ala Lys Glu Ala Phe Glu Ala
            355                 360                 365
```

```
Asn Thr Lys Gly Val Gly Lys Asp Gly His Ala Val Thr Lys Thr Thr
    370             375                 380

Thr Ala Gly Pro Leu Glu Ser Asp Thr Ala
385                 390
```